(12) United States Patent
Hitchcock et al.

(10) Patent No.: US 10,159,677 B2
(45) Date of Patent: *Dec. 25, 2018

(54) 4-OXO-3,4-DIHYDRO-1,2,3-BENZOTRIAZINE MODULATORS OF GPR139

(71) Applicant: Takeda Pharmaceutical Company Limited, Osaka (JP)

(72) Inventors: Stephen Hitchcock, San Diego, CA (US); Betty Lam, San Diego, CA (US); Holger Monenschein, San Diego, CA (US); Holly Reichard, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/683,589

(22) Filed: Aug. 22, 2017

(65) Prior Publication Data

US 2017/0348319 A1    Dec. 7, 2017

Related U.S. Application Data

(62) Division of application No. 15/382,490, filed on Dec. 16, 2016, now Pat. No. 9,770,450, which is a division of application No. 14/946,194, filed on Nov. 19, 2015, now Pat. No. 9,556,130.

(60) Provisional application No. 62/082,539, filed on Nov. 20, 2014, provisional application No. 62/184,729, filed on Jun. 25, 2015.

(51) Int. Cl.
C07D 253/08    (2006.01)
A61K 31/53    (2006.01)
A61P 25/18    (2006.01)

(52) U.S. Cl.
CPC ............ *A61K 31/53* (2013.01); *C07D 253/08* (2013.01)

(58) Field of Classification Search
CPC .............................. C07D 253/08; A61K 31/53
USPC .......................................... 514/241; 544/180
See application file for complete search history.

(56) References Cited

U.S. PATENT DOCUMENTS

| | | | |
|---|---|---|---|
| 3,794,726 | A | 2/1974 | Ariyan |
| 4,959,368 | A | 9/1990 | King |
| 7,253,164 | B2 | 8/2007 | Molteni et al. |
| 8,642,660 | B2 | 2/2014 | Goldfarb |
| 9,556,130 | B2 * | 1/2017 | Hitchcock ............ A61K 31/53 |
| 9,770,450 | B2 * | 9/2017 | Hitchcock ............ C07D 253/08 |
| 2006/0079696 | A1 | 4/2006 | Masson et al. |
| 2009/0163545 | A1 | 6/2009 | Goldfarb |
| 2016/0145218 | A1 | 5/2016 | Hitchcock et al. |

FOREIGN PATENT DOCUMENTS

| | | |
|---|---|---|
| WO | 2004/108673 A2 | 12/2004 |
| WO | 2008/018827 A1 | 6/2007 |
| WO | 2008/018827 A1 | 2/2008 |
| WO | 2011/138265 A2 | 11/2011 |
| WO | 2014/152917 A2 | 9/2014 |

OTHER PUBLICATIONS

Database CA [Online] Chemical Abstracts Service, Columbus, Ohio, US; Goldfarb, David Scott: "Method using lifespan-altering compounds for altering the lifespan of eukaryotic organisms, and screening for such compounds," Jun. 25, 2009, XP002754170.
Database Registry [Online] Chemical Abstracts Service, Columbus, Ohio, US; Aug. 24, 2008, XP002754167, retrieved from STN; Database accession No. 1043204-06-3.
Database Registry [Online] Chemical Abstracts Service, Columbus, Ohio, US; Mar. 26, 2014, XP002754168, retrieved from STN; Database accession No. 1574302-61-6.
Database Registry [Online] Chemical Abstracts Service, Columbus, Ohio, US; Aug. 4, 2010, XP002754169, retrieved from STN; Database accession No. 1234906-37-6.
Diethelm, et al., "Amine-Selective Bioconjugation Using Arene Diazonium Salts", Organic Letters, 2014, 16 (15), pp. 3908-3911.
Dvorak, et al. "Identification and SAR of glycine benzamides as potent agonists for the GPR139 receptor", *ACS Medicinal Chemistry Letters*, Jul. 20, 2015, 6 (9), pp. 1015-1018.
Hitchcock, Stephen A., "Structural Modifications that Alter the P-Glycoprotein Efflux Properties of Compounds", *Journal of Medicinal Chemistry*, 2012, vol. 55, pp. 4877-4895.
Isberg, et al., "Computer-Aided Discovery of Aromatic L-☐-Amino Acids as Agonists of the Orphan G Protein-Coupled Receptor GPR139", *Journal of Chemical Information Modeling*, 2014, vol. 54, pp. 1553-1557.
Okuzumi, et al., "Efficient solid-phase synthesis of diverse 1,2,3-benzotriazin-4-ones using tert-butyl nitrite", *Tetrahedron Letters*, 2003, vol. 44, pp. 5539-5542.
PCT/US2015/061607 "International Search Report", May 26, 2016.
Shi, et al., "Discovery and SAR of a Series of Agonists at Orphan G Protein-Coupled Receptor 139" *ACS Medicinal Chemistry Letters*, Apr. 14, 2011, vol. 2, No. 4, pp. 303-306, XP55124814.

(Continued)

*Primary Examiner* — Venkataraman Balasubramanian
(74) *Attorney, Agent, or Firm* — Matthew J. Russo; David M. Stemerick

(57) ABSTRACT

The present invention provides a method for treating a disease, disorder or condition associated with GPR139 using compounds of formula 1:

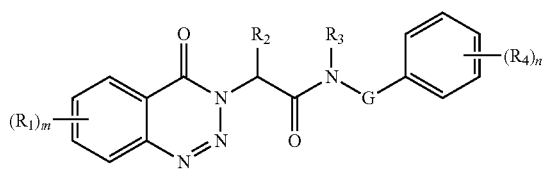

which are agonists of GPR139, certain compounds encompassed by formula 1, pharmaceutical compositions thereof, processes for making the compounds, and intermediates thereof.

32 Claims, No Drawings

(56) References Cited

OTHER PUBLICATIONS

Freshney et al., Culture of Animal Cells, A manual of Basic Technique, Alan R. Liss, Inc. 1983, New York, p. 4.
Dermer et al., Bio/Technology, 1994, 12:320.
Cecil Textbook of Medicine, edited by Bennet, J.C., and Plum F., 20$^{th}$ edition, vol. 1, 1004-1010, 1996.

\* cited by examiner

4-OXO-3,4-DIHYDRO-1,2,3-BENZOTRIAZINE MODULATORS OF GPR139

CROSS-REFERENCE TO RELATED APPLICATIONS

This application is a divisional of U.S. application Ser. No. 15/382,490, filed Dec. 16, 2016, now U.S. Pat. No. 9,770,450, which is a divisional of U.S. application Ser. No. 14/946,194, filed Nov. 19, 2015, now U.S. Pat. No. 9,556,130, which claims the benefit of U.S. Provisional Application No. 62/082,539, filed Nov. 20, 2014, and U.S. Provisional Application No. 62/184,729, filed Jun. 25, 2015, which are herein incorporated by reference.

FIELD OF THE INVENTION

The present invention relates to medicinal chemistry, pharmacology, and medicine.

BACKGROUND OF THE INVENTION

GPR139 is an orphan G-protein coupled receptor. GPR139 may be coupled with Gs, Gq and Gi signaling and appears to be constitutively active when recombinantly expressed in mammalian cells. GPR139 is abundantly expressed in the CNS (central nervous system) and to a lesser extent in the pancreas and pituitary and at low levels in other peripheral tissue.

GPR139 is highly conserved among different species. For example, human, mouse, and rat GPR139 protein sequences share greater than 94% identity at the amino acid level. The predominant expression in the brain and high degree of sequence homology across different species, suggests that GPR139 has an important role in physiology.

We have discovered that GPR139 has its strongest expression in the medial habenular nucleus of mice. The habenula receives inputs from the basal ganglia and the limbic system and sends outputs to midbrain and forebrain structures which contain dopaminergic and serotonergic neurons. Habenular nuclei are involved in pain processing, reproductive behavior, nutrition, sleep-wake cycles, stress responses, and learning.

In particular, several findings suggested a role of the habenula in schizophrenia. Large calcifications in the pineal and habenula are more common in people suffering from schizophrenia than normal controls. Moreover, an fMRI study has shown altered activation of the habenula in patients with schizophrenia. Also, following an error in a difficult matching-to-sample task, the habenula was activated in control subjects, but not in patients with schizophrenia. Chronic treatment with cocaine or amphetamine are damaging to the output pathways of the habenula in rats resulting in a schizophrenic-like state.

Thus, modulators of GPR139 are expected to be useful for treating schizophrenia and other CNS disorders such as depression.

There is a need for treatment of such conditions and others described herein with compounds that are GPR139 agonists. The present invention provides agonists of GPR139 and methods of using GPR139 agonists for treating diseases, disorders, and conditions associated with GPR139 in the form of compounds of formula 1 and other embodiments described herein. Certain activators of GPR139 are described in WO 2014/152917. Certain agonists of GPR139 are described in J. Chem. Inf. Model. 2014, 54, 1553-1557 and Med. Chem. Lett. 2011, 2, 303-306. Certain compounds of formula 1 are commercially available but have no known utility in the CNS.

SUMMARY OF THE INVENTION

The compounds of the invention are agonists of GPR139 and may be useful for the treatment of a disease, disorder or condition associated with GPR139.

One aspect of the invention provides a compound of formula 2:

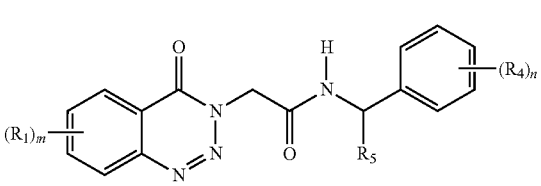

or a pharmaceutically acceptable salt thereof, wherein
m is selected from 0, 1, and 2;
n is selected from 0, 1, and 2;
each $R_1$ is independently selected from the group consisting of cyano, halo, hydroxy, amino, $C_{1-4}$ alkyl, $C_{1-4}$ alkoxy, trifluoromethyl, and trifluoromethoxy;
each $R_4$ is independently selected from the group consisting of cyano, halo, hydroxy, amino, $C_{1-4}$ alkyl, $C_{1-4}$ alkoxy, trifluoromethyl, fluoromethoxy, difluoromethoxy, and trifluoromethoxy; and
$R_5$ is selected from the group consisting of hydrogen, trifluoromethyl, and $C_{1-4}$ alkyl, provided:
  (a) if $R_5$ is hydrogen, methyl, n-propyl, i-propyl, or i-butyl, then m and n are not both 0;
  (b) if $R_5$ is hydrogen, m is 0, and n is 1, then $R_4$ is not chloro, methoxy, 3-trifluoromethyl, 4-trifluoromethyl, 4-methyl, 4-fluoro, 2-difluoromethoxy 3-difluoromethoxy, 2-trifluoromethoxy, 4-trifluoromethoxy, 4-trifluoroethoxy, or 2-(i-butoxy);
  (c) if $R_5$ is methyl, m is 0, and n is 1, then $R_4$ is not chloro, 2-fluoro, 4-fluoro, 2-bromo, 4-ethyl, 2-methyl, 4-(i-propyl), 4-(i-butyl), or 3-trifluoromethyl;
  (d) if $R_5$ is ethyl, m is 0, and n is 1, then $R_4$ is not 3-chloro, 4-chloro, 4-bromo, 4-methyl, 4-methoxy, or 2-difluoromethoxy;
  (e) if $R_5$ is n-propyl, m is 0, and n is 1, then $R_4$ is not 3-trifluoromethyl;
  (f) if $R_5$ is i-propyl, m is 0, and n is 1, then $R_4$ is not 4-fluoro or 4-methoxy;
  (g) if $R_5$ is i-butyl, m is 0, and n is 1, then $R_4$ is not 3-trifluoromethyl;
  (h) if $R_5$ is hydrogen, m is 0, and n is 2, then $R_4$ is not 2,6-difluoro, 2,4-dichloro, 3,5-dimethoxy, 3,4-dimethoxy, 4-methoxy-3-difluoromethoxy, 4-fluoro-2-trifluoromethyl, or 5-bromo-2-difluoromethoxy; and
  (i) if $R_5$ is methyl, m is 0, and n is 2, then $R_4$ is not 3,4-dimethyl, 3,4-dichloro, 2,4-dichloro, 3-fluoro-4-methoxy, 3-bromo-4-methoxy, 3-methoxy-4-isopropyloxy, or 3-methoxy-4-isobutyloxy.

In provisos (b)-(i), each $R_4$ is attached to a phenyl moiety having ring carbon atoms consecutively numbered 1 to 6 around the ring, in which ring carbon atom 1 is attached to an N-methylacetamide moiety shown in formula 2.

Another aspect of the invention provides a compound of formula 2:

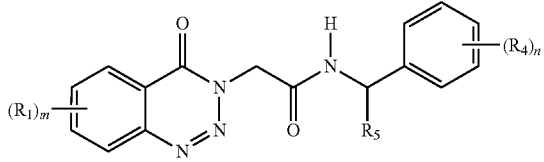

or a pharmaceutically acceptable salt thereof, wherein
m is selected from 0, 1, and 2;
n is selected from 0, 1, and 2;
each $R_1$ is independently selected from the group consisting of cyano, halo, hydroxy, amino, $C_{1-4}$ alkyl, $C_{1-4}$ alkoxy, trifluoromethyl, and trifluoromethoxy;
each $R_4$ is independently selected from the group consisting of cyano, halo, hydroxy, amino, $C_{1-4}$ alkyl, $C_{1-4}$ alkoxy, trifluoromethyl, fluoromethoxy, difluoromethoxy, and trifluoromethoxy; and
$R_5$ is selected from the group consisting of hydrogen, trifluoromethyl, and $C_{1-4}$ alkyl, provided the compound of formula 2 is not:
N-[[2-(2-methylpropoxy)phenyl]methyl]-4-oxo-1,2,3-benzotriazine-3(4H)-acetamide;
N-[(2,6-difluorophenyl)methyl]-4-oxo-1,2,3-benzotriazine-3(4H)-acetamide;
N-[(3,5-dimethoxyphenyl)methyl]-4-oxo-1,2,3-benzotriazine-3(4H)-acetamide;
N-[[3-(difluoromethoxy)phenyl]methyl]-4-oxo-1,2,3-benzotriazine-3(4H)-acetamide;
N-[[3-(difluoromethoxy)-4-methoxyphenyl]methyl]-4-oxo-1,2,3-benzotriazine-3(4H)-acetamide;
N-[[5-bromo-2-(difluoromethoxy)phenyl]methyl]-4-oxo-1,2,3-benzotriazine-3(4H)-acetamide;
N-[[2-(trifluoromethoxy)phenyl]methyl]-4-oxo-1,2,3-benzotriazine-3(4H)-acetamide;
N-[[4-(trifluoromethoxy)phenyl]methyl]-4-oxo-1,2,3-benzotriazine-3(4H)-acetamide;
N-[[4-fluoro-2-(trifluoromethyl)phenyl]methyl]-4-oxo-1,2,3-benzotriazine-3(4H)-acetamide;
4-oxo-N-[[4-(trifluoromethyl)phenyl]methyl]-1,2,3-benzotriazine-3(4H)-acetamide;
N-[(3-methoxyphenyl)methyl]-4-oxo-1,2,3-benzotriazine-3(4H)-acetamide;
N-[(3,4-dimethoxyphenyl)methyl]-4-oxo-1,2,3-benzotriazine-3(4H)-acetamide;
N-[(2,4-dichlorophenyl)methyl]-4-oxo-1,2,3-benzotriazine-3(4H)-acetamide;
N-[[3-(trifluoromethyl)phenyl]methyl]-4-oxo-1,2,3-benzotriazine-3(4H)-acetamide;
N-[(4-chlorophenyl)methyl]-4-oxo-1,2,3-benzotriazine-3(4H)-acetamide;
N-[(4-methylphenyl)methyl]-4-oxo-1,2,3-benzotriazine-3(4H)-acetamide;
N-[(4-methoxyphenyl)methyl]-4-oxo-1,2,3-benzotriazine-3(4H)-acetamide;
N-[(2-methoxyphenyl)methyl]-4-oxo-1,2,3-benzotriazine-3(4H)-acetamide;
N-[(3-chlorophenyl)methyl]-4-oxo-1,2,3-benzotriazine-3(4H)-acetamide;
N-[(2-chlorophenyl)methyl]-4-oxo-1,2,3-benzotriazine-3(4H)-acetamide;
N-[(4-fluorophenyl)methyl]-4-oxo-1,2,3-benzotriazine-3(4H)-acetamide;
N-(phenylmethyl)-4-oxo-1,2,3-benzotriazine-3(4H)-acetamide;
N-[1-(3,4-dimethylphenyl)ethyl]-4-oxo-1,2,3-benzotriazine-3(4H)-acetamide;
N-[1-(3,4-dichlorophenyl)ethyl]-4-oxo-1,2,3-benzotriazine-3(4H)-acetamide;
N-[1-((4-(1-methylethyl)phenyl)ethyl]-4-oxo-1,2,3-benzotriazine-3(4H)-acetamide;
N-[1-(2-methylphenyl)ethyl]-4-oxo-1,2,3-benzotriazine-3(4H)-acetamide;
N-[1-(3-methoxy-4-isobutyloxyphenyl)ethyl]-4-oxo-1,2,3-benzotriazine-3(4H)-acetamide;
N-[1-(3-bromo-4-methoxyphenyl)ethyl]-4-oxo-1,2,3-benzotriazine-3(4H)-acetamide;
N-[1-(3-methoxy-4-isopropyloxyphenyl)ethyl]-4-oxo-1,2,3-benzotriazine-3(4H)-acetamide;
N-[1-(4-ethylphenyl)ethyl]-4-oxo-1,2,3-benzotriazine-3(4H)-acetamide;
N-[1-[4-(2-methylpropyl)phenyl]ethyl]-4-oxo-1,2,3-benzotriazine-3(4H)-acetamide;
N-[1-(2,4-dichlorophenyl)ethyl]-4-oxo-1,2,3-benzotriazine-3(4H)-acetamide;
N-[1-(4-fluorophenyl)ethyl]-4-oxo-1,2,3-benzotriazine-3(4H)-acetamide;
N-[1-(3-fluoro-4-methoxyphenyl)ethyl]-4-oxo-1,2,3-benzotriazine-3(4H)-acetamide;
N-[1-(2-fluorophenyl)ethyl]-4-oxo-1,2,3-benzotriazine-3(4H)-acetamide;
N-[1-[3-(trifluoromethyl)phenyl]ethyl]-4-oxo-1,2,3-benzotriazine-3 (4H)-acetamide;
N-[1-(2-bromophenyl)ethyl]-4-oxo-1,2,3-benzotriazine-3(4H)-acetamide;
N-[1-(4-chlorophenyl)ethyl]-4-oxo-1,2,3-benzotriazine-3(4H)-acetamide;
N-[1-(3-chlorophenyl)ethyl]-4-oxo-1,2,3-benzotriazine-3(4H)-acetamide;
N-[1-(2-chlorophenyl)ethyl]-4-oxo-1,2,3-benzotriazine-3(4H)-acetamide;
N-(1-phenylethyl)-4-oxo-1,2,3-benzotriazine-3(4H)-acetamide;
N-[1-(2-difluoromethoxyphenyl)propyl]-4-oxo-1,2,3-benzotriazine-3(4H)-acetamide;
N-[1-(3-chlorophenyl)propyl]-4-oxo-1,2,3-benzotriazine-3(4H)-acetamide;
N-[1-(4-chlorophenyl)propyl]-4-oxo-1,2,3-benzotriazine-3(4H)-acetamide;
N-[1-(4-methoxyphenyl)propyl]-4-oxo-1,2,3-benzotriazine-3 (4H)-acetamide;
N-[1-(4-bromophenyl)propyl]-4-oxo-1,2,3-benzotriazine-3(4H)-acetamide;
N-[1-[3-(trifluoromethyl)phenyl]butyl]-4-oxo-1,2,3-benzotriazine-3 (4H)-acetamide;
N-(1-phenylbutyl)-4-oxo-1,2,3-benzotriazine-3 (4H)-acetamide;
N-(2-methyl-1-phenylpropyl)-4-oxo-1,2,3-benzotriazine-3 (4H)-acetamide;
N-[1-(4-fluorophenyl)-2-methylpropyl]-4-oxo-1,2,3-benzotriazine-3 (4H)-acetamide;
N-[1-(4-methoxyphenyl)-2-methylpropyl]-4-oxo-1,2,3-benzotriazine-3 (4H)-acetamide;
N-[3-methyl-1-[3-(trifluoromethyl)phenyl]butyl]-4-oxo-1,2,3-benzotriazine-3 (4H)-acetamide;
N-[3-methyl-1-phenylbutyl]-4-oxo-1,2,3-benzotriazine-3 (4H)-acetamide;

2-(4-oxobenzo[d][1,2,3]triazin-3(4H)-yl)-N-(4-(2,2,2-trifluoroethoxy)benzyl)acetamide; or 2-(4-oxobenzo[d][1,2,3]triazin-3 (4H)-yl)-N-(1-(p-tolyl)propyl)acetamide.

The specific compounds mentioned in this paragraph, which are defined to be outside the scope of compounds of formula 2, are commercially available, but are not disclosed as having central nervous system activity.

A further aspect of the invention provides a compound of formula 3:

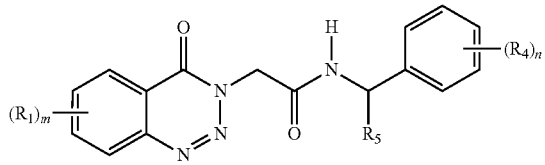

3 or a pharmaceutically acceptable salt thereof, wherein
m is selected from 0, 1, and 2;
n is selected from 0, 1, and 2;
each $R_1$ is independently selected from the group consisting of cyano, halo, hydroxy, amino, $C_{1-4}$ alkyl, $C_{1-4}$ alkoxy, trifluoromethyl, and trifluoromethoxy;
each $R_4$ is independently selected from the group consisting of cyano, halo, hydroxy, amino, $C_{1-4}$ alkyl, $C_{1-4}$ alkoxy, trifluoromethyl, fluoromethoxy, difluoromethoxy, and trifluoromethoxy;
$R_5$ is selected from the group consisting of hydrogen, trifluoromethyl, and $C_{1-4}$ alkyl, provided:
(a) if $R_5$ is hydrogen or $C_{1-4}$ alkyl, then m and n are not both 0;
(b) if $R_5$ is hydrogen, m is 0, and n is 1, then $R_4$ is not halo, $C_{1-4}$ alkyl, $C_{1-4}$ alkoxy, trifluoromethyl, difluoromethoxy, or trifluoromethoxy;
(c) if $R_5$ is $C_{1-4}$ alkyl, m is 0, and n is 1, then $R_4$ is not halo, $C_{1-4}$ alkyl, $C_{1-4}$ alkoxy, trifluoromethyl, or difluoromethoxy;
(d) if $R_5$ is hydrogen, m is 0, and n is 2, then $R_4$ is not halo, $C_{1-4}$ alkoxy, or difluoromethoxy; and
(e) if $R_5$ is $C_{1-4}$ alkyl, m is 0, and n is 2, then $R_4$ is not halo, $C_{1-4}$ alkyl, trifluoromethyl, difluoromethoxy, or $C_{1-4}$ alkoxy.

An additional aspect of the invention provides a compound which is (S)-2-(4-oxobenzo[d][1,2,3]triazin-3(4H)-yl)-N-(1-(4-(trifluoromethoxy)phenyl)ethyl)acetamide or a pharmaceutically acceptable salt thereof.

Another aspect of the invention provides a compound which is (S)-2-(4-oxobenzo[d][1,2,3]triazin-3(4H)-yl)-N-(1-(4-(trifluoromethyl)phenyl)ethyl)acetamide or a pharmaceutically acceptable salt thereof.

A further aspect of the invention provides a compound which is (S)-2-(5-fluoro-4-oxobenzo[d][1,2,3]triazin-3(4H)-yl)-N-(1-p-tolylethyl)acetamide or a pharmaceutically acceptable salt thereof.

An additional aspect of the invention provides a compound which is (S)-2-(5-methoxy-4-oxobenzo[d][1,2,3]triazin-3(4H)-yl)-N-(1-(4-(trifluoromethyl)phenyl)ethyl)acetamide or a pharmaceutically acceptable salt thereof.

Another aspect of the invention provides a pharmaceutical composition comprising a compound or pharmaceutically acceptable salt as defined in the preceding paragraphs, and a pharmaceutically acceptable excipient.

A further aspect of the invention provides a compound or pharmaceutically acceptable salt as defined in the preceding paragraphs for use as a medicament.

An additional aspect of the invention provides a compound of formula 1,

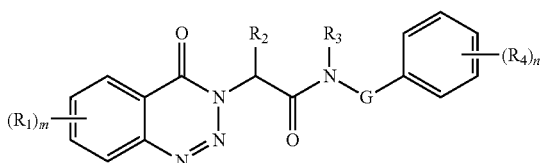

1 or a pharmaceutically acceptable salt thereof, for use as a medicament, wherein:
m is selected from 0, 1, and 2;
n is selected from 0, 1, and 2;
each $R_1$ is independently selected from the group consisting of cyano, halo, hydroxy, amino, $C_{1-4}$ alkyl, $C_{1-4}$ alkoxy, trifluoromethyl, and trifluoromethoxy;
$R_2$ is selected from the group consisting of hydrogen and $C_{1-4}$ alkyl;
$R_3$ is selected from the group consisting of hydrogen and methyl;
each $R_4$ is independently selected from the group consisting of cyano, halo, hydroxy, amino, $C_{1-4}$ alkyl, $C_{1-4}$ alkoxy, trifluoromethyl, fluoromethoxy, difluoromethoxy, and trifluoromethoxy;
G is selected from the group consisting of —$CHR_5$—, —$CHR_5$—$CH_2$—, and —$CH_2$—$CHR_5$—; and
$R_5$ is selected from the group consisting of hydrogen, trifluoromethyl, and $C_{1-4}$ alkyl.

Another aspect of the invention provides a compound or pharmaceutically acceptable salt as defined in the preceding paragraphs, for use in treating a disease, disorder or condition selected from the group consisting of schizophrenia, autism spectrum disorder, sleep disorders, depression, bipolar disorder, cognitive impairment, attention deficit hyperactivity disorder, post-traumatic stress disorder, substance abuse, drug addiction, eating disorders, obsessive compulsive disorder, anxiety disorders, pain, and fibromyalgia.

A further aspect of the invention provides a method of treating a disease, disorder or condition associated with GPR139 in a subject, the method comprising administering an effective amount of a compound or pharmaceutically acceptable salt as defined in the preceding paragraphs.

An additional aspect of the invention provides a method of treating a disease, disorder or condition in a subject, the method comprising administering an effective amount of a compound or pharmaceutically acceptable salt as defined in the preceding paragraphs, wherein the disease, disorder or condition is selected from the group consisting of schizophrenia, autism spectrum disorder, sleep disorders, depression, bipolar disorder, cognitive impairment, attention deficit hyperactivity disorder, post-traumatic stress disorder, substance abuse, drug addiction, eating disorders, obsessive compulsive disorder, anxiety disorders, pain, and fibromyalgia.

Another aspect of the invention provides a use of a compound or pharmaceutically acceptable salt as defined in the preceding paragraphs, for the manufacture of a medicament for the treatment of a disease, disorder or condition associated with GPR139.

A further aspect of the invention provides a combination comprising a compound or pharmaceutically acceptable salt as defined in the preceding paragraphs, and at least one additional pharmacologically active agent.

An additional aspect of the invention provides processes from making GPR139 agonists and intermediates thereof.

DETAILED DESCRIPTION OF THE INVENTION

The term "$C_{1-4}$ alkyl" refers to a straight or branched alkyl chain of one to four carbon atoms.

The term "$C_{1-4}$ alkoxy" refers to a $C_{1-4}$ alkyl attached through an oxygen atom.

The terms "halogen" and "halo" refer to chloro, fluoro, bromo or iodo.

The term "pharmaceutically acceptable salt" refers to a salt of pharmaceutically acceptable organic acids and bases or inorganic acids and bases, and includes those described in Journal of Pharmaceutical Science, 66, 2-19 (1977). An example is the hydrochloride salt.

The term "amino" refers to —$NH_2$.

The term "agonist" refers to both full agonists and partial agonists and other agonists.

The term "substantially enantiomerically pure" refers to greater than 90% enantiomeric purity for a given stereocenter. Thus, the term "substantially enantiomerically pure" refers to greater than 80% ee (enantiomeric excess). For compounds that exist as stereoisomers, such stereoisomers may be substantially enantiomerically pure, or preferably, may have greater than 97% enantiomeric purity, or more preferably, may have greater than 99% enantiomeric purity at the stereocenter.

The skilled artisan will appreciate that certain of the compounds of the invention may exist as isomers. All stereoisomers of the compounds of the invention, including geometric isomers, enantiomers, and diastereomers, in any ratio, are contemplated to be within the scope of the present invention.

The skilled artisan will appreciate that certain of the compounds of the invention exist as tautomers. All tautomeric forms the compounds of the invention are contemplated to be within the scope of the present invention.

Compounds of the invention also include all isotopic variations, in which at least one atom is replaced by an atom having the same atomic number, but an atomic mass different from the atomic mass most commonly found in nature.

The terms "the compounds of the invention" and "a compound of the invention" and the like include the embodiment of formula 1, formula 2, formula 3, and the other more particular embodiments encompassed by formula 1, 2 and 3 described herein, each of the exemplified compounds described herein, and a pharmaceutically acceptable salt of each of these embodiments.

Further embodiments of compounds of the invention are provided below:

(1a) One embodiment relates to compounds of formula 1 wherein G is —$CHR_5$—.

(1b) One embodiment relates to compounds of formula 1 and embodiment (1a) wherein $R_5$ is $C_{1-4}$ alkyl.

(1c) One embodiment relates to compounds of formula 1 and embodiment (1a) wherein $R_5$ is methyl.

(1d) One embodiment relates to compounds of formula 1 and embodiments (1b) and (1c) wherein the compound is substantially enantiomerically pure and has the stereochemical configuration represented by formula 1A,

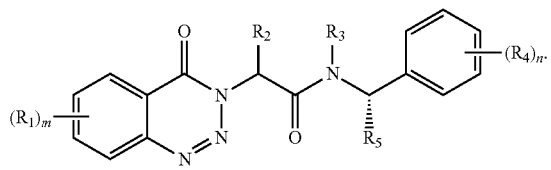

(1e) One embodiment relates to compounds of formula 1 and embodiments (1a), (1b), (1c), and (1d) wherein $R_2$ is hydrogen.

(1f) One embodiment relates to compounds of formula 1 and embodiments (1a), (1b), (1c), (1d), and (1e) wherein $R_3$ is hydrogen.

(1g) One embodiment relates to compounds of formula 1 and embodiments (1a), (1b), (1c), (1d), (1e), and (1f) wherein m is 0.

(1h) One embodiment relates to compounds of formula 1 and embodiments (1a), (1b), (1c), (1d), (1f), and (1g) wherein n is 0.

(1i) One embodiment relates to compounds of formula 1 and embodiments (1a), (1b), (1c), (1d), (1f), and (1g) wherein n is 1 and $R_4$ is selected from the group consisting of halo, $C_{1-4}$ alkyl, $C_{1-4}$ alkoxy, trifluoromethyl, fluoromethoxy, difluoromethoxy, and trifluoromethoxy.

(1j) One embodiment relates to compounds of formula 1 and embodiments (1a), (1b), (1c), (1d), (1f), and (1g) wherein n is 1 and $R_4$ is selected from the group consisting of halo, $C_{1-4}$ alkyl, $C_{1-4}$ alkoxy, trifluoromethyl, and trifluoromethoxy.

(1k) One embodiment relates to compounds of formula 1 and embodiments (1a), (1b), (1c), (1d), (1f), and (1g) wherein n is 1 and $R_4$ is selected from the group consisting of cyano, hydroxy, amino, fluoromethoxy, and trifluoromethoxy.

(1l) One embodiment relates to compounds of formula 1 and embodiments (1a), (1b), (1c), (1d), (1f), and (1g) wherein n is 1 and $R_4$ is trifluoromethoxy.

(1m) One embodiment relates to compounds of formula 1 and embodiments (1a), (1b), (1c), (1d), (1f), and (1g) wherein n is 2.

(1n) One embodiment relates to compounds of formula 1 and embodiments (1a), (1b), (1c), (1d), (1f), and (1g) wherein n is 2 and $R_4$, is each time taken, independently selected from the group consisting of halo, $C_{1-4}$ alkyl, $C_{1-4}$ alkoxy, trifluoromethyl, fluoromethoxy, difluoromethoxy, and trifluoromethoxy.

(1o) One embodiment relates to compounds of formula 1 and embodiments (1a), (1b), (1c), (1d), (1f), and (1g) wherein n is 2 and $R_4$, is each time taken, independently selected from the group consisting of halo, $C_{1-4}$ alkyl, $C_{1-4}$ alkoxy, trifluoromethyl, and trifluoromethoxy.

(1p) One embodiment relates to compounds of formula 1 and embodiments (1a), (1b), (1c), (1d), (1f), and (1g) wherein n is 2 and $R_4$, each time taken, is independently selected from the group consisting of cyano, hydroxy, amino, trifluoromethyl, fluoromethoxy, difluoromethoxy, and trifluoromethoxy.

(1q) One embodiment relates to compounds of formula 1 and embodiments (1a), (1b), (1c), (1d), (1f), and (1g) wherein n is 2 and $R_4$, each time taken, is independently selected from the group consisting of trifluoromethyl, fluoromethoxy, difluoromethoxy, and trifluoromethoxy.

(1r) One embodiment relates to compounds of formula 1 and embodiments (1a), (1b), (1c), (1d), and (1f) wherein m is 1.

(1s) One embodiment relates to compounds of formula 1 and embodiments (1a), (1b), (1c), (1d), and (1f) wherein m is 1 and $R_1$ is selected from the group consisting of halo, $C_{1-4}$ alkyl, $C_{1-4}$ alkoxy, trifluoromethyl, and trifluoromethoxy.

(1t) One embodiment relates to compounds of formula 1 and embodiments (1a), (1b), (1c), (1d), and (1f) wherein m is 1 and $R_1$ is selected from the group consisting of halo, $C_{1-4}$ alkyl, $C_{1-4}$ alkoxy, and trifluoromethyl.

(1u) One embodiment relates to compounds of formula 1 and embodiments (1r), (1s), and (1t) wherein n is 0.

(1v) One embodiment relates to compounds of formula 1 and embodiments (1r), (1s), and (1t) wherein n is 1 and $R_4$ is selected from the group consisting of halo, $C_{1-4}$ alkyl, $C_{1-4}$ alkoxy, trifluoromethyl, fluoromethoxy, difluoromethoxy, and trifluoromethoxy.

(1w) One embodiment relates to compounds of formula 1 and embodiments (1r), (1s), and (1t) wherein n is 1 and $R_4$ is selected from the group consisting of halo, $C_{1-4}$ alkyl, $C_{1-4}$ alkoxy, trifluoromethyl, and trifluoromethoxy.

(1x) One embodiment relates to compounds of formula 1 and embodiments (1a), (1b), (1c), (1d), and (1f) wherein m is 2.

(1y) One embodiment relates to compounds of formula 1 and embodiment (1x) wherein n is 1 and $R_4$ is selected from the group consisting of halo, $C_{1-4}$ alkyl, $C_{1-4}$ alkoxy, trifluoromethyl, fluoromethoxy, difluoromethoxy, and trifluoromethoxy (1z). One embodiment relates to compounds of formula 1 and embodiment (1x) wherein n is 2.

(2a) One embodiment relates to compounds of formula 2 wherein $R_5$ is $C_{1-4}$ alkyl.

(2b) One embodiment relates to compounds formula 2 wherein $R_5$ is selected from the group consisting of methyl, ethyl, and isopropyl.

(2c) One embodiment relates to compounds of formula 2 wherein $R_5$ is methyl.

(2d) One embodiment relates to compounds of formula 2 and embodiments (2a), (2b), and (2c) wherein the compound is substantially enantiomerically pure and has the stereochemical configuration represented by formula 2A,

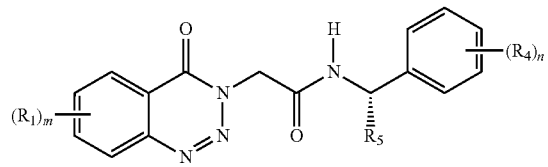

2A (2e) One embodiment relates to compounds of formula 2 and embodiments (2a), (2b), (2c), and (2d) wherein m is 0.

(2f) One embodiment relates to compounds of embodiments (2a), (2b), (2c), (2d), and (2e) wherein n is 1 and $R_4$ is trifluoromethoxy.

(2j) One embodiment relates to compounds of embodiments (2a), (2b), (2c), (2d), and (2e) wherein n is 2 and $R_4$, each time taken, is independently selected from the group consisting of trifluoromethyl, fluoromethoxy, difluoromethoxy, and trifluoromethoxy.

(2k) One embodiment relates to compounds of formula 2 and embodiments (2a), (2b), (2c), and (2d) wherein m is 1.

(2l) One embodiment relates to compounds of formula 2 and embodiments (2a), (2b), (2c), and (2d) wherein m is 2.

(2m) One embodiment relates to compounds of formula 2 and embodiments (2a), (2b), (2c), and (2d) wherein m is 1 and $R_1$ is selected from the group consisting of halo, $C_{1-4}$ alkyl, $C_{1-4}$ alkoxy, trifluoromethyl, and trifluoromethoxy.

(2n) One embodiment relates to compounds of formula 2 and embodiments (2a), (2b), (2c), and (2d) wherein m is 1 and $R_1$ is selected from the group consisting of halo, $C_{1-4}$ alkyl, $C_{1-4}$ alkoxy, and trifluoromethyl.

(3a) One embodiment relates to compounds of formula 3 wherein $R_5$ is $C_{1-4}$ alkyl.

(3b) One embodiment relates to compounds formula 3 wherein $R_5$ is selected from the group consisting of methyl, ethyl, and isopropyl.

(3c) One embodiment relates to compounds of formula 3 wherein $R_5$ is methyl.

(3d) One embodiment relates to compounds of formula 3 and embodiments (3a), (3b), and (3c) wherein the compound is substantially enantiomerically pure and has the stereochemical configuration represented by formula 3A:

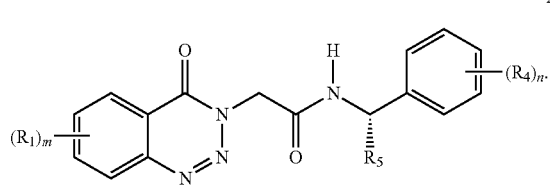

3A (3e) One embodiment relates to compounds of formula 3 and embodiments (3a), (3b), (3c), and (3d) wherein m is 0.

(3f) One embodiment relates to compounds of formula 3 and embodiments (3a), (3b), (3c), (3d), and (3e) wherein $R_5$ is hydrogen.

(3g) One embodiment relates to compounds of embodiment (3f) wherein n is 1 and $R_4$ is selected from the group consisting of cyano, hydroxy, amino, and fluoromethoxy.

(3h) One embodiment relates to compounds of embodiment (3f) wherein n is 2 and $R_4$, each time taken, is independently selected from the group consisting of cyano, hydroxy, amino, $C_{1-4}$ alkyl, fluoromethoxy, and trifluoromethoxy.

(3i) One embodiment relates to compounds of embodiment (3f) wherein n is 2 and $R_4$, each time taken, is independently selected from the group consisting of $C_{1-4}$ alkyl, fluoromethoxy, and trifluoromethoxy.

(3j) One embodiment relates to compounds of embodiment (3f) wherein n is 2 and $R_4$, each time taken, is independently selected from the group consisting of $C_{1-4}$ alkyl and trifluoromethoxy.

(3k) One embodiment relates to compounds of formula 3 and embodiments (3a), (3b), (3c), (3d), and (3e) wherein m is 2.

Another embodiment relates to a pharmaceutically acceptable salt of each of the above embodiments, specifically, formula 1, formula 2, formula 3, embodiments (1a)-(1z), embodiments (2a)-(2n), and embodiments (3a)-(3k).

Another embodiment relates to a pharmaceutically acceptable salt of each of the exemplified compounds.

The compounds of the invention can be prepared by a variety of procedures, some of which are described below. All substituents, unless otherwise indicated, are as previously defined. It is understood that formulae 2 and 3 are encompassed by formula 1 and that the general procedures below for preparing compounds of formula 1 are also applicable to preparing compounds of formulae 2 and 3. The products of each step can be recovered by conventional methods including extraction, evaporation, precipitation, chromatography, filtration, trituration, crystallization, and the like. The procedures may require protection of certain groups, for example hydroxy, amino, or carboxy groups to minimize unwanted reactions. The selection, use, and removal of protecting groups are well known and appreciated as standard practice, for example T. W. Greene and P. G. M. Wuts in Protective Groups in Organic Chemistry (John Wiley and Sons, 1991). It is also readily apparent that specific stereoisomers can be prepared by stereospecific synthesis using substantially enantiomerically pure starting materials or by separation of isomers by chromatography, recrystallization, either with or without auxiliaries, or other means.

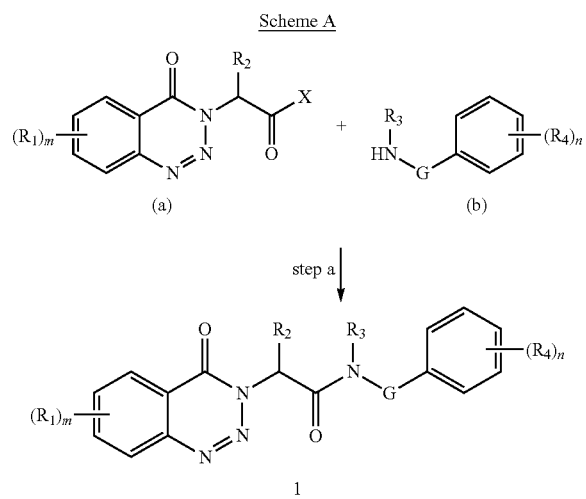

Scheme A

Scheme A, step a, depicts an amide forming reaction of an appropriate compound of formula (a) with an appropriate compound of formula (b) to give a compound of formula 1. An appropriate compound of formula (a) is one in which $R_1$, $R_2$, and m are as desired in the final compound of formula 1 or give rise to $R_1$ and $R_2$ as desired in the final product of formula 1 and X is hydroxyl or a leaving group, such as halo, specifically chloro, or imidazolyl, an activating moiety, a mixed anhydride of another carboxylic acid, such as formic acid, acetic acid, or represents the other part of a symmetrical anhydride formed from two compounds of formula (a). An appropriate compound of formula (b) is one in which $R_3$, $R_4$, G, and n are as desired in the final compound of formula 1 or give rise to $R_3$ and $R_4$ as desired in the final product of formula 1. Compounds of formula (a) and (b) are readily prepared by procedures that are well known in the art and analogously to procedures specifically provided herein.

For example, standard amide forming conditions can be used, such as those using coupling agents, including those used in peptide couplings, such as 2-(1H-7-azabenzotriazol-1-yl)-1,1,3,3-tetramethyluronium hexafluorophosphate methanaminium (HATU), dicyclohexylcarbodiimide (DCC), and 1-(3-dimethylaminopropyl)-3-ethylcarbodiimide hydrochloride. If necessary or desired, an additive such as 4-(dimethylamino)pyridine, 1-hydroxybenzotriazole, and the like may be used to facilitate the reaction. Such reactions are generally carried out using a base, such as N-methylmorpholine or triethylamine, in a wide variety of suitable solvents such as DCM, DMF, NMP, dimethylacetamide, THF, and the like. Such amide forming reactions are well understood and appreciated in the art.

It will be recognized by one of ordinary skill in the art that the compounds in Scheme A can be elaborated in a variety of ways to give compounds of formula 1. Such reactions include hydrolysis, oxidation, reduction, alkylation, amidations, sulfonations, and the like.

Also, in an optional step, not shown, the compounds of formula 1 bearing acidic or basic groups can be converted to a pharmaceutically acceptable salt by methods well known and appreciated in the art.

The following examples are intended to be illustrative and non-limiting, and represent specific embodiments of the present invention.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), and $CD_3OD$ (deuteromethanol or methanol-$d_4$). The mass spectra were recorded using either electrospray ionization (ESI) or atmospheric pressure chemical ionization.

The examples below were carried out in appropriate vessels and were typically stirred. Where indicated, products of certain preparations and examples are purified by mass-triggered HPLC. Where indicated products of the preparations and examples were purified by the following methods: HPLC Method A: Pump: Shimadzu LC-8A; UV/Vis: SPD-20A; Software: LCsolution. A Phenomenex Gemini® C18, 5 μm, ID 30×100 mm column was used and eluted with gradients of ACN (containing 0.035% TFA) and water (containing 0.005% TFA). A 10% to 100% ACN gradient was used unless otherwise indicated. SFC purification: Multigram II Berger SFC; ChiralPak AD-H (5 um, 21×150 mm) column was used and eluted with gradients of liquid $CO_2$ and isopropanol. After isolation by chromatography, the solvent was removed and the product was obtained by evaporating product containing fractions (e.g., GeneVac™), rotary evaporator, evacuated flask, lyophilization, etc.

As used herein terms have their using conventional abbreviations, unless otherwise indicated, for example: room temperature (RT), methanol (MeOH), ethanol (EtOH), isopropanol (IPA), acetonitrile (MeCN or AcCN), tetrahydrofuran (THF), ethyl acetate (EtOAc), dichloromethane (DCM), dimethyl sulfoxide (DMSO), dimethylformamide (DMF), hydrochloric acid (HCl), diisopropylethylamine (DIEA or DIPEA), hydroxybenzotriazole (HOBT), N-(3-dimethylaminopropyl)-N'-ethylcarbonate (EDC), and the like.

PREPARATION 1

2-(6-fluoro-4-oxobenzo[d][1,2,3]triazin-3(4H)-yl) acetic acid

To a suspension of 6-fluoro-1H-benzo[d][1,3]oxazine-2,4-dione (1 g, 5.52 mmol) in water (7.9 mL) was added solution of 2-aminoacetic acid (0.456 g, 6.07 mmol) and triethylamine (0.84 mL, 6.07 mmol) in water (3 mL). The reaction mixture was stirred at 40° C. for 1 h then cooled to 0° C. Concentrated HCl (2.8 mL, 33.1 mmol) and sodium nitrite (0.476 g, 6.90 mmol) were added slowly. The mixture was allowed to warm to RT over 1 h then filtered and washed with water to produce the title compound as an off-white solid (1.103 g, 90%).

PREPARATION 2

2-(8-fluoro-4-oxobenzo[d][1,2,3]triazin-3(4H)-yl) acetic acid

The title compound was prepared in a manner similar to Preparation 1 using 8-fluoro-1H-benzo[d][1,3]oxazine-2,4-dione to give the title compound as a tan solid (106 mg, 43%).

PREPARATION 3

2-(5-fluoro-4-oxobenzo[d][1,2,3]triazin-3(4H)-yl) acetic acid

The title compound was prepared in a manner similar to Preparation 1 using 5-fluoro-1H-benzo[d][1,3]oxazine-2,4-dione to give the title compound as a tan solid (64 mg, 26%).

PREPARATION 4

2-(6-methoxy-4-oxobenzo[d][1,2,3]triazin-3(4H)-yl) acetic acid

The title compound was prepared in a manner similar to Preparation 1 using 6-methoxy-1H-benzo[d][1,3]oxazine-2,4-dione to give the title compound as a tan solid (74 mg, 30%).

PREPARATION 5

2-(6-chloro-4-oxobenzo[d][1,2,3]triazin-3(4H)-yl) acetic acid

The title compound was prepared in a manner similar to Preparation 1 using 6-chloro-1H-benzo[d][1,3]oxazine-2,4-dione to give the title compound as a tan solid (172 mg, 71%).

PREPARATION 6

2-(7-chloro-4-oxobenzo[d][1,2,3]triazin-3(4H)-yl) acetic acid

The title compound was prepared in a manner similar to Preparation 1 using 7-chloro-1H-benzo[d][1,3]oxazine-2,4-dione to give the title compound as a tan solid (204 mg, 84%).

PREPARATION 7

2-(8-chloro-4-oxobenzo[d][1,2,3]triazin-3(4H)-yl) acetic acid

The title compound was prepared in a manner similar to Preparation 1 using 8-chloro-1H-benzo[d][1,3]oxazine-2,4-dione to give the title compound as a yellow solid (167 mg, 69%).

PREPARATION 8

2-(8-methoxy-4-oxobenzo[d][1,2,3]triazin-3(4H)-yl) acetic acid

The title compound was prepared in a manner similar to Preparation 1 using 8-methoxy-1H-benzo[d][1,3]oxazine-2,4-dione to give the title compound as a tan solid (98 mg, 40%).

PREPARATION 9

2-(6-methyl-4-oxobenzo[d][1,2,3]triazin-3(4H)-yl) acetic acid

The title compound was prepared in a manner similar to Preparation 1 using 6-methyl-1H-benzo[d][1,3]oxazine-2,4-dione to give the title compound as a tan solid (91 mg, 37%).

PREPARATION 10

2-(6,8-dichloro-4-oxobenzo[d][1,2,3]triazin-3(4H)-yl)acetic acid

The title compound was prepared in a manner similar to Preparation 1 using 6,8-dichloro-1H-benzo[d][1,3]oxazine-2,4-dione to give the title compound as a tan solid (180 mg, 76%).

PREPARATION 11

2-(8-methyl-4-oxobenzo[d][1,2,3]triazin-3(4H)-yl) acetic acid

The title compound was prepared in a manner similar to Preparation 1 using 8-methyl-1H-benzo[d][1,3]oxazine-2,4-dione to give the title compound as a tan solid (65 mg, 26%).

PREPARATION 12

2-(7-methyl-4-oxobenzo[d][1,2,3]triazin-3(4H)-yl) acetic acid

The title compound was prepared in a manner similar to Preparation 1 using 7-methyl-1H-benzo[d][1,3]oxazine-2,4-dione to give the title compound as an off-white solid (81 mg, 33%).

PREPARATION 13

2-(5-methyl-4-oxobenzo[d][1,2,3]triazin-3(4H)-yl) acetic acid

The title compound was prepared in a manner similar to Preparation 1 using 5-methyl-1H-benzo[d][1,3]oxazine-2,4-dione to give the title compound as a tan solid (71 mg, 29%).

PREPARATION 14

2-(7-methoxy-4-oxobenzo[d][1,2,3]triazin-3(4H)-yl) acetic acid

The title compound was prepared in a manner similar to Preparation 1 using 7-methoxy-1H-benzo[d][1,3]oxazine-2,4-dione to give the title compound as a tan solid (236 mg, 78%).

PREPARATION 15

2-(4-oxo-6-(trifluoromethyl)benzo[d][1,2,3]triazin-3 (4H)-yl)acetic acid

The title compound was prepared in a manner similar to Preparation 1 using 6-(trifluoromethyl)-1H-benzo[d][1,3] oxazine-2,4-dione to give the title compound as a tan solid (153 mg, 65%).

PREPARATION 16

2-(5-methoxy-4-oxobenzo[d][1,2,3]triazin-3(4H)-yl) acetic acid

The title compound was prepared in a manner similar to Preparation 1 using 5-methoxy-1H-benzo[d][1,3]oxazine-2, 4-dione to give the title compound as a tan solid (42 mg, 14%).

PREPARATION 17

2-(6,8-dimethyl-4-oxobenzo[d][1,2,3]triazin-3(4H)-yl)acetic acid

The title compound was prepared in a manner similar to Preparation 1 using 6,8-dimethyl-1H-benzo[d][1,3]oxazine-2,4-dione to give the title compound as a tan solid (185 mg, 76%).

PREPARATION 18

2-(8-fluoro-6-methyl-4-oxobenzo[d][1,2,3]triazin-3 (4H)-yl)acetic acid

The title compound was prepared in a manner similar to Preparation 1 using 8-fluoro-6-methyl-1H-benzo[d][1,3]oxazine-2,4-dione to give the title compound as a grey solid (486 mg, 80%).

PREPARATION 19

2-(2,3-dimethyl-7-oxothieno[2,3-d]pyridazin-6(7H)-yl)acetic acid

To a solution of copper(II) chloride (13.49 g, 100 mmol) and tert-butyl nitrite (10 mL, 50.2 mmol) in EtOH:MeOH (252 mL, 20:1) was added ethyl 2-amino-4,5-dimethylthiophene-3-carboxylate (10 g, 50.2 mmol) at RT. The reaction mixture was allowed to stir at RT for 2 h. The resulting mixture was poured into water and extracted with EtOAc (3×). The organic layers were dried, filtered and concentrated. Purification by flash column chromatography eluting with hexanes in EtOAc (100:1-50:1) to give ethyl 4,5-dimethylthiophene-3-carboxylate (8 g, 87%) as an oil.

To a stirred solution of THF (200 mL) was added LiAlH$_4$ (7.42 g, 195 mmol) portion-wise at 0° C. Then, ethyl 4,5-dimethylthiophene-3-carboxylate (12 g, 65.1 mmol) was added to the suspension. The reaction mixture was allowed to stir at RT for 16 h. After completion of the reaction, water (8 mL) was added drop-wise to the mixture, followed by 15% NaOH solution (8 mL) and additional water (24 mL). Filtration, then purification by flash column chromatography eluting in hexanes in EtOAc (50:1-30:1) provided (4,5-dimethylthiophen-3-yl) methanol as an oil (8.0 g, 86%).

To a solution of (4,5-dimethylthiophen-3-yl)methanol (4 g, 25.3 mmol) in THF (60 mL) was added NBS (4.51 g, 25.3 mmol) at RT. The mixture was stirred at RT for 1 h then partitioned between K$_2$CO$_3$ (aq) and EtOAc. The organic layer was dried, filtered and concentrated to give (2-bromo-4,5-dimethylthiophen-3-yl)methanol as oil, which was used without further purification (5.2 g, 93%).

To a solution of (2-bromo-4,5-dimethylthiophen-3-yl) methanol (6 g, 27.1 mol) in MeOH (100 mL) was added PdCl$_2$(dppf) (3.97 g, 5.43 mmol) and TEA (18.9 mL, 136 mmol) at RT. The mixture was stirred at 80° C. under CO atmosphere (50 psi) for 48 h. The reaction mixture was diluted with MeOH, filtered and concentrated to give the crude product, which was purified by column eluting with hexanes in EtOAc (10:1-5:1) to give methyl 3-(hydroxymethyl)-4,5-dimethylthiophene-2-carboxylate as a white solid (4 g, 74%).

To a solution of methyl 3-(hydroxymethyl)-4,5-dimethylthiophene-2-carboxylate (2.8 g, 13.98 mmol) in DCM (40 mL) was added manganese(IV) oxide (12.16 g, 140 mmol) at RT. The reaction mixture was allowed to stir at 40° C. for 16 h. The mixture was diluted with DCM, filtered, and concentrated to provide methyl 3-formyl-4,5-dimethylthiophene-2-carboxylate as a solid (1.6 g, 8.07 mmol, 58%) which was used without further purification.

To a solution of methyl 3-formyl-4,5-dimethylthiophene-2-carboxylate (2.8 g, 14.12 mmol) in EtOH (5 mL) was added 85%-hydrazine hydrate (1.6 mL, 28.2 mol) at RT. The reaction mixture was allowed to stir at 80° C. for 4 h then cooled to RT. Filtration provided 2,3-dimethylthieno[2,3-d] pyridazin-7(6H)-one as a white solid (1.2 g, 47%).

To a suspension of 2,3-dimethylthieno[2,3-d]pyridazin-7 (6H)-one (1.7 g, 9.43 mmol) and K$_2$CO$_3$ (2.61 g, 18.87 mmol) in MeCN (50 mL) was added ethyl 2-bromoacetate (1.0 mL, 9.43 mmol) at RT. The mixture was heated at 80° C. for 16 h. The mixture was poured into water and extracted with EtOAc. The organic layer was dried, filtered and concentrated to give the crude product, which was purified by flash chromatography eluting with hexanes in EtOAc (10:1-5:1) to provide ethyl 2-(2,3-dimethyl-7-oxothieno [2,3-d]pyridazin-6(7H)-yl)acetate (1.5 g, 60% yield) as a white solid.

To a solution of ethyl 2-(2,3-dimethyl-7-oxothieno[2,3-d]pyridazin-6(7H)-yl)acetate (1.5 g, 5.63 mmol) in MeOH (30 mL) was added aq sodium hydroxide (7 mL) at RT. The mixture was allowed to stir at RT for 2 h then solvent was removed and the residue was diluted with water and acidified to pH=2-3 with HCl (4M). Filtration provided the title compound as a white solid (1.2 g, 89%).

PREPARATION 20

(S)-1-(2-fluoro-4-(trifluoromethoxy)phenyl)ethanamine n-Butyl lithium (6.17 mL, 9.87 mmol) was added drop-wise at −78° C. to a solution of 1-bromo-2-fluoro-4-(trifluoromethoxy)benzene (2.13 g, 8.22 mmol) in diethyl ether (16.5 mL). The reaction was stirred for 30 minutes before drop-wise addition of N-methoxy-N-methylacetamide (1.272 g, 12.34 mmol). The reaction was stirred for 5 minutes at −78° C. then warmed to room temperature and stirred for 30 minutes. The solution was quenched with saturated NH$_4$Cl, extracted with EtOAc, dried with Na$_2$SO$_4$, filtered, and concentrated under reduced pressure. Purification by flash silica gel chromatography, eluting with 10% EtOAc in heptanes provided 1-(2-fluoro-4-(trifluoromethoxy)phenyl)ethanone as a clear oil (1.118 g, 61%).

1-(2-Fluoro-4-(trifluoromethoxy)phenyl)ethanone (500 mg, 2.251 mmol) was added to a solution of (S)-2-methylpropane-2-sulfinamide (227 mg, 1.876 mmol) and tetraethoxytitanium (1007 mg, 3.75 mmol, 85%) in THF (3.8 mL) at RT. The solution was stirred at 75° C. for 6 hrs and cooled to RT. The solution was then cooled to −60° C. in an ice bath and added drop-wise to a suspension of NaBH$_4$ (284 mg, 7.50 mmol) in THF (2 mL) at −60° C. The mixture was warmed to 0° C. in an ice bath, then methanol (1 mL) was added drop-wise until gas evolution no longer occurred. The solution was allowed to warm to RT and added to an equal volume of saturated NaCl solution. The precipitate was filtered off through Celite™ and the wet cake was rinsed with EtOAc. Saturated NaCl solution was added to the filtrate and the solution was extracted with EtOAc (3×50 mL). The combined organic fractions were dried over anhydrous MgSO$_4$ then concentrated under reduced pressure. Purification by flash silica gel chromatography, eluting with 40-80% EtOAc in heptanes provided (S)-N—((S)-1-(2-fluoro-4-(trifluoromethoxy)phenyl)ethyl)-2-methylpropane-2-sulfinamide as a clear oil (304 mg, 50%).

To a flask containing (S)-N—((S)-1-(2-fluoro-4-(trifluoromethoxy)phenyl)ethyl)-2-methylpropane-2-sulfinamide (350 mg, 1.069 mmol) was added HCl (1.337 mL, 5.35 mmol, 4 M in dioxane) and methanol (2 mL). The mixture was stirred at RT for 30 min then concentrated under reduced pressure to provide the title compound as its HCl salt (245 mg, 88%) as an off-white solid.

PREPARATION 21

(S)-1-(4-chloro-2-methoxyphenyl)propan-2-amine

A solution of 1-(4-chloro-2-methoxyphenyl)propan-2-one (2.7 g, 13.59 mmol), (S)-2-methylpropane-2-sulfinamide (4.28 g, 35.3 mmol) and tetraethoxytitanium (4.0 g, 17.65 mmol) in THF (120 mL) was stirred at 70° C. for 12 h. The reaction mixture was quenched with sat. NaHCO$_3$ (50 mL) and filtered over a pad of Celite™. The filtrate was concentrated and diluted with H$_2$O (50 mL) and extracted with EtOAc (2×50 mL). The organic layer was dried over Na$_2$SO$_4$ and concentrated under reduced pressure. Purification by flash column chromatography, eluting with petroleum ether in EtOAc (100:1 to 10:1) provided (S,Z)—N-(1-(4-chloro-2-methoxyphenyl)propan-2-ylidene)-2-methylpropane-2-sulfinamide (2.8 g, 68%) as an oil.

To a solution of (S,Z)—N-(1-(4-chloro-2-methoxyphenyl)propan-2-ylidene)-2-methylpropane-2-sulfinamide (3.3 g, 10.93 mmol) in THF (20 mL) was added NaBH$_4$ (0.620 g, 16.40 mmol) at 0° C. The mixture was allowed to warm to RT and stirred for 2 h. The reaction mixture was diluted with H$_2$O (20 mL) and extracted with EtOAc (2×20 mL). The organic layer was dried over Na$_2$SO$_4$ and concentrated to give the crude product. Purification by flash column chromatography, eluting with petroleum ether in EtOAc (100:1 to 10:1) provided (S)-N—((R)-1-(4-chloro-2-methoxyphenyl)propan-2-yl)-2-methylpropane-2-sulfinamide as an oil (430 mg, 13% yield).

To a solution of (S)-N—((S)-1-(4-chloro-2-methoxyphenyl) propan-2-yl)-2-methylpropane-2-sulfinamide (1.6 g, 5.27 mmol) in MeOH (10 mL) was added hydrogen chloride (10.5 mL, 42.1 mmol, 4 M in MeOH) at 0° C., then the mixture was allowed to warm to RT for 30 min. The resulting solid was collected by filtration to afford the title compound as its HCl salt (1.2 g, 97%) as a white solid.

PREPARATION 22

(S)-1-(2-chloro-4-methoxyphenyl)propan-2-amine

To a solution of 1-(2-chloro-4-methoxyphenyl)propan-2-one (4 g, 20.14 mmol) in THF (160 mL) was added (S)-2-methylpropane-2-sulfinamide (7.32 g, 60.4 mmol) and tetraethoxytitanium (6.89 g, 30.2 mmol), and the resulting mixture was stirred at 70° C. for 12 h. The reaction mixture was poured into water, and extracted with EtOAc (3×). The combined organic layers was dried over anhydrous Na$_2$SO$_4$ and concentrated under reduced pressure. Purification by flash column chromatography, eluting with petroleum ether in EtOAc (from 10:1 to 2:1) provided (R,Z)—N-(1-(2-chloro-4-methoxyphenyl)propan-2-ylidene)-2-methylpropane-2-sulfinamide as a yellow oil (4.4 g, 72%).

To a solution of (S,Z)—N-(1-(2-chloro-4-methoxyphenyl)propan-2-ylidene)-2-methylpropane-2-sulfinamide (1.0 g, 3.31 mmol) in THF (20 mL) was added NaBH$_4$ (0.188 g, 4.97 mmol) at −78° C. The reaction was allowed to warm to RT and stirred for 12 h. The reaction mixture was diluted with H$_2$O (40 mL) and extracted with EtOAc (2×30 mL). The organic layer was dried over Na$_2$SO$_4$ and concentrated. Purification by flash column chromatography eluting with petroleum ether in EtOAc (20:1 to 1:1) provided (S)-N—((S)-1-(2-chloro-4-methoxyphenyl)propan-2-yl)-2-methylpropane-2-sulfinamide as a white solid (560 mg, 56% yield).

To a solution of (S)-N—((S)-1-(2-chloro-4-methoxyphenyl)propan-2-yl)-2-methylpropane-2-sulfinamide (470 mg, 1.547 mmol) in MeOH (10 mL) was added hydrogen chloride (3.1 mL, 12.37 mmol, 4 M) at 0° C., and the mixture was allowed to warm to RT for 30 min. The resulting solid was collected by filtration to afford the title compound as its HCl salt (360 mg, 99% yield) as a white solid.

PREPARATION 23

(S)-N-(1-(2-chloro-4-methoxyphenyl)propan-2-yl)-2-(2,3-dimethyl-7-oxothieno[2,3-d]pyridazin-6(7H)-yl)acetamide The title compound was prepared in a manner similar to Preparation 2 using 2-(2,3-dimethyl-7-oxothieno[2,3-d]pyridazin-6(7H)-yl)acetic acid and (S)-1-(2-chloro-4-methoxyphenyl)propan-2-amine, HCl to give the title compound as a white solid (26.7 mg, 76%). $^1$H NMR (500 MHz, DMSO-d$_6$) δ ppm 1.04 (d, J=6.8 Hz, 3 H), 2.31 (s, 3 H), 2.52 (s, 3 H), 2.70-2.80 (m, 2 H), 3.75 (s, 3 H), 4.01 (dt, J=14.4, 7.0 Hz, 1 H), 4.64-4.74 (m, 2 H), 6.86 (dd, J=8.5, 2.7 Hz, 1 H), 6.96-7.00 (m, 1 H), 7.23 (d, J=8.8 Hz, 1 H), 8.08 (d, J=8.3 Hz, 1 H), 8.32-8.36 (m, 1 H); ESI-MS m/z [M, M+2]$^+$ 420.2, 422.1.

PREPARATION 24

(S)-N-(1-(2-chloro-4-hydroxyphenyl)propan-2-yl)-2-(2,3-dimethyl-7-oxothieno[2,3-d]pyridazin-6(7H)-yl)acetamide To a 0° C. solution of (S)-N-(1-(2-chloro-4-methoxyphenyl)propan-2-yl)-2-(2,3-dimethyl-7-oxothieno[2,3-d]pyridazin-6(7H)-yl)acetamide (200 mg, 0.476 mmol) in DCM (4.8 mL) was added BBr$_3$ (2.3 mL, 2.381 mmol, 1 M in DCM). After stirring for 10 min, the ice bath was removed and stirring continued at RT for 1 h. Saturated NaHCO$_3$ (5 mL) was added to the reaction mixture and stirring continued for 30 min. The organic layer was separated, washed with brine, dried over MgSO$_4$, filtered and concentrated under reduced pressure. Purification by flash column chromatography, eluting in 70-100% EtOAc in heptanes provided the title compound as an off-white solid (20 mg, 10%). $^1$H NMR (500 MHz, DMSO-d6) δ ppm 1.03 (d, J=6.8 Hz, 3 H), 2.31 (s, 3 H), 2.52 (d, J=1.0 Hz, 3 H), 2.62-2.78 (m, 2 H), 3.93-4.04 (m, 1 H), 4.64-4.76 (m, 2 H), 6.67 (dd, J=8.3, 2.4 Hz, 1 H), 6.78 (d, J=2.4 Hz, 1 H), 7.10 (d, J=8.3 Hz, 1 H), 8.06 (d, J=7.8 Hz, 1 H), 8.34 (s, 1 H), 8.57-8.59 (m, 1 H), 9.67 (s, 1 H); ESI-MS m/z [M+H]$^+$ 406.1. The title compound can be readily reacted with $^3$H$_3$Cl or other like reagents to give (S)-N-(1-(2-chloro-4-[$^3$H]$_3$methoxyphenyl) propan-2-yl)-2-(2,3-dimethyl-7-oxothieno[2,3-d]pyridazin-6(7H)-yl)acetamide.

PREPARATION 25

(S)-1-(4-(trifluoromethoxy)phenyl)propan-1-amine hydrochloride

To a mixture of 4-(trifluoromethoxy)benzaldehyde (2 mL, 14.0 mmol) in DCM was added (S)-2-methylpropane-2-sulfinamide (2.55 g, 21.0 mmol) and copper(II) sulfate (3.35 g, 21.0 mmol). The solution was stirred at 75° C. for 18 hours. Water, DCM, and Celite™ were added to the mixture. After stirring for 10 min, the mixture was filtered through Celite™ and the filter-cake was washed with DCM. The combined filtrate was concentrated under reduced pressure and the residue was purified by flash chromatography (5-10% EtOAc: Heptanes) to give (S,E)-2-methyl-N-(4-(trifluoromethoxy)benzylidene) propane-2-sulfinamide as a colorless oil (3.0 g, 73%).

Combined (S,E)-2-methyl-N-(4-(trifluoromethoxy)benzylidene) propane-2-sulfinamide (1 g, 3.4 mmol) in THF (10 mL) and cooled to −78° C. under nitrogen. Ethylmagnesium chloride (8.5 mL, 8.5 mmol) was added dropwise. After stirring at −78° C. for 1 hour, saturated ammonium chloride solution was added and the mixture was allowed to warm to 0° C. before extraction with EtOAc (3×20 mL). The combined organic layers were dried over MgSO$_4$, filtered and concentrated. Purification by flash chromatography provided (S)-2-methyl-N—((S)-1-(4-(trifluoromethoxy)phenyl) propyl)propane-2-sulfinamide as an off-white solid (740 mg, 67%).

To a solution of (S)-2-methyl-N—((S)-1-(4-(trifluoromethoxy)phenyl) propyl)propane-2-sulfinamide (740 mg, 2.3 mmol) in MeOH (2 mL) was added hydrogen chloride (0.572 mL, 2.3 mmol). The reaction was stirred at RT for 18 h. Solvent was removed under reduced pressure to provide the title compound (580 mg, 99%).

PREPARATION OF 26

(S)-1-(4-(trifluoromethyl)phenyl)propan-1-amine hydrochloride

The title compound was prepared in a manner similar to Preparation 25 using 4-(trifluoromethyl)benzaldehyde to give the title compound as an off-white solid (570 mg, 99%).

EXAMPLE 1

(S)-2-(4-oxobenzo[d][1,2,3]triazin-3(4H)-yl)-N-(1-phenylethyl)acetamide

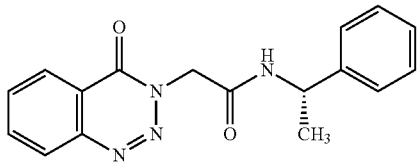 [SMILES: C[C@H](NC(=O)Cn1nnc2ccccc2c1=O)c1ccccc1]

To a vial containing 2-(4-oxobenzo[d][1,2,3]triazin-3 (4H)-yl)acetic acid (15 mg, 0.073 mmol), HOBT (16 mg, 0.102 mmol) and EDC (21 mg, 0.110 mmol) was added DMF (244 μL). After stirring at RT for 5 min, (S)-1-phenylethanamine (11 μL, 0.088 mmol) and DIPEA (64 μL, 0.366 mmol) were added. The reaction mixture was allowed to stir at RT for 1 h then concentrated under reduced pressure. Purification by flash silica gel chromatography, eluting with 0-70% EtOAc in heptanes provided the title compound as a white solid (3.8 mg, 17% yield). $^1$H NMR (500 MHz, DMSO-d$_6$) δ ppm 1.39 (d, J=6.8 Hz, 3 H), 4.91-4.99 (m, 1 H), 5.08 (s, 2 H), 7.22-7.26 (m, 1 H), 7.31-7.38 (m, 4 H), 7.92-7.99 (m, 1 H), 8.12 (td, J=7.8, 1.5 Hz, 1 H), 8.21-8.28 (m, 2 H), 8.80 (d, J=7.8 Hz, 1 H); ESI-MS m/z [M+H]$^+$ 309.9.

EXAMPLE 2

(S)-2-(4-oxobenzo[d][1,2,3]triazin-3(4H)-yl)-N-(1-(4-(trifluoromethoxy)phenyl)ethyl)acetamide

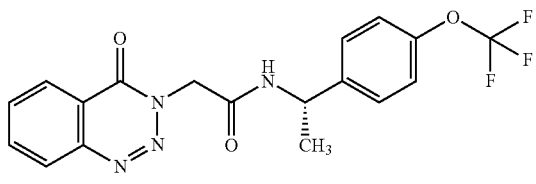 [SMILES: C[C@H](NC(=O)Cn1nnc2ccccc2c1=O)c1ccc(OC(F)(F)F)cc1]

To a vial containing 2-(4-oxobenzo[d][1,2,3]triazin-3 (4H)-yl)acetic acid (15 mg, 0.073 mmol), HOBT (15 mg, 0.095 mmol) and EDC (21 mg, 0.110 mmol) was added DMF (244 μL). After stirring at RT for 5 min, (S)-1-(4-(trifluoromethoxy)phenyl)ethanamine (18 mg, 0.088 mmol) and DIPEA (64, 0.366 mmol) were added. The reaction mixture was allowed to stir at RT for 1 h then water was added (5 mL). The solid was filtered off and washed with water to yield the title compound as a white solid (20 mg, 71% yield). $^1$H NMR (500 MHz, DMSO-d$_6$) δ ppm 1.40 (d, J=6.8 Hz, 3 H), 4.98 (quin, J=7.1 Hz, 1 H), 5.09 (s, 2 H), 7.33 (d, J=7.8 Hz, 2 H), 7.44-7.49 (m, 2 H), 7.93-7.98 (m, 1 H), 8.09-8.15 (m, 1 H), 8.21-8.29 (m, 2 H), 8.85 (d, J=7.8 Hz, 1 H); ESI-MS m/z [M+H]$^+$ 393.9.

EXAMPLE 3

(S)-2-(5-methoxy-4-oxobenzo[d][1,2,3]triazin-3(4H)-yl)-N-(1-p-tolylethyl)acetamide

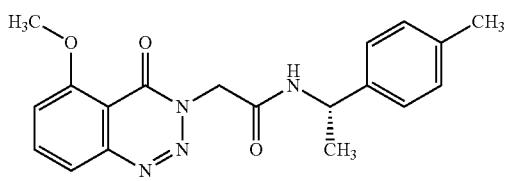 [SMILES: COc1cccc2nnn(CC(=O)N[C@@H](C)c3ccc(C)cc3)c(=O)c12]

To a vial containing 2-(5-methoxy-4-oxobenzo[d][1,2,3]triazin-3(4H)-yl)acetic acid (20 mg, 0.085 mmol), HOBT (17 mg, 0.111 mmol) and EDC (24 mg, 0.128 mmol) was added DMF (283 µL). After stirring at RT for 5 min, (S)-1-(p-tolyl)ethanamine (15 µL, 0.102 mmol) and DIPEA (74 µL, 0.425 mmol) were added. The reaction mixture was allowed to stir at RT for 1 h then water was added (10 mL). The solid was filtered off and washed with water to yield the title compound as a white solid (5 mg, 0.014 mmol, 16% yield). $^1$H NMR (500 MHz, DMSO-$d_6$) δ ppm 1.36 (d, J=7.3 Hz, 3 H), 2.27 (s, 3 H), 3.92 (s, 3 H), 4.85-4.93 (m, 1 H), 4.96 (d, J=1.5 Hz, 2 H), 7.13 (d, J=7.8 Hz, 2 H), 7.21 (d, J=8.3 Hz, 2 H), 7.44 (d, J=7.8 Hz, 1 H), 7.65-7.71 (m, 1 H), 7.96-8.03 (m, 1 H), 8.68 (d, J=7.8 Hz, 1 H); ESI-MS m/z [M+H]$^+$ 354.0.

EXAMPLE 4

(S)-N-(1-(4-bromophenyl)ethyl)-2-(4-oxobenzo[d][1,2,3]triazin-3(4H)-yl)acetamide

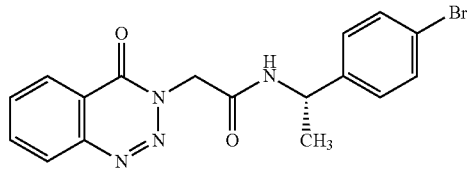 [SMILES: C[C@H](NC(=O)Cn1nnc2ccccc2c1=O)c1ccc(Br)cc1]

To a vial containing 2-(4-oxobenzo[d][1,2,3]triazin-3(4H)-yl)acetic acid (20 mg, 0.097 mmol), HOBT (21 mg, 0.136 mmol) and EDC (28 mg, 0.146 mmol) was added DMF (325 µL). After stirring at RT for 5 min, (S)-1-(4-bromophenyl)ethanamine (17 µL, 0.117 mmol) and DIPEA (85 µL, 0.487 mmol) were added. The reaction mixture was allowed to stir at RT for 18 h. Purification by HPLC Method A provided the title compound as a white solid (12 mg, 33% yield). $^1$H NMR (500 MHz, DMSO-$d_6$) δ ppm 1.37 (d, J=7.3 Hz, 3 H), 4.86-4.95 (m, 1 H), 5.07 (s, 2 H), 7.26-7.32 (m, 2 H), 7.49-7.56 (m, 2 H), 7.92-7.98 (m, 1 H), 8.07-8.15 (m, 1 H), 8.21-8.29 (m, 2 H), 8.83 (d, J=7.8 Hz, 1 H); ESI-MS m/z [M, M+2]$^+$ 386.8, 388.8.

EXAMPLE 5

(S)-2-(4-oxobenzo[d][1,2,3]triazin-3(4H)-yl)-N-(1-p-tolylethyl)acetamide

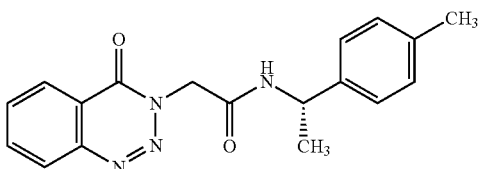

The title compound was prepared in a manner similar to Example 2 using 2-(4-oxobenzo[d][1,2,3]triazin-3(4H)-yl)acetic acid and (S)-1-(p-tolyl)ethanamine to give the title compound as a white solid (21 mg, 88%). $^1$H NMR (500 MHz, DMSO-$d_6$) δ ppm 1.37 (d, J=6.8 Hz, 3 H), 2.27 (s, 3 H), 4.86-4.94 (m, 1 H), 5.01-5.11 (m, 2 H), 7.14 (d, J=7.8 Hz, 2 H), 7.22 (d, J=8.3 Hz, 2 H), 7.95 (ddd, J=8.1, 7.1, 1.5 Hz, 1 H), 8.08-8.16 (m, 1 H), 8.21-8.29 (m, 2 H), 8.74 (d, J=8.3 Hz, 1 H); ESI-MS m/z [M+H]$^+$ 323.0.

EXAMPLE 6

(R)-2-(4-oxobenzo[d][1,2,3]triazin-3(4H)-yl)-N-(1-p-tolylethyl)acetamide

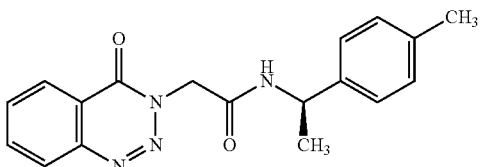

The title compound was prepared in a manner similar to Example 2 using 2-(4-oxobenzo[d][1,2,3]triazin-3(4H)-yl)acetic acid and (R)-1-(p-tolyl)ethanamine to give the title compound as a white solid (39.3 mg, 83%). $^1$H NMR (500 MHz, DMSO-$d_6$) δ ppm 1.37 (d, J=7.3 Hz, 3 H), 2.28 (s, 3 H), 4.86-4.95 (m, 1 H), 5.01-5.11 (m, 2 H), 7.14 (d, J=7.8 Hz, 2 H), 7.22 (d, J=7.8 Hz, 2 H), 7.92-7.98 (m, 1 H), 8.09-8.15 (m, 1 H), 8.21-8.28 (m, 2 H), 8.74 (d, J=7.8 Hz, 1 H); ESI-MS m/z [M+H]$^+$ 323.0.

EXAMPLE 7

(S)-N-(1-(4-methoxyphenyl)ethyl)-2-(4-oxobenzo[d][1,2,3]triazin-3(4H)-yl)acetamide

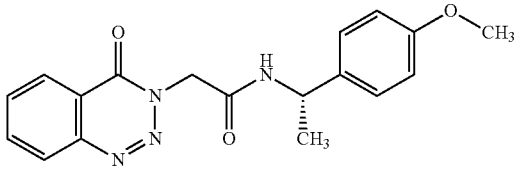 [SMILES: COc1ccc([C@H](C)NC(=O)Cn2nnc3ccccc3c2=O)cc1]

The title compound was prepared in a manner similar to Example 2 using 2-(4-oxobenzo[d][1,2,3]triazin-3(4H)-yl)

acetic acid and (S)-1-(4-methoxyphenyl)ethanamine to give the title compound as a white solid (14 mg, 58%). $^1$H NMR (500 MHz, DMSO-$d_6$) δ ppm 1.37 (d, J=7.3 Hz, 3 H), 3.73 (s, 3 H), 4.90 (quin, J=7.2 Hz, 1 H), 5.01-5.10 (m, 2 H), 6.85-6.92 (m, 2 H), 7.23-7.29 (m, 2 H), 7.92-8.00 (m, 1 H), 8.07-8.16 (m, 1 H), 8.21-8.28 (m, 2 H), 8.72 (d, J=7.8 Hz, 1 H); ESI-MS m/z [M+H]$^+$ 339.0.

EXAMPLE 8

(S)-N-(1-(4-chlorophenyl)ethyl)-2-(4-oxobenzo[d][1,2,3]triazin-3(4H)-yl)acetamide

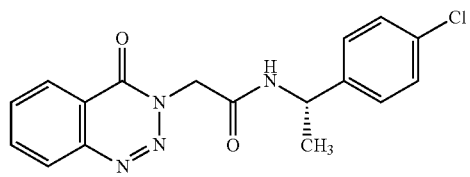

The title compound was prepared in a manner similar to Example 2 using 2-(4-oxobenzo[d][1,2,3]triazin-3(4H)-yl) acetic acid and (S)-1-(4-chlorophenyl)ethanamine to give the title compound as a white solid (10 mg, 40%). $^1$H NMR (500 MHz, DMSO-$d_6$) δ ppm 1.38 (d, J=6.8 Hz, 3 H), 4.93 (quin, J=7.1 Hz, 1 H), 5.07 (s, 2 H), 7.33-7.42 (m, 4 H), 7.92-7.98 (m, 1 H), 8.12 (ddd, J=8.4, 7.2, 1.5 Hz, 1 H), 8.21-8.28 (m, 2 H), 8.83 (d, J=7.8 Hz, 1 H); ESI-MS m/z [M, M+2]$^+$ 342.9, 345.0.

EXAMPLE 9

(S)-N-(1-(2,4-dimethylphenyl)ethyl)-2-(4-oxobenzo[d][1,2,3]triazin-3(4H)-yl)acetamide

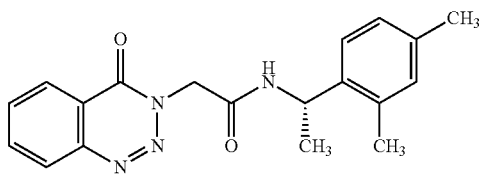 [SMILES: Cc1ccc([C@H](C)NC(=O)Cn2nnc3ccccc3c2=O)c(C)c1]

The title compound was prepared in a manner similar to Example 2 using 2-(4-oxobenzo[d][1,2,3]triazin-3(4H)-yl) acetic acid and (S)-1-(2,4-dimethylphenyl)ethanamine, HCl to give the title compound as a white solid (16.3 mg, 66%). $^1$H NMR (500 MHz, DMSO-$d_6$) δ ppm 1.33 (d, J=6.8 Hz, 3 H), 2.23 (s, 3 H), 2.24 (s, 3 H), 4.98-5.08 (m, 3 H), 6.94 (s, 1 H), 7.01 (d, J=7.8 Hz, 1 H), 7.25 (d, J=7.8 Hz, 1 H), 7.92-7.96 (m, 1 H), 8.08-8.14 (m, 1 H), 8.20-8.27 (m, 2 H), 8.74 (d, J=7.3 Hz, 1 H); ESI-MS m/z [M+H]$^+$ 337.0.

EXAMPLE 10

(S)-2-(4-oxobenzo[d][1,2,3]triazin-3(4H)-yl)-N-(1-o-tolylethyl)acetamide

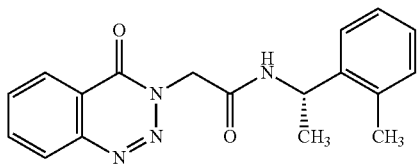 [SMILES: Cc1ccccc1[C@H](C)NC(=O)Cn1nnc2ccccc2c1=O]

The title compound was prepared in a manner similar to Example 2 using 2-(4-oxobenzo[d][1,2,3]triazin-3(4H)-yl) acetic acid and (S)-1-(o-tolyl)ethanamine to give the title compound as a white solid (1 mg, 4%). $^1$H NMR (500 MHz, DMSO-$d_6$) δ ppm 1.36 (d, J=7.3 Hz, 3 H), 2.29 (s, 3 H), 5.05 (d, J=2.4 Hz, 2 H), 5.09 (t, J=7.3 Hz, 1 H), 7.11-7.16 (m, 2 H), 7.19-7.24 (m, 1 H), 7.38 (d, J=7.8 Hz, 1 H), 7.92-7.98 (m, 1 H), 8.11 (td, J=7.6, 1.5 Hz, 1 H), 8.21-8.27 (m, 2 H), 8.80 (d, J=7.3 Hz, 1 H); ESI-MS m/z [M+H]$^+$ 323.0.

EXAMPLE 11

(S)-N-(1-(4-ethoxyphenyl)ethyl)-2-(4-oxobenzo[d][1,2,3]triazin-3 (4H)-yl)acetamide

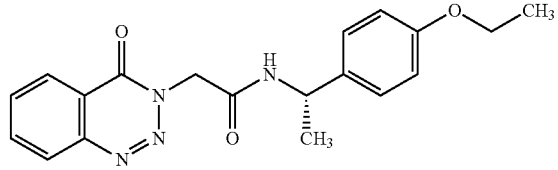 [SMILES: CCOc1ccc([C@H](C)NC(=O)Cn2nnc3ccccc3c2=O)cc1]

The title compound was prepared in a manner similar to Example 2 using 2-(4-oxobenzo[d][1,2,3]triazin-3(4H)-yl) acetic acid and (S)-1-(4-ethoxyphenyl)ethanamine, HCl to give the title compound as a white solid (19.4 mg, 75%). $^1$H NMR (500 MHz, DMSO-$d_6$) δ ppm 1.29-1.33 (m, 3 H), 1.37 (d, J=6.8 Hz, 3 H), 3.96-4.04 (m, 2 H), 4.84-4.93 (m, 1 H), 5.01-5.10 (m, 2 H), 6.85-6.90 (m, 2 H), 7.21-7.28 (m, 2 H), 7.92-7.99 (m, 1 H), 8.08-8.16 (m, 1 H), 8.21-8.29 (m, 2 H), 8.70 (d, J=7.8 Hz, 1 H); ESI-MS m/z [M+H]$^+$ 353.0.

EXAMPLE 12

(S)-N-(1-(2,4-dimethoxyphenyl)ethyl)-2-(4-oxobenzo[d][1,2,3]triazin-3(4H)-yl)acetamide

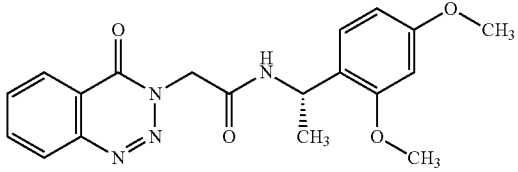 [SMILES: COc1ccc([C@H](C)NC(=O)Cn2nnc3ccccc3c2=O)c(OC)c1]

The title compound was prepared in a manner similar to Example 2 using 2-(4-oxobenzo[d][1,2,3]triazin-3(4H)-yl)

acetic acid and (S)-1-(2,4-dimethoxyphenyl)ethanamine, HCl to give the title compound as a white solid (17.2 mg, 64%). ¹H NMR (500 MHz, DMSO-d$_6$) δ ppm 1.28 (d, J=6.8 Hz, 3 H), 3.75 (s, 3 H), 3.77 (s, 3 H), 5.06 (s, 2 H), 5.14 (quin, J=7.3 Hz, 1 H), 6.49-6.53 (m, 2 H), 6.49-6.52 (m, 1 H), 6.52 (s, 2 H), 7.22 (d, J=7.8 Hz, 1 H), 7.95 (td, J=7.6, 1.5 Hz, 1 H), 8.11 (ddd, J=8.4, 7.2, 1.5 Hz, 1 H), 8.21-8.28 (m, 2 H), 8.62 (d, J=8.3 Hz, 1 H); ESI-MS m/z [M+Na]$^+$ 390.9.

EXAMPLE 13

(S)-2-(4-oxobenzo[d][1,2,3]triazin-3(4H)-yl)-N-(1-(4-(trifluoromethyl)phenyl)ethyl)acetamide

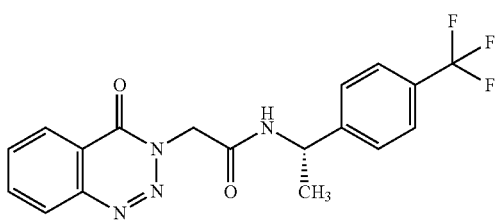 [SMILES: C[C@H](NC(=O)Cn1nnc2ccccc2c1=O)c1ccc(C(F)(F)F)cc1]

The title compound was prepared in a manner similar to Example 2 using 2-(4-oxobenzo[d][1,2,3]triazin-3(4H)-yl)acetic acid and (S)-1-(4-(trifluoromethyl)phenyl)ethanamine to give the title compound as a white solid (81 mg, 88%). ¹H NMR (500 MHz, DMSO-d$_6$) δ ppm 1.40-1.43 (m, 3 H), 5.01 (quin, J=7.2 Hz, 1 H), 5.10 (s, 2 H), 7.56 (d, J=8.3 Hz, 2 H), 7.70 (d, J=8.3 Hz, 2 H), 7.95 (ddd, J=8.1, 7.1, 1.5 Hz, 1 H), 8.10-8.14 (m, 1 H), 8.21-8.28 (m, 2 H), 8.91 (d, J=7.3 Hz, 1 H); ESI-MS m/z [M+Na]$^+$ 399.3.

EXAMPLE 14

(S)-2-(6-fluoro-4-oxobenzo[d][1,2,3]triazin-3(4H)-yl)-N-(1-p-tolylethyl)acetamide

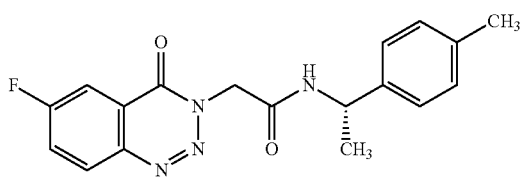 [SMILES: Cc1ccc([C@H](C)NC(=O)Cn2nnc3ccc(F)cc3c2=O)cc1]

The title compound was prepared in a manner similar to Example 2 using 2-(6-fluoro-4-oxobenzo[d][1,2,3]triazin-3(4H)-yl)acetic acid and (S)-1-(p-tolyl)ethanamine to give the title compound as a white solid (23.4 mg, 77%). ¹H NMR (500 MHz, DMSO-d$_6$) δ ppm 1.36 (d, J=7.3 Hz, 3 H), 2.27 (s, 3 H), 4.90 (quin, J=7.2 Hz, 1 H), 5.06 (s, 2 H), 7.10-7.24 (m, 4 H), 7.96-8.03 (m, 2 H), 8.33-8.39 (m, 1 H), 8.73 (d, J=7.8 Hz, 1 H); ESI-MS m/z [M+H]$^+$ 341.0.

EXAMPLE 15

(S)-2-(6-fluoro-4-oxobenzo[d][1,2,3]triazin-3(4H)-yl)-N-(1-(4-methoxyphenyl)ethyl)acetamide

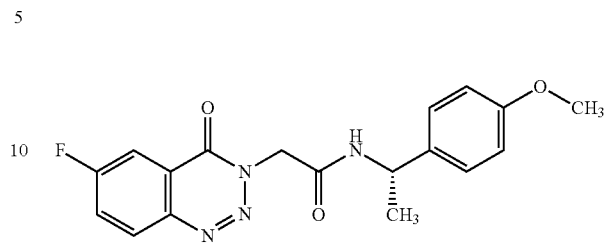

The title compound was prepared in a manner similar to Example 2 using 2-(6-fluoro-4-oxobenzo[d][1,2,3]triazin-3(4H)-yl)acetic acid and (S)-1-(4-methoxyphenyl)ethanamine to give the title compound as a white solid (18.6 mg, 58%). ¹H NMR (500 MHz, DMSO-d$_6$) δ ppm 1.36 (d, J=6.8 Hz, 3 H), 3.73 (s, 3 H), 4.90 (quin, J=7.1 Hz, 1 H), 5.05 (d, J=1.0 Hz, 2 H), 6.86-6.91 (m, 2 H), 7.22-7.29 (m, 2 H), 7.96-8.03 (m, 2 H), 8.33-8.39 (m, 1 H), 8.70 (d, J=7.8 Hz, 1 H); ESI-MS m/z [M+H]$^+$ 357.0.

EXAMPLE 16

(S)-2-(8-fluoro-4-oxobenzo[d][1,2,3]triazin-3(4H)-yl)-N-(1-p-tolylethyl)acetamide

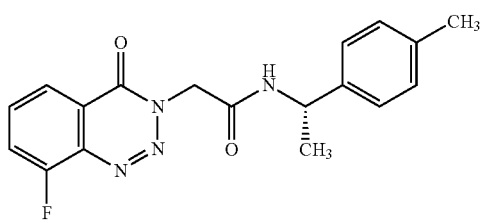 [SMILES: Cc1ccc([C@H](C)NC(=O)Cn2nnc3c(F)cccc3c2=O)cc1]

The title compound was prepared in a manner similar to Example 2 using 2-(8-fluoro-4-oxobenzo[d][1,2,3]triazin-3(4H)-yl)acetic acid and (S)-1-(p-tolyl)ethanamine to give the title compound as an off-white solid (13.0 mg, 43%). ¹H NMR (500 MHz, DMSO-d$_6$) δ ppm 1.36 (d, J=7.3 Hz, 3 H), 2.27 (s, 3 H), 4.90 (quin, J=7.1 Hz, 1 H), 5.06-5.09 (m, 2 H), 7.13 (d, J=7.8 Hz, 2 H), 7.19-7.23 (m, 2 H), 7.91-8.03 (m, 2 H), 8.04-8.09 (m, 1 H), 8.73 (d, J=8.3 Hz, 1 H); ESI-MS m/z [M+H]$^+$ 341.0.

EXAMPLE 17

(S)-2-(8-fluoro-4-oxobenzo[d][1,2,3]triazin-3(4H)-yl)-N-(1-(4-methoxyphenyl)ethyl)acetamide

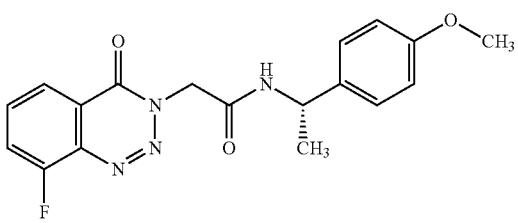

The title compound was prepared in a manner similar to Example 2 using 2-(8-fluoro-4-oxobenzo[d][1,2,3]triazin-3 (4H)-yl)acetic acid and (S)-1-(4-methoxyphenyl)ethanamine to give the title compound as an off-white solid (22.4 mg, 70%). ¹H NMR (500 MHz, DMSO-d₆) δ ppm 1.36 (d, J=6.8 Hz, 3 H), 3.73 (s, 3 H), 4.90 (quin, J=7.2 Hz, 1 H), 5.07 (s, 2 H), 6.86-6.91 (m, 2 H), 7.23-7.27 (m, 2 H), 7.92-8.03 (m, 2 H), 8.06 (dd, J=7.8, 1.5 Hz, 1 H), 8.70 (d, J=7.8 Hz, 1 H); ESI-MS m/z [M+H]⁺ 357.0.

EXAMPLE 18

(S)-2-(6-methoxy-4-oxobenzo[d][1,2,3]triazin-3 (4H)-yl)-N-(1-p-tolylethyl)acetamide

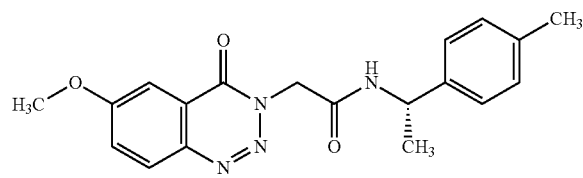

The title compound was prepared in a manner similar to Example 2 using 2-(6-methoxy-4-oxobenzo[d][1,2,3]triazin-3(4H)-yl)acetic acid and (S)-1-(p-tolyl)ethanamine to give the title compound as an off-white solid (18.1 mg, 60%). ¹H NMR (500 MHz, DMSO-d₆) δ ppm 1.32-1.40 (m, 3 H), 2.27 (s, 3 H), 3.97 (s, 3 H), 4.90 (quin, J=7.3 Hz, 1 H), 5.03 (d, J=1.5 Hz, 2 H), 7.13 (d, J=7.8 Hz, 2 H), 7.22 (d, J=8.3 Hz, 2 H), 7.58 (d, J=2.4 Hz, 1 H), 7.63-7.68 (m, 1 H), 8.17 (d, J=8.8 Hz, 1 H), 8.71 (d, J=7.8 Hz, 1 H); ESI-MS m/z [M+H]⁺ 353.0.

EXAMPLE 19

(S)-2-(6-chloro-4-oxobenzo[d][1,2,3]triazin-3 (4H)-yl)-N-(1-p-tolylethyl)acetamide

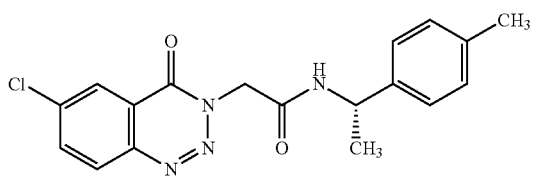 [SMILES: Cc1ccc([C@H](C)NC(=O)Cn2nnc3ccc(Cl)cc3c2=O)cc1]

The title compound was prepared in a manner similar to Example 2 using 2-(6-chloro-4-oxobenzo[d][1,2,3]triazin-3 (4H)-yl)acetic acid and (S)-1-(p-tolyl)ethanamine to give the title compound as an off-white solid (15.6 mg, 52%). ¹H NMR (500 MHz, DMSO-d₆) δ ppm 1.36 (d, J=7.3 Hz, 3 H), 2.25-2.28 (m, 3 H), 4.86-4.94 (m, 1 H), 5.06 (s, 2 H), 7.13 (d, J=7.8 Hz, 2 H), 7.19-7.24 (m, 2 H), 8.13-8.18 (m, 1 H), 8.23 (d, J=2.4 Hz, 1 H), 8.27 (d, J=8.3 Hz, 1 H), 8.73 (d, J=7.8 Hz, 1 H); ESI-MS m/z [M, M+2]⁺ 357.0, 358.9.

EXAMPLE 20

(S)-2-(6-chloro-4-oxobenzo[d][1,2,3]triazin-3(4H)-yl)-N-(1-(4-methoxyphenyl)ethyl)acetamide

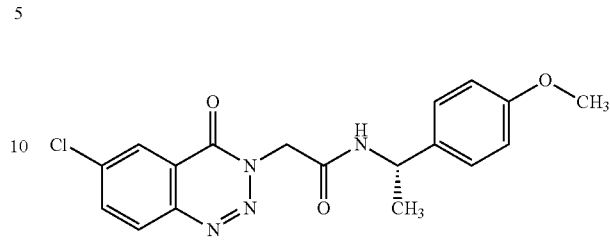

The title compound was prepared in a manner similar to Example 2 using 2-(6-chloro-4-oxobenzo[d][1,2,3]triazin-3 (4H)-yl)acetic acid and (S)-1-(4-methoxyphenyl)ethanamine to give the title compound as an off-white solid (20.4 mg, 66%). ¹H NMR (500 MHz, DMSO-d₆) δ ppm 1.36 (d, J=6.8 Hz, 3 H), 3.70-3.75 (m, 3 H), 4.90 (quin, J=7.2 Hz, 1 H), 5.05 (d, J=1.0 Hz, 2 H), 6.86-6.91 (m, 2 H), 7.22-7.27 (m, 2 H), 8.13-8.18 (m, 1 H), 8.23 (d, J=2.4 Hz, 1 H), 8.27 (d, J=8.8 Hz, 1 H), 8.70 (d, J=7.8 Hz, 1 H); ESI-MS m/z [M, M+2]⁺ 372.4, 374.9.

EXAMPLE 21

(S)-2-(7-chloro-4-oxobenzo[d][1,2,3]triazin-3(4H)-yl)-N-(1-p-tolylethyl)acetamide

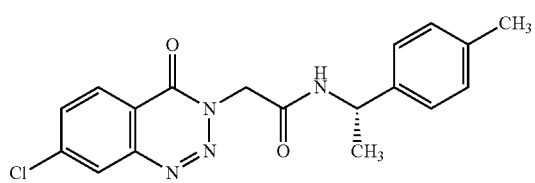 [SMILES: Cc1ccc([C@H](C)NC(=O)Cn2nnc3cc(Cl)ccc3c2=O)cc1]

The title compound was prepared in a manner similar to Example 2 using 2-(7-chloro-4-oxobenzo[d][1,2,3]triazin-3 (4H)-yl)acetic acid and (S)-1-(p-tolyl)ethanamine to give the title compound as an white solid (15.3 mg, 51%). ¹H NMR (500 MHz, DMSO-d₆) δ ppm 1.36 (d, J=6.8 Hz, 3 H), 2.27 (s, 3 H), 4.90 (quin, J=7.2 Hz, 1 H), 5.06 (s, 2 H), 7.13 (d, J=7.8 Hz, 2 H), 7.21 (d, J=7.8 Hz, 2 H), 7.98 (dd, J=8.5, 2.2 Hz, 1 H), 8.25 (d, J=8.3 Hz, 1 H), 8.37 (d, J=2.0 Hz, 1 H), 8.73 (d, J=7.8 Hz, 1 H); ESI-MS m/z [M, M+2]⁺ 357.0, 358.9.

EXAMPLE 22

(S)-2-(8-chloro-4-oxobenzo[d][1,2,3]triazin-3(4H)-yl)-N-(1-p-tolylethyl)acetamide

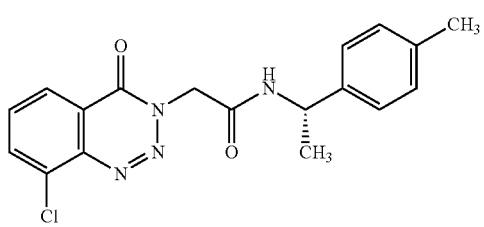 [SMILES: Cc1ccc([C@H](C)NC(=O)Cn2nnc3c(Cl)cccc3c2=O)cc1]

The title compound was prepared in a manner similar to Example 2 using 2-(8-chloro-4-oxobenzo[d][1,2,3]triazin-3(4H)-yl)acetic acid and (S)-1-(p-tolyl)ethanamine to give the title compound as an off-white solid (18.6 mg, 63%). $^1$H NMR (500 MHz, DMSO-$d_6$) δ ppm 1.36 (d, J=6.8 Hz, 3 H), 2.26-2.29 (m, 3 H), 4.91 (quin, J=7.1 Hz, 1 H), 5.07 (s, 2 H), 7.13 (d, J=7.8 Hz, 2 H), 7.19-7.24 (m, 2 H), 7.91 (t, J=7.8 Hz, 1 H), 8.17-8.26 (m, 2 H), 8.73 (d, J=7.8 Hz, 1 H); ESI-MS m/z [M, M+2]$^+$ 357.0, 358.9.

EXAMPLE 23

(S)-2-(8-chloro-4-oxobenzo[d][1,2,3]triazin-3(4H)-yl)-N-(1-(4-methoxyphenyl)ethyl)acetamide

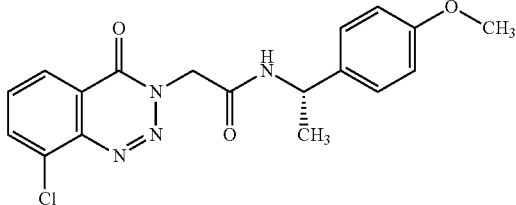 [SMILES: COc1ccc([C@H](C)NC(=O)Cn2nnc3c(Cl)cccc3c2=O)cc1]

The title compound was prepared in a manner similar to Example 2 using 2-(8-chloro-4-oxobenzo[d][1,2,3]triazin-3(4H)-yl)acetic acid and (S)-1-(4-methoxyphenyl)ethanamine to give the title compound as an off-white solid (14.2 mg, 46%). $^1$H NMR (500 MHz, DMSO-$d_6$) δ ppm 1.36 (d, J=6.8 Hz, 3 H), 3.71-3.75 (m, 3 H), 4.90 (quin, J=7.2 Hz, 1 H), 5.07 (s, 2 H), 6.86-6.91 (m, 2 H), 7.22-7.27 (m, 2 H), 7.87-7.94 (m, 1 H), 8.22 (ddd, J=18.4, 7.9, 1.5 Hz, 2 H), 8.70 (d, J=7.8 Hz, 1 H); ESI-MS m/z [M, M+2]$^+$ 372.9, 374.9.

EXAMPLE 24

(S)-2-(8-methyl-4-oxobenzo[d][1,2,3]triazin-3(4H)-yl)-N-(1-p-tolylethyl)acetamide

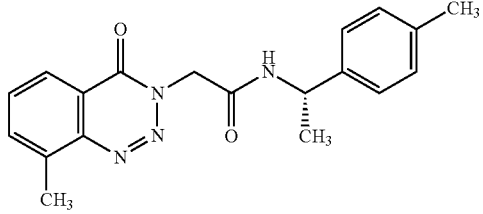 [SMILES: Cc1ccc([C@H](C)NC(=O)Cn2nnc3c(C)cccc3c2=O)cc1]

The title compound was prepared in a manner similar to Example 2 using 2-(8-methyl-4-oxobenzo[d][1,2,3]triazin-3(4H)-yl)acetic acid and (S)-1-(p-tolyl)ethanamine to give the title compound as a white solid (8.0 mg, 26%). $^1$H NMR (500 MHz, DMSO-$d_6$) δ ppm 1.37 (d, J=7.3 Hz, 3 H), 2.27 (s, 3 H), 2.77 (s, 3 H), 4.90 (t, J=7.6 Hz, 1 H), 5.05 (d, J=1.5 Hz, 2 H), 7.13 (d, J=8.3 Hz, 2 H), 7.19-7.24 (m, 2 H), 7.78-7.85 (m, 1 H), 7.91-7.96 (m, 1 H), 8.04-8.10 (m, 1 H), 8.72 (d, J=8.3 Hz, 1 H); ESI-MS m/z [M+H]$^+$ 337.0.

EXAMPLE 25

(S)-N-(1-(4-methoxyphenyl)ethyl)-2-(8-methyl-4-oxobenzo[d][1,2,3]triazin-3 (4H)-yl)acetamide

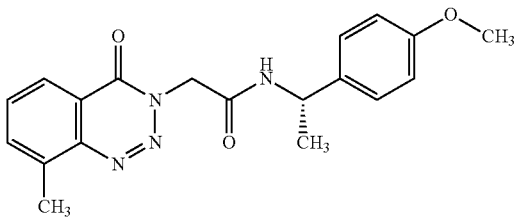 [SMILES: COc1ccc([C@H](C)NC(=O)Cn2nnc3c(C)cccc3c2=O)cc1]

The title compound was prepared in a manner similar to Example 2 using 2-(8-methyl-4-oxobenzo[d][1,2,3]triazin-3(4H)-yl)acetic acid and (S)-1-(4-methoxyphenyl)ethanamine to give the title compound as a white solid (6.0 mg, 19%). $^1$H NMR (500 MHz, DMSO-$d_6$) δ ppm 1.37 (d, J=7.3 Hz, 3 H), 2.77 (s, 3 H), 3.71-3.75 (m, 3 H), 4.90 (quin, J=7.3 Hz, 1 H), 5.04 (d, J=2.4 Hz, 2 H), 6.86-6.92 (m, 2 H), 7.21-7.28 (m, 2 H), 7.78-7.85 (m, 1 H), 7.94 (dt, J=7.1, 1.3 Hz, 1 H), 8.07 (d, J=7.3 Hz, 1 H), 8.70 (d, J=7.8 Hz, 1 H); ESI-MS m/z [M+H]$^+$ 353.0.

EXAMPLE 26

(S)-2-(6,8-dichloro-4-oxobenzo[d][1,2,3]triazin-3 (4H)-yl)-N-(1-p-tolylethyl)acetamide

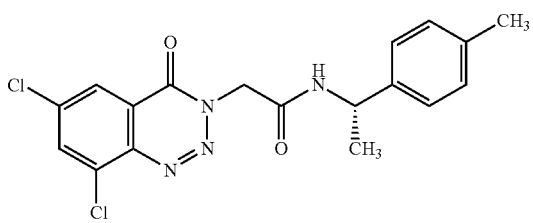 [SMILES: Cc1ccc([C@H](C)NC(=O)Cn2nnc3c(Cl)cc(Cl)cc3c2=O)cc1]

The title compound was prepared in a manner similar to Example 2 using 2-(6,8-dichloro-4-oxobenzo[d][1,2,3]triazin-3(4H)-yl)acetic acid and (S)-1-(p-tolyl)ethanamine to give the title compound as a white solid (12.1 mg, 42%). $^1$H NMR (500 MHz, DMSO-$d_6$) δ ppm 1.36 (d, J=6.8 Hz, 3 H), 2.27 (s, 3 H), 4.86-4.94 (m, 1 H), 5.07 (s, 2 H), 7.13 (d, J=7.8 Hz, 2 H), 7.19-7.23 (m, 2 H), 8.20 (d, J=2.0 Hz, 1 H), 8.44-8.47 (m, 1 H), 8.72 (d, J=7.8 Hz, 1 H); ESI-MS m/z [M, M+2]$^+$ 390.8, 392.9.

EXAMPLE 27

(S)-2-(6,8-dichloro-4-oxobenzo[d][1,2,3]triazin-3 (4H)-yl)-N-(1-(4-methoxyphenyl)ethyl)acetamide

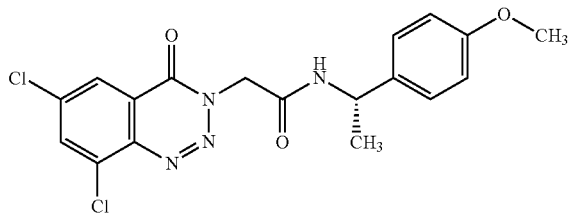 [SMILES: COc1ccc([C@H](C)NC(=O)Cn2nnc3c(Cl)cc(Cl)cc3c2=O)cc1]

The title compound was prepared in a manner similar to Example 2 using 2-(6,8-dichloro-4-oxobenzo[d][1,2,3]triazin-3(4H)-yl)acetic acid and (S)-1-(4-methoxyphenyl)ethanamine to give the title compound as a white solid (16.2 mg, 55%). $^1$H NMR (500 MHz, DMSO-d$_6$) δ ppm 1.36 (d, J=6.8 Hz, 3 H), 3.71-3.75 (m, 3 H), 4.86-4.93 (m, 1 H), 5.07 (d, J=1.0 Hz, 2 H), 6.87-6.91 (m, 2 H), 7.22-7.28 (m, 2 H), 8.18-8.22 (m, 1 H), 8.45 (d, J=2.4 Hz, 1 H), 8.70 (d, J=7.8 Hz, 1 H); ESI-MS m/z [M, M+2]$^+$ 406.8, 408.8.

EXAMPLE 28

(S)-2-(6-methyl-4-oxobenzo[d][1,2,3]triazin-3(4H)-yl)-N-(1-p-tolylethyl)acetamide

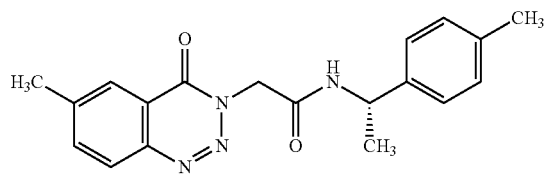

The title compound was prepared in a manner similar to Example 2 using 2-(6-methyl-4-oxobenzo[d][1,2,3]triazin-3(4H)-yl)acetic acid and (S)-1-(p-tolyl)ethanamine to give the title compound as a white solid (9.1 mg, 30%). $^1$H NMR (500 MHz, DMSO-d$_6$) δ ppm 1.36 (d, J=6.8 Hz, 3 H), 2.27 (s, 3 H), 2.55 (s, 3 H), 4.90 (t, J=7.6 Hz, 1 H), 5.04 (d, J=1.5 Hz, 2 H), 7.11-7.16 (m, 2 H), 7.22 (d, J=7.8 Hz, 2 H), 7.92 (dd, J=8.3, 1.5 Hz, 1 H), 8.05 (s, 1 H), 8.12 (d, J=8.3 Hz, 1 H), 8.71 (d, J=7.8 Hz, 1 H); ESI-MS m/z [M+H]$^+$ 337.1.

EXAMPLE 29

(S)-N-(1-(4-methoxyphenyl)ethyl)-2-(6-methyl-4-oxobenzo[d][1,2,3]triazin-3(4H)-yl)acetamide

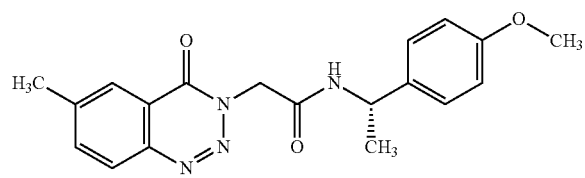

The title compound was prepared in a manner similar to Example 2 using 2-(6-methyl-4-oxobenzo[d][1,2,3]triazin-3(4H)-yl)acetic acid and (S)-1-(4-methoxyphenyl)ethanamine to give the title compound as an off-white solid (7.0 mg, 22%). $^1$H NMR (500 MHz, DMSO-d$_6$) δ ppm 1.36 (d, J=6.8 Hz, 3 H), 2.54-2.57 (m, 3 H), 3.73 (s, 3 H), 4.89 (quin, J=7.2 Hz, 1 H), 5.03 (d, J=2.0 Hz, 2 H), 6.86-6.91 (m, 2 H), 7.23-7.27 (m, 2 H), 7.93 (dd, J=8.3, 1.5 Hz, 1 H), 8.05 (s, 1 H), 8.12 (d, J=8.3 Hz, 1 H), 8.69 (d, J=7.8 Hz, 1 H); ESI-MS m/z [M+H]$^+$ 353.0.

EXAMPLE 30

(S)-2-(8-methoxy-4-oxobenzo[d][1,2,3]triazin-3 (4H)-yl)-N-(1-p-tolylethyl)acetamide

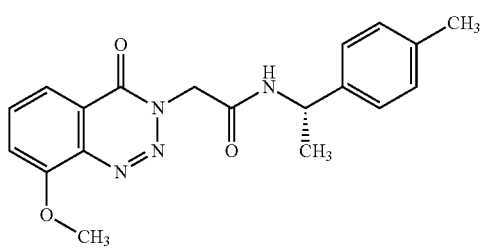 [SMILES: COc1cccc2c(=O)n(CC(=O)N[C@@H](C)c3ccc(C)cc3)nnc12]

The title compound was prepared in a manner similar to Example 2 using 2-(8-methoxy-4-oxobenzo[d][1,2,3]triazin-3(4H)-yl)acetic acid and (S)-1-(p-tolyl)ethanamine to give the title compound as a white solid (12.3 mg, 41%). $^1$H NMR (500 MHz, DMSO-d$_6$) δ ppm 1.36 (d, J=6.8 Hz, 3 H), 2.26-2.28 (m, 3 H), 4.04 (s, 3 H), 4.90 (quin, J=7.2 Hz, 1 H), 5.03 (s, 2 H), 7.13 (d, J=7.8 Hz, 2 H), 7.21 (d, J=8.3 Hz, 2 H), 7.64 (dd, J=8.3, 1.0 Hz, 1 H), 7.72-7.76 (m, 1 H), 7.85-7.90 (m, 1 H), 8.71 (d, J=7.8 Hz, 1 H); ESI-MS m/z [M+H]$^+$ 353.0.

EXAMPLE 31

(S)-2-(8-methoxy-4-oxobenzo[d][1,2,3]triazin-3 (4H)-yl)-N-(1-(4-methoxyphenyl)ethyl)acetamide

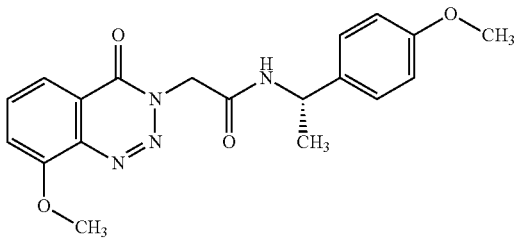 [SMILES: COc1ccc([C@H](C)NC(=O)Cn2nnc3c(OC)cccc3c2=O)cc1]

The title compound was prepared in a manner similar to Example 2 using 2-(8-methoxy-4-oxobenzo[d][1,2,3]triazin-3(4H)-yl)acetic acid and (S)-1-(4-methoxyphenyl)ethanamine to give the title compound as a white solid (11.8 mg, 38%). $^1$H NMR (500 MHz, DMSO-d$_6$) δ ppm 1.36 (d, J=6.8 Hz, 3 H), 3.72-3.74 (m, 3 H), 4.04 (s, 3 H), 4.89 (quin, J=7.2 Hz, 1 H), 4.99-5.05 (m, 2 H), 6.86-6.91 (m, 2 H), 7.21-7.27 (m, 2 H), 7.64 (dd, J=8.3, 1.0 Hz, 1 H), 7.71-7.77 (m, 1 H), 7.84-7.90 (m, 1 H), 8.68 (d, J=7.8 Hz, 1 H); ESI-MS m/z [M+H]$^+$ 369.0.

EXAMPLE 32

(S)-2-(5-fluoro-4-oxobenzo[d][1,2,3]triazin-3(4H)-yl)-N-(1-p-tolylethyl)acetamide

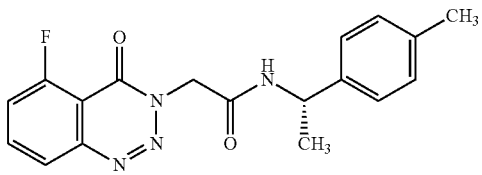 [SMILES: Cc1ccc([C@H](C)NC(=O)Cn2nnc3cccc(F)c3c2=O)cc1]

The title compound was prepared in a manner similar to Example 2 using 2-(5-fluoro-4-oxobenzo[d][1,2,3]triazin-3(4H)-yl)acetic acid and (S)-1-(p-tolyl)ethanamine to give the title compound as a white solid (11.3 mg, 37%). $^1$H NMR (500 MHz, DMSO-$d_6$) δ ppm 1.37 (d, J=6.8 Hz, 3 H), 2.24-2.29 (m, 4 H), 4.87-4.95 (m, 1 H), 5.02 (s, 2 H), 7.11-7.15 (m, 2 H), 7.21 (d, J=8.3 Hz, 2 H), 7.71-7.78 (m, 1 H), 8.03-8.14 (m, 2H), 8.71 (d, J=7.8 Hz, 1H); ESI-MS m/z [M+H]$^+$ 341.0.

EXAMPLE 33

(S)-2-(5-fluoro-4-oxobenzo[d][1,2,3]triazin-3(4H)-yl)-N-(1-(4-methoxyphenyl)ethyl)acetamide

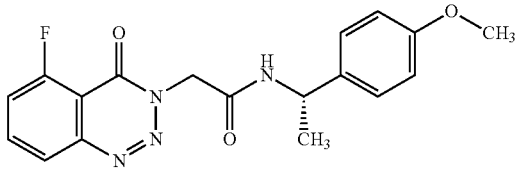 [SMILES: COc1ccc([C@H](C)NC(=O)Cn2nnc3cccc(F)c3c2=O)cc1]

The title compound was prepared in a manner similar to Example 2 using 2-(5-fluoro-4-oxobenzo[d][1,2,3]triazin-3(4H)-yl)acetic acid and (S)-1-(p-tolyl)ethanamine to give the title compound as a white solid (8.4 mg, 26%). $^1$H NMR (500 MHz, DMSO-$d_6$) δ ppm 1.36 (d, J=6.8 Hz, 3 H), 3.71-3.75 (m, 3 H), 4.84-4.95 (m, 1 H), 5.01 (s, 2 H), 6.86-6.92 (m, 2 H), 7.22-7.28 (m, 2 H), 7.71-7.79 (m, 1 H), 8.04-8.08 (m, 1 H), 8.08-8.15 (m, 1 H), 8.69 (d, J=7.8 Hz, 1 H); ESI-MS m/z [M+H]$^+$ 356.9.

EXAMPLE 34

(S)-2-(7-methyl-4-oxobenzo[d][1,2,3]triazin-3(4H)-yl)-N-(1-p-tolylethyl)acetamide

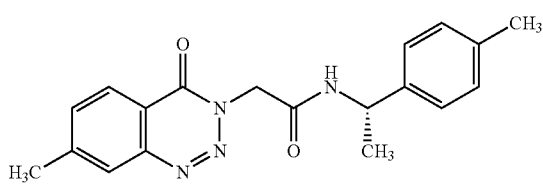

The title compound was prepared in a manner similar to Example 2 using 2-(7-methyl-4-oxobenzo[d][1,2,3]triazin-3(4H)-yl)acetic acid and (S)-1-(p-tolyl)ethanamine to give the title compound as a white solid (28.2 mg, 92%). $^1$H NMR (500 MHz, DMSO-$d_6$) δ ppm 1.36 (d, J=6.8 Hz, 3 H), 2.27 (s, 3 H), 2.57 (s, 3 H), 4.90 (t, J=7.3 Hz, 1 H), 5.04 (d, J=1.0 Hz, 2 H), 7.10-7.16 (m, 2 H), 7.20-7.23 (m, 2 H), 7.77 (d, J=7.8 Hz, 1 H), 8.04 (s, 1 H), 8.13 (d, J=7.8 Hz, 1 H), 8.72 (d, J=7.8 Hz, 1 H); ESI-MS m/z [M+Na]$^+$ 359.0.

EXAMPLE 35

(S)-N-(1-(4-methoxyphenyl)ethyl)-2-(7-methyl-4-oxobenzo[d][1,2,3]triazin-3(4H)-yl)acetamide

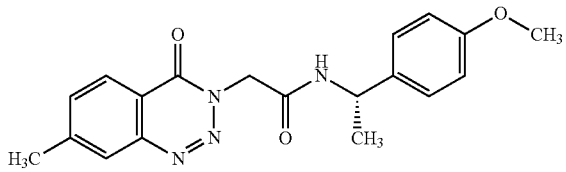

The title compound was prepared in a manner similar to Example 2 using 2-(7-methyl-4-oxobenzo[d][1,2,3]triazin-3(4H)-yl)acetic acid and (S)-1-(4-methoxyphenyl)ethanamine to give the title compound as a white solid (24.1 mg, 75%). $^1$H NMR (500 MHz, DMSO-$d_6$) δ ppm 0.00-0.00 (m, 1 H), 1.36 (d, J=6.8 Hz, 3 H), 2.56-2.59 (m, 3 H), 3.73 (s, 3 H), 4.89 (quin, J=7.2 Hz, 1 H), 5.03 (d, J=2.0 Hz, 2 H), 6.86-6.91 (m, 2 H), 7.23-7.27 (m, 2 H), 7.75-7.80 (m, 1 H), 8.04 (s, 1 H), 8.14 (d, J=8.3 Hz, 1 H), 8.66-8.73 (m, 1 H); ESI-MS m/z [M+H]$^+$ 353.0.

EXAMPLE 36

(S)-2-(7-methoxy-4-oxobenzo[d][1,2,3]triazin-3(4H)-yl)-N-(1-p-tolylethyl)acetamide

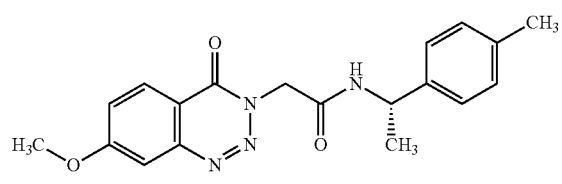

The title compound was prepared in a manner similar to Example 2 using 2-(7-methoxy-4-oxobenzo[d][1,2,3]triazin-3(4H)-yl)acetic acid and (S)-1-(p-tolyl)ethanamine to give the title compound as a white solid (23.3 mg, 78%). $^1$H NMR (500 MHz, DMSO-$d_6$) δ ppm 1.32-1.40 (m, 3 H), 2.27 (s, 3 H), 3.99 (s, 3 H), 4.89 (quin, J=7.3 Hz, 1 H), 5.03 (d, J=1.0 Hz, 2 H), 7.13 (d, J=7.8 Hz, 2 H), 7.22 (d, J=7.8 Hz, 2 H), 7.49 (dd, J=8.8, 2.4 Hz, 1 H), 7.66 (d, J=2.9 Hz, 1 H), 8.14 (d, J=8.8 Hz, 1 H), 8.72 (d, J=8.3 Hz, 1 H); ESI-MS m/z [M+H]$^+$ 353.0.

EXAMPLE 37

(S)-2-(7-methoxy-4-oxobenzo[d][1,2,3]triazin-3 (4H)-yl)-N-(1-(4-methoxyphenyl)ethyl)acetamide

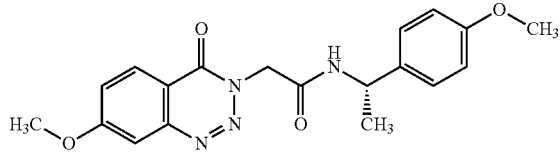

The title compound was prepared in a manner similar to Example 2 using 2-(7-methoxy-4-oxobenzo[d][1,2,3]triazin-3(4H)-yl)acetic acid and (S)-1-(4-methoxyphenyl)ethanamine to give the title compound as a white solid (20.6 mg, 66%). $^1$H NMR (500 MHz, DMSO-$d_6$) δ ppm 1.36 (d, J=7.3 Hz, 3 H), 3.71-3.74 (m, 3 H), 3.99 (s, 3 H), 4.89 (quin, J=7.2 Hz, 1 H), 5.02 (d, J=1.5 Hz, 2 H), 6.86-6.91 (m, 2 H), 7.22-7.27 (m, 2 H), 7.49 (dd, J=8.8, 2.4 Hz, 1 H), 7.66 (d, J=2.4 Hz, 1 H), 8.11-8.18 (m, 1 H), 8.69 (d, J=7.8 Hz, 1 H); ESI-MS m/z [M+H]$^+$ 369.0.

EXAMPLE 38

(S)-2-(5-methoxy-4-oxobenzo[d][1,2,3]triazin-3 (4H)-yl)-N-(1-(4-methoxyphenyl)ethyl)acetamide

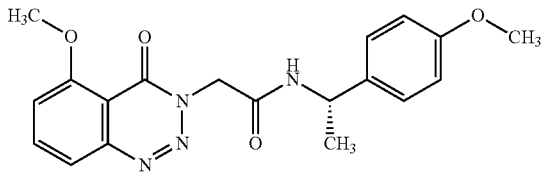

The title compound was prepared in a manner similar to Example 2 using 2-(5-methoxy-4-oxobenzo[d][1,2,3]triazin-3(4H)-yl)acetic acid and (S)-1-(4-methoxyphenyl)ethanamine to give the title compound as a white solid (4.2 mg, 13%). $^1$H NMR (500 MHz, DMSO-$d_6$) δ ppm 1.36 (d, J=6.8 Hz, 3 H), 3.70-3.74 (m, 3 H), 3.92 (s, 3 H), 4.83-4.92 (m, 1 H), 4.95 (d, J=2.0 Hz, 2 H), 6.85-6.91 (m, 2 H), 7.25 (d, J=8.8 Hz, 2 H), 7.44 (d, J=7.8 Hz, 1 H), 7.67-7.71 (m, 1 H), 7.96-8.04 (m, 1 H), 8.65 (d, J=8.3 Hz, 1 H); ESI-MS m/z [M+H]$^+$ 369.0.

EXAMPLE 39

(S)-2-(5-methyl-4-oxobenzo[d][1,2,3]triazin-3 (4H)-yl)-N-(1-p-tolylethyl)acetamide

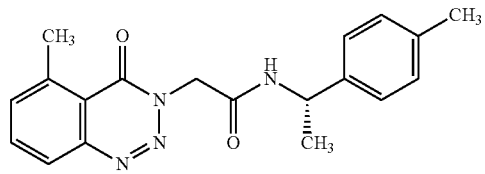 [SMILES: Cc1ccc([C@H](C)NC(=O)Cn2nnc3cccc(C)c3c2=O)cc1]

The title compound was prepared in a manner similar to Example 2 using 2-(5-methyl-4-oxobenzo[d][1,2,3]triazin-3(4H)-yl)acetic acid and (S)-1-(p-tolyl)ethanamine to give the title compound as a white solid (1.2 mg, 4%). $^1$H NMR (500 MHz, DMSO-$d_6$) δ ppm 1.34-1.39 (m, 3 H), 2.26-2.29 (m, 4 H), 2.81 (s, 3 H), 4.85-4.94 (m, 1 H), 5.00 (s, 2 H), 7.13 (d, J=7.8 Hz, 2 H), 7.19-7.25 (m, 2 H), 7.70 (d, J=7.3 Hz, 1 H), 7.91-7.98 (m, 1 H), 8.02 (d, J=8.3 Hz, 1 H), 8.71 (d, J=7.8 Hz, 1 H); ESI-MS m/z [M+Na]$^+$ 359.0.

EXAMPLE 40

(S)-N-(1-(4-methoxyphenyl)ethyl)-2-(5-methyl-4-oxobenzo[d][1,2,3]triazin-3(4H)-yl)acetamide

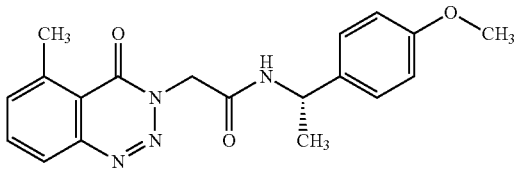 [SMILES: COc1ccc([C@H](C)NC(=O)Cn2nnc3cccc(C)c3c2=O)cc1]

The title compound was prepared in a manner similar to Example 2 using 2-(5-methyl-4-oxobenzo[d][1,2,3]triazin-3(4H)-yl)acetic acid and (S)-1-(4-methoxyphenyl)ethanamine to give the title compound as a white solid (0.5 mg, 2%). $^1$H NMR (500 MHz, DMSO-$d_6$) δ ppm 1.37 (d, J=7.3 Hz, 3 H), 2.81 (s, 3 H), 3.72-3.75 (m, 3 H), 4.86-4.94 (m, 1 H), 4.99 (s, 2 H), 6.85-6.93 (m, 2 H), 7.23-7.29 (m, 2 H), 7.68-7.74 (m, 1 H), 7.91-7.97 (m, 1 H), 7.99-8.05 (m, 1 H), 8.68 (d, J=8.3 Hz, 1 H); ESI-MS m/z [M+Na]$^+$ 375.0.

EXAMPLE 41

(S)-2-(6,8-dimethyl-4-oxobenzo[d][1,2,3]triazin-3 (4H)-yl)-N-(1-p-tolylethyl)acetamide

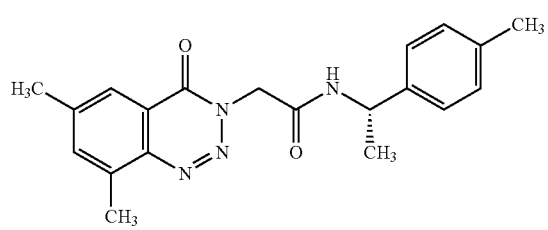

The title compound was prepared in a manner similar to Example 2 using 2-(6,8-dimethyl-4-oxobenzo[d][1,2,3]triazin-3(4H)-yl)acetic acid and (S)-1-(p-tolyl)ethanamine to give the title compound as a white solid (10.7 mg, 36%). $^1$H NMR (500 MHz, DMSO-$d_6$) δ ppm 1.37 (d, J=6.8 Hz, 3 H), 2.28 (s, 3 H), 2.73 (s, 3 H), 4.90 (quin, J=7.3 Hz, 1 H), 5.03 (d, J=2.4 Hz, 2 H), 7.13 (d, J=8.3 Hz, 2 H), 7.20-7.23 (m, 2 H), 7.77 (s, 1 H), 7.87 (s, 1 H), 8.71 (d, J=7.8 Hz, 1 H); ESI-MS m/z [M+H]$^+$ 351.1.

EXAMPLE 42

(S)-2-(6,8-dimethyl-4-oxobenzo[d][1,2,3]triazin-3(4H)-yl)-N-(1-(4-methoxyphenyl)ethyl)acetamide

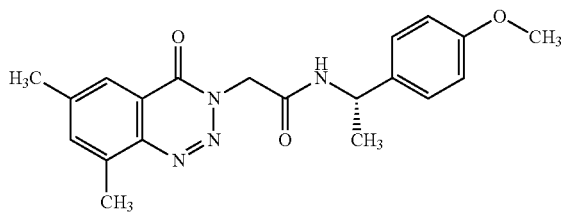

The title compound was prepared in a manner similar to Example 2 using 2-(6,8-dimethyl-4-oxobenzo[d][1,2,3]triazin-3(4H)-yl)acetic acid and (S)-1-(4-methoxyphenyl)ethanamine to give the title compound as a white solid (9.0 mg, 29%). $^1$H NMR (500 MHz, DMSO-d$_6$) δ ppm 1.37 (d, J=6.8 Hz, 3 H), 2.29 (d, J=2.4 Hz, 1 H), 2.73 (s, 3 H), 3.73 (s, 3 H), 4.90 (quin, J=7.2 Hz, 1 H), 5.02 (d, J=2.9 Hz, 2 H), 6.86-6.91 (m, 2 H), 7.23-7.27 (m, 2 H), 7.75-7.79 (m, 1 H), 7.88 (d, J=1.0 Hz, 1 H), 8.69 (d, J=7.8 Hz, 1 H); ESI-MS m/z [M+H]$^+$ 367.0.

EXAMPLE 43

(S)-2-(4-oxo-6-(trifluoromethyl)benzo[d][1,2,3]triazin-3(4H)-yl)-N-(1-p-tolylethyl)acetamide

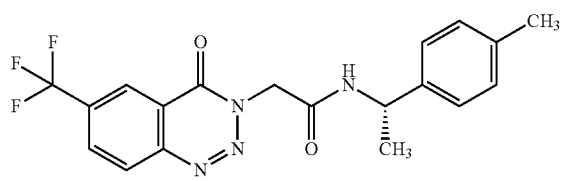 [SMILES: Cc1ccc([C@H](C)NC(=O)Cn2nnc3ccc(C(F)(F)F)cc3c2=O)cc1]

The title compound was prepared in a manner similar to Example 2 using 2-(4-oxo-6-(trifluoromethyl)benzo[d][1,2,3]triazin-3(4H)-yl)acetic acid and (S)-1-(p-tolyl)ethanamine to give the title compound as a white solid (16.8 mg, 59%). $^1$H NMR (500 MHz, DMSO-d$_6$) δ ppm 1.37 (d, J=6.8 Hz, 3 H), 2.26-2.28 (m, 3 H), 4.91 (t, J=7.6 Hz, 1 H), 5.11 (s, 2 H), 7.14 (d, J=7.8 Hz, 2 H), 7.20-7.25 (m, 2 H), 8.41-8.53 (m, 3 H), 8.75 (d, J=7.8 Hz, 1 H); ESI-MS m/z [M+H]$^+$ 391.0.

EXAMPLE 44

(S)-N-(1-(4-methoxyphenyl)ethyl)-2-(4-oxo-6-(trifluoromethyl)benzo[d][1,2,3]triazin-3(4H)-yl)acetamide

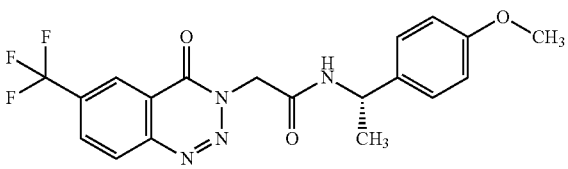 [SMILES: COc1ccc([C@H](C)NC(=O)Cn2nnc3ccc(C(F)(F)F)cc3c2=O)cc1]

The title compound was prepared in a manner similar to Example 2 using 2-(4-oxo-6-(trifluoromethyl)benzo[d][1,2,3]triazin-3(4H)-yl)acetic acid and (S)-1-(4-methoxyphenyl)ethanamine to give the title compound as a white solid (20.3 mg, 68%). $^1$H NMR (500 MHz, DMSO-d$_6$) δ ppm 1.37 (d, J=6.8 Hz, 3 H), 3.73 (s, 3 H), 4.86-4.95 (m, 1 H), 5.10 (d, J=1.0 Hz, 2 H), 6.84-6.93 (m, 2 H), 7.23-7.27 (m, 2 H), 8.41-8.54 (m, 3 H), 8.72 (d, J=8.3 Hz, 1 H); ESI-MS m/z [M+Na]$^+$ 429.0.

EXAMPLE 45

(S)-2-(8-fluoro-6-methyl-4-oxobenzo[d][1,2,3]triazin-3(4H)-yl)-N-(1-(p-tolyl)ethyl)acetamide

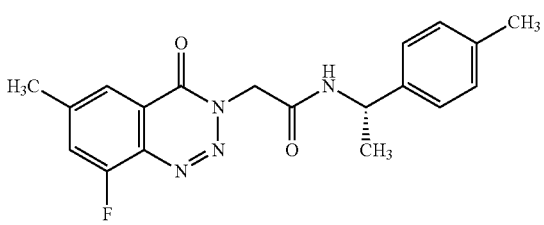

The title compound was prepared in a manner similar to Example 2 using 2-(8-fluoro-6-methyl-4-oxobenzo[d][1,2,3]triazin-3(4H)-yl)acetic acid and (S)-1-(p-tolyl)ethanamine to give the title compound as a white solid (25.5 mg, 57%). $^1$H NMR (500 MHz, DMSO-d$_6$) δ ppm 1.37 (d, J=6.8 Hz, 3 H), 2.27 (s, 3 H), 2.55 (s, 3 H), 4.90 (quin, J=7.2 Hz, 1 H), 5.06 (s, 2 H), 7.13 (d, J=7.8 Hz, 2 H), 7.22 (d, J=7.8 Hz, 2 H), 7.83-7.90 (m, 2 H), 8.72 (d, J=8.3 Hz, 1 H); ESI-MS m/z [M+H]$^+$ 355.4.

EXAMPLE 46

(S)-N-(1-(2-methoxy-4-methylphenyl)ethyl)-2-(4-oxobenzo[d][1,2,3]triazin-3(4H)-yl)acetamide

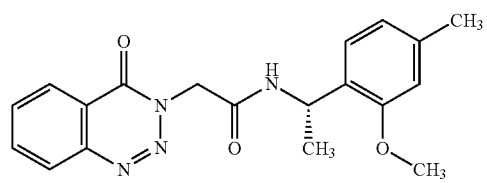 [SMILES: COc1cc(C)ccc1[C@H](C)NC(=O)Cn1nnc2ccccc2c1=O]

The title compound was prepared in a manner similar to Example 2 using 2-(4-oxobenzo[d][1,2,3]triazin-3(4H)-yl)acetic acid and (S)-1-(2-methoxy-4-methylphenyl)ethanamine, HCl to give the title compound as a tan solid (38.8 mg, 75%). $^1$H NMR (500 MHz, DMSO-d$_6$) δ ppm 1.29 (d, J=6.8 Hz, 3 H), 2.28 (s, 3 H), 3.77 (s, 3 H), 5.03-5.08 (m, 2 H), 5.16 (quin, J=7.2 Hz, 1 H), 6.75 (d, J=7.8 Hz, 1 H), 6.78 (s, 1 H), 7.19 (d, J=7.8 Hz, 1 H), 7.92-7.98 (m, 1 H), 8.08-8.15 (m, 1 H), 8.20-8.28 (m, 2 H), 8.66 (d, J=7.8 Hz, 1 H); ESI-MS m/z [M+H]$^+$ 353.2.

EXAMPLE 47

(S)-N-(1-(2-chloro-4-fluorophenyl)ethyl)-2-(4-oxobenzo[d][1,2,3]triazin-3(4H)-yl)acetamide

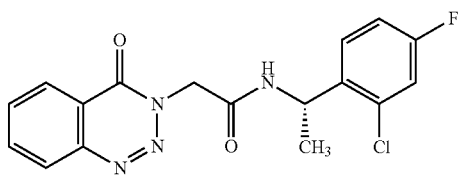 [SMILES: C[C@H](NC(=O)Cn1nnc2ccccc2c1=O)c1ccc(F)cc1Cl]

The title compound was prepared in a manner similar to Example 2 using 2-(4-oxobenzo[d][1,2,3]triazin-3(4H)-yl)acetic acid and (S)-1-(2-chloro-4-fluorophenyl)ethanamine, HCl to give the title compound as a white solid (30.1 mg, 57%). $^1$H NMR (500 MHz, DMSO-$d_6$) δ ppm 1.36 (d, J=6.8 Hz, 3 H), 5.09 (s, 2 H), 5.19 (quin, J=7.1 Hz, 1 H), 7.27 (td, J=8.5, 2.9 Hz, 1 H), 7.39 (dd, J=8.8, 2.9 Hz, 1 H), 7.54 (dd, J=8.8, 6.3 Hz, 1 H), 7.90-7.99 (m, 1 H), 8.11 (td, J=7.6, 1.5 Hz, 1 H), 8.21-8.27 (m, 2 H), 8.97 (d, J=7.3 Hz, 1 H); ESI-MS m/z [M, M+2]$^+$ 360.1, 362.1.

EXAMPLE 48

(S)-N-(1-(2-bromo-4-fluorophenyl)ethyl)-2-(4-oxobenzo[d][1,2,3]triazin-3(4H)-yl)acetamide

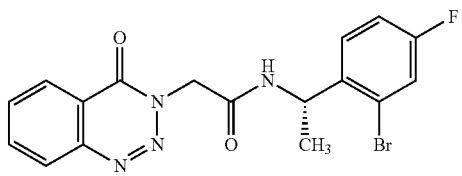 [SMILES: C[C@H](NC(=O)Cn1nnc2ccccc2c1=O)c1ccc(F)cc1Br]

The title compound was prepared in a manner similar to Example 2 using 2-(4-oxobenzo[d][1,2,3]triazin-3(4H)-yl)acetic acid and (S)-1-(2-bromo-4-fluorophenyl)ethanamine, HCl to give the title compound as a white solid (37.4 mg, 63%). $^1$H NMR (500 MHz, DMSO-$d_6$) δ ppm 1.35 (d, J=7.3 Hz, 3 H), 5.09 (s, 2 H), 5.11-5.19 (m, 1 H), 7.32 (td, J=8.5, 2.4 Hz, 1 H), 7.49-7.56 (m, 2 H), 7.92-7.98 (m, 1 H), 8.11 (td, 1.5 Hz, 1 H), 8.20-8.28 (m, 2 H), 9.00 (d, J=7.8 Hz, 1 H); ESI-MS m/z [M, M+2]$^+$ 405.1, 407.1.

EXAMPLE 49

(S)-N-(1-(4-fluorophenyl)ethyl)-2-(4-oxobenzo[d][1,2,3]triazin-3(4H)-yl)acetamide

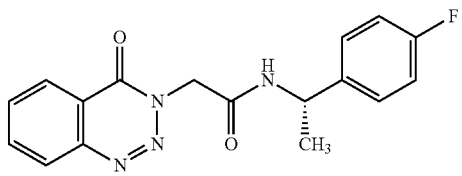 [SMILES: C[C@H](NC(=O)Cn1nnc2ccccc2c1=O)c1ccc(F)cc1]

The title compound was prepared in a manner similar to Example 2 using 2-(4-oxobenzo[d][1,2,3]triazin-3(4H)-yl)acetic acid and (S)-1-(4-fluorophenyl)ethanamine to give the title compound as a white solid (27.9 mg, 59%). $^1$H NMR (500 MHz, DMSO-$d_6$) δ ppm 1.36-1.41 (m, 3 H), 4.95 (quin, J=7.2 Hz, 1 H), 5.07 (s, 2 H), 7.12-7.21 (m, 2 H), 7.35-7.41 (m, 2 H), 7.92-7.99 (m, 1 H), 8.08-8.15 (m, 1 H), 8.20-8.29 (m, 2 H), 8.79 (d, J=7.8 Hz, 1 H); ESI-MS m/z [M+H]$^+$ 327.2.

EXAMPLE 50

(S)-N—((S)-1-(2-methoxy-4-methylphenyl)ethyl)-2-(4-oxobenzo[d][1,2,3]triazin-3(4H)-yl)propanamide

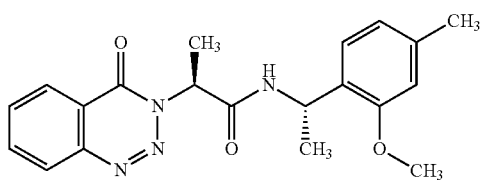

and

EXAMPLE 51

(R)—N((S)-1-(2-methoxy-4-methylphenyl)ethyl)-2-(4-oxobenzo[d][1,2,3]triazin-3(4H)-propanamide

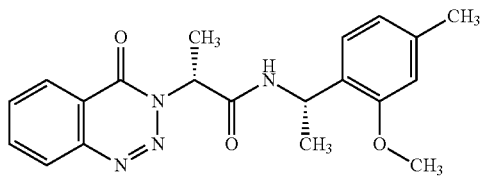 [SMILES: COc1cc(C)ccc1[C@H](C)NC(=O)[C@@H](C)n1nnc2ccccc2c1=O]

To a vial containing 2-(4-oxobenzo[d][1,2,3]triazin-3(4H)-yl)propanoic acid (50 mg, 0.228 mmol), HOBT (45 mg, 0.297 mmol) and EDC (66 mg, 0.342 mmol) was added DMF (760 µL). After stirring at RT for 5 min, (S)-1-(2-methoxy-4-methylphenyl)ethanamine, HCl (55 mg, 0.274 mmol) and DIPEA (240 µL, 1.369 mmol) were added. The reaction mixture was allowed to stir at RT for 1 h then water was added (10 mL). The solid was filtered off and washed with water, then dried to provide a tan solid. Purification by SFC gave the title compounds as white solids. Retention time 1.62 min: $^1$H NMR (500 MHz, DMSO-$d_6$) δ ppm 1.25 (d, J=6.8 Hz, 3 H), 1.70-1.77 (m, 3 H), 2.26 (s, 2 H), 3.13-3.19 (m, 3 H), 3.75 (s, 4 H), 5.13 (quin, J=7.1 Hz, 1 H), 5.60 (q, J=7.3 Hz, 1 H), 6.70 (d, J=7.3 Hz, 1 H), 6.76 (s, 1 H), 7.14 (d, J=7.3 Hz, 1 H), 7.89-7.96 (m, 1 H), 8.08-8.14 (m, 1 H), 8.20-8.27 (m, 2 H), 8.49 (d, J=7.8 Hz, 1 H); ESI-MS m/z [M+H]$^+$ 367.2; Retention time 2.72 min: $^1$H NMR (500 MHz, DMSO-$d_6$) δ ppm 1.26 (d, J=6.8 Hz, 3 H), 1.73 (d, J=7.3 Hz, 3 H), 2.28 (s, 3 H), 3.76 (s, 3 H), 5.14 (quin, J=7.2 Hz, 1 H), 5.53-5.60 (m, 1 H), 6.74 (d, J=7.8 Hz, 1 H), 6.78 (s, 1 H), 7.13 (d, J=7.3 Hz, 1 H), 7.90-7.98 (m, 1 H), 8.11 (ddd, J=8.4, 7.2, 1.5 Hz, 1 H), 8.22 (d, J=7.8 Hz, 1 H), 8.26 (dd, J=7.8, 1.0 Hz, 1 H), 8.52 (d, J=7.8 Hz, 1 H); ESI-MS m/z [M+H]$^+$ 367.2.

EXAMPLE 52

(S)-N-(1-(2,4-dimethylphenyl)ethyl)-2-(6-fluoro-4-oxobenzo[d][1,2,3]triazin-3(4H)-yl)acetamide

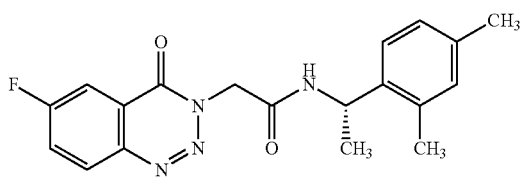 [SMILES: Cc1ccc([C@H](C)NC(=O)Cn2nnc3ccc(F)cc3c2=O)c(C)c1]

The title compound was prepared in a manner similar to Example 2 using 2-(6-fluoro-4-oxobenzo[d][1,2,3]triazin-3(4H)-yl)acetic acid and (S)-1-(2,4-dimethylphenyl)ethanamine, HCl to give the title compound as a white solid (23.6 mg, 74%). $^1$H NMR (500 MHz, DMSO-$d_6$) δ ppm 1.33 (d, J=6.8 Hz, 3 H), 2.23 (s, 3 H), 2.24 (s, 3 H), 4.99-5.08 (m, 3 H), 6.94 (s, 1 H), 7.01 (d, J=7.8 Hz, 1 H), 7.25 (d, J=7.8 Hz, 1 H), 7.97-8.03 (m, 2 H), 8.35 (dd, J=8.8, 4.9 Hz, 1 H), 8.73 (d, J=7.8 Hz, 1 H); ESI-MS m/z [M+H]$^+$ 355.3.

EXAMPLE 53

(S)-N-(1-(2-fluoro-4-methylphenyl)ethyl)-2-(4-oxobenzo[d][1,2,3]triazin-3 (4H)-yl)acetamide

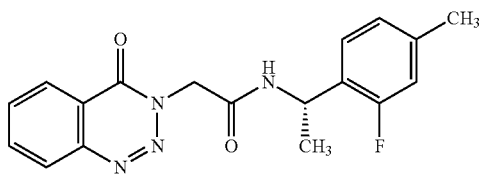 [SMILES: Cc1ccc([C@H](C)NC(=O)Cn2nnc3ccccc3c2=O)c(F)c1]

The title compound was prepared in a manner similar to Example 2 using 2-(4-oxobenzo[d][1,2,3]triazin-3(4H)-yl)acetic acid and (S)-1-(2-fluoro-4-methylphenyl)ethanamine, HCl to give the title compound as a white solid (23.4 mg, 71%). $^1$H NMR (500 MHz, DMSO-$d_6$) δ ppm 1.37 (d, J=7.3 Hz, 3 H), 2.29 (s, 3 H), 5.05-5.16 (m, 3 H), 6.93-7.03 (m, 2 H), 7.31 (t, J=8.1 Hz, 1 H), 7.91-7.99 (m, 1 H), 8.11 (td, J=7.6, 1.5 Hz, 1 H), 8.20-8.28 (m, 2 H), 8.83 (d, J=7.3 Hz, 1 H); ESI-MS m/z [M+H]$^+$ 341.2.

EXAMPLE 54

(S)-N-(1-(2-fluoro-4-methylphenyl)ethyl)-2-(6-fluoro-4-oxobenzo[d][1,2,3]triazin-3(4H)-yl)acetamide

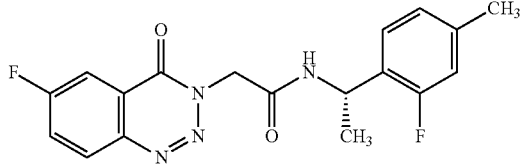 [SMILES: Cc1ccc([C@H](C)NC(=O)Cn2nnc3ccc(F)cc3c2=O)c(F)c1]

The title compound was prepared in a manner similar to Example 2 using 2-(6-fluoro-4-oxobenzo[d][1,2,3]triazin-3(4H)-yl)acetic acid and (S)-1-(2-fluoro-4-methylphenyl)ethanamine, HCl to give the title compound as a white solid (13.6 mg, 42%). $^1$H NMR (500 MHz, DMSO-$d_6$) δ ppm 1.37 (d, J=6.8 Hz, 3 H), 2.29 (s, 3 H), 5.05-5.14 (m, 3 H), 6.91-7.04 (m, 2 H), 7.30 (t, J=8.1 Hz, 1 H), 7.97-8.04 (m, 2 H), 8.36 (dd, J=8.5, 5.1 Hz, 1 H), 8.84 (d, J=7.8 Hz, 1 H); ESI-MS m/z [M+H]$^+$ 359.2.

EXAMPLE 55

(S)-2-(6-fluoro-4-oxobenzo[d][1,2,3]triazin-3(4H)-yl)-N-(1-(4-(trifluoromethoxy)phenyl)ethyl)acetamide

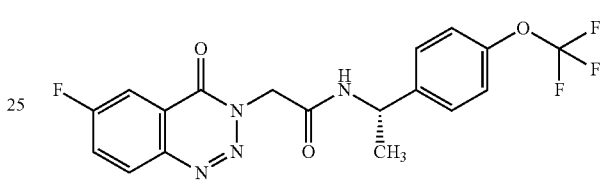

The title compound was prepared in a manner similar to Example 2 using 2-(6-fluoro-4-oxobenzo[d][1,2,3]triazin-3(4H)-yl)acetic acid and (S)-1-(4-(trifluoromethoxy)phenyl)ethanamine to give the title compound as a white solid (13.2 mg, 36%). $^1$H NMR (500 MHz, DMSO-$d_6$) δ ppm 1.37-1.42 (m, 3 H), 4.97 (quin, J=7.1 Hz, 1 H), 5.08 (s, 2 H), 7.30-7.35 (m, 2 H), 7.42-7.47 (m, 2 H), 7.97-8.03 (m, 2 H), 8.33-8.40 (m, 1 H), 8.85 (d, J=7.8 Hz, 1 H); ESI-MS m/z [M+H]$^+$ 411.2.

EXAMPLE 56

(S)-2-(7-methoxy-4-oxobenzo[d][1,2,3]triazin-3(4H)-yl)-N-(1-(4-(trifluoromethoxy)phenyl)ethyl)acetamide

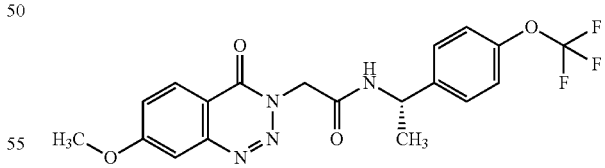

The title compound was prepared in a manner similar to Example 2 using 2-(7-methoxy-4-oxobenzo[d][1,2,3]triazin-3(4H)-yl)acetic acid and (S)-1-(4-(trifluoromethoxy)phenyl)ethanamine to give the title compound as a white solid (21.8 mg, 81%). $^1$H NMR (500 MHz, DMSO-$d_6$) δ ppm 1.40 (d, J=6.8 Hz, 3 H), 3.99 (s, 3 H), 4.97 (quin, J=7.2 Hz, 1 H), 5.06 (s, 2 H), 7.33 (d, J=8.3 Hz, 2 H), 7.44-7.52 (m, 3 H), 7.67 (d, J=2.4 Hz, 1 H), 8.15 (d, J=9.3 Hz, 1 H), 8.84 (d, J=7.8 Hz, 1 H); ESI-MS m/z [M+H]$^+$ 423.4.

EXAMPLE 57

(S)-2-(6-methoxy-4-oxobenzo[d][1,2,3]triazin-3(4H)-yl)-N-(1-(4-(trifluoromethoxy)phenyl)ethyl)acetamide

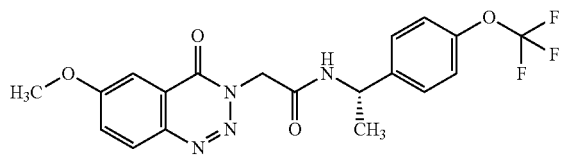 [SMILES: COc1ccc2nnn(CC(=O)N[C@@H](C)c3ccc(OC(F)(F)F)cc3)c(=O)c2c1]

The title compound was prepared in a manner similar to Example 2 using 2-(6-methoxy-4-oxobenzo[d][1,2,3]triazin-3(4H)-yl)acetic acid and (S)-1-(4-(trifluoromethoxy)phenyl)ethanamine to give the title compound as a white solid (17.3 mg, 64%). $^1$H NMR (500 MHz, DMSO-$d_6$) δ ppm 1.40 (d, J=6.8 Hz, 3 H), 3.98 (s, 3 H), 4.97 (quin, J=7.1 Hz, 1 H), 5.06 (s, 2 H), 7.33 (d, J=7.8 Hz, 2 H), 7.44-7.49 (m, 2 H), 7.58 (d, J=2.9 Hz, 1 H), 7.64-7.69 (m, 1 H), 8.17 (d, J=8.8 Hz, 1 H), 8.83 (d, J=7.8 Hz, 1 H); ESI-MS m/z [M+H]$^+$ 423.3.

EXAMPLE 58

(S)-2-(5-methoxy-4-oxobenzo[d][1,2,3]triazin-3(4H)-yl)-N-(1-(4-(trifluoromethoxy)phenyl)ethyl)acetamide

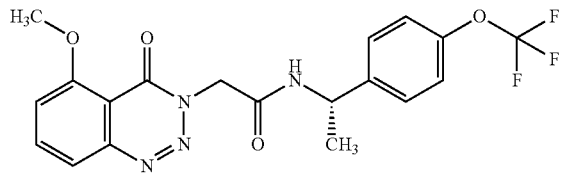

The title compound was prepared in a manner similar to Example 2 using 2-(5-methoxy-4-oxobenzo[d][1,2,3]triazin-3(4H)-yl)acetic acid and (S)-1-(4-(trifluoromethoxy)phenyl)ethanamine to give the title compound as a white solid (16.2 mg, 60%). $^1$H NMR (500 MHz, DMSO-$d_6$) δ ppm 1.40 (d, J=7.3 Hz, 3 H), 3.93 (s, 3 H), 4.93-5.00 (m, 3 H), 7.33 (d, J=8.3 Hz, 2 H), 7.43-7.48 (m, 3 H), 7.65-7.72 (m, 1 H), 8.00 (t, J=8.3 Hz, 1 H), 8.79 (d, J=7.8 Hz, 1 H); ESI-MS m/z [M+H]$^+$ 423.3.

EXAMPLE 59

(S)-2-(7-methoxy-4-oxobenzo[d][1,2,3]triazin-3(4H)-yl)-N-(1-(4-(trifluoromethyl)phenyl)ethyl)acetamide

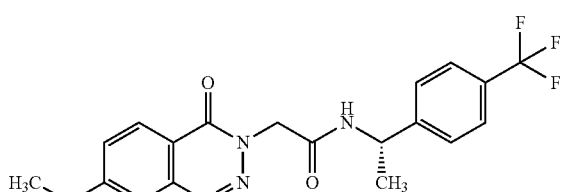

The title compound was prepared in a manner similar to Example 2 using 2-(7-methoxy-4-oxobenzo[d][1,2,3]triazin-3(4H)-yl)acetic acid and (S)-1-(4-(trifluoromethyl)phenyl)ethanamine to give the title compound as a white solid (22.5 mg, 87%). $^1$H NMR (500 MHz, DMSO-$d_6$) δ ppm 1.41 (d, J=6.8 Hz, 3 H), 3.99 (s, 3 H), 5.00 (quin, J=7.1 Hz, 1 H), 5.07 (s, 2 H), 7.49 (dd, J=8.8, 2.9 Hz, 1 H), 7.56 (d, J=8.3 Hz, 2 H), 7.67 (d, J=2.9 Hz, 1 H), 7.70 (d, J=8.8 Hz, 2 H), 8.15 (d, J=8.8 Hz, 1 H), 8.91 (d, J=7.8 Hz, 1 H); ESI-MS m/z [M+H]$^+$ 407.4.

EXAMPLE 60

(S)-2-(6-methoxy-4-oxobenzo[d][1,2,3]triazin-3(4H)-yl)-N-(1-(4-(trifluoromethyl)phenyl)ethyl)acetamide

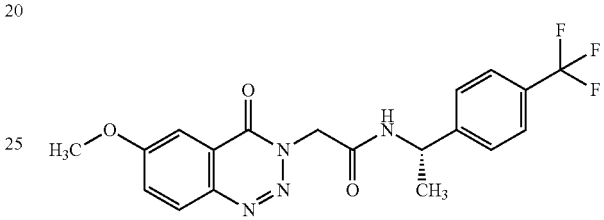

The title compound was prepared in a manner similar to Example 2 using 2-(6-methoxy-4-oxobenzo[d][1,2,3]triazin-3(4H)-yl)acetic acid and (S)-1-(4-(trifluoromethyl)phenyl)ethanamine to give the title compound as a white solid (19.9 mg, 77%). $^1$H NMR (500 MHz, DMSO-$d_6$) δ ppm 1.42 (d, J=6.8 Hz, 3 H), 3.97 (s, 3 H), 4.97-5.03 (m, 1 H), 5.07 (s, 2 H), 7.54-7.58 (m, 3 H), 7.65 (dd, J=9.0, 2.7 Hz, 1 H), 7.70 (d, J=7.8 Hz, 2 H), 8.17 (d, J=9.3 Hz, 1 H), 8.90 (d, J=7.8 Hz, 1 H); ESI-MS m/z [M+H]$^+$ 407.4.

EXAMPLE 61

(S)-2-(5-methoxy-4-oxobenzo[d][1,2,3]triazin-3(4H)-yl)-N-(1-(4-(trifluoromethyl)phenyl)ethyl)acetamide

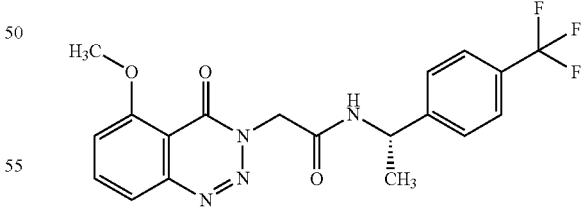

The title compound was prepared in a manner similar to Example 2 using 2-(5-methoxy-4-oxobenzo[d][1,2,3]triazin-3(4H)-yl)acetic acid and (S)-1-(4-(trifluoromethyl)phenyl)ethanamine to give the title compound as a white solid (12.9 mg, 50%). $^1$H NMR (500 MHz, DMSO-$d_6$) δ ppm 1.41 (d, J=7.3 Hz, 3 H), 3.93 (s, 3 H), 4.96-5.04 (m, 3 H), 7.41-7.47 (m, 1 H), 7.56 (d, J=8.3 Hz, 2 H), 7.66-7.73 (m, 3 H), 7.99 (t, J=8.3 Hz, 1 H), 8.86 (d, J=7.8 Hz, 1 H); ESI-MS m/z [M+H]$^+$ 407.4.

EXAMPLE 62

(S)-2-(8-methoxy-4-oxobenzo[d][1,2,3]triazin-3(4H)-yl)-N-(1-(4-(trifluoromethoxy)phenyl)ethyl)acetamide

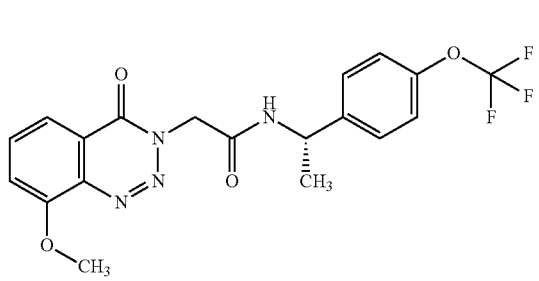 [SMILES: COc1cccc2c(=O)n(CC(=O)N[C@@H](C)c3ccc(OC(F)(F)F)cc3)nnc12]

The title compound was prepared in a manner similar to Example 2 using 2-(8-methoxy-4-oxobenzo[d][1,2,3]triazin-3(4H)-yl)acetic acid and (S)-1-(4-(trifluoromethoxy)phenyl)ethanamine to give the title compound as a white solid (4.8 mg, 18%). $^1$H NMR (500 MHz, DMSO-$d_6$) δ ppm 1.39 (d, J=7.3 Hz, 3 H), 4.04 (s, 3 H), 4.97 (quin, J=7.1 Hz, 1 H), 5.06 (s, 2 H), 7.33 (d, J=8.3 Hz, 2 H), 7.43-7.49 (m, 2 H), 7.62-7.67 (m, 1 H), 7.74 (dd, J=7.8, 1.0 Hz, 1 H), 7.84-7.91 (m, 1 H), 8.82 (d, J=7.3 Hz, 1 H); ESI-MS m/z [M+H]$^+$ 423.3.

EXAMPLE 63

(S)-2-(8-methoxy-4-oxobenzo[d][1,2,3]triazin-3(4H)-yl)-N-(1-(4-(trifluoromethyl)phenyl)ethyl)acetamide

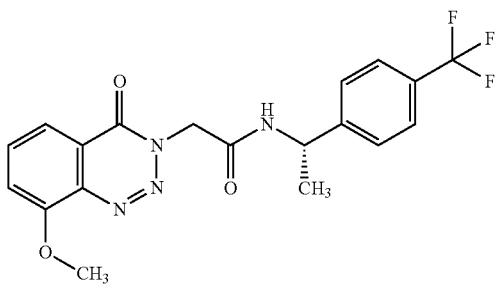 [SMILES: COc1cccc2c(=O)n(CC(=O)N[C@@H](C)c3ccc(C(F)(F)F)cc3)nnc12]

The title compound was prepared in a manner similar to Example 4 using 2-(8-methoxy-4-oxobenzo[d][1,2,3]triazin-3(4H)-yl)acetic acid and (S)-1-(4-(trifluoromethyl)phenyl)ethanamine to give the title compound as a white solid (2.6 mg, 10%). $^1$H NMR (500 MHz, DMSO-$d_6$) δ ppm 1.41 (d, J=6.8 Hz, 3 H), 4.04 (s, 3 H), 5.00 (quin, J=7.3 Hz, 1 H), 5.07 (s, 2 H), 7.56 (d, J=8.3 Hz, 2 H), 7.65 (d, J=8.3 Hz, 1 H), 7.70 (d, J=8.3 Hz, 2 H), 7.74 (dd, J=8.1, 1.2 Hz, 1 H), 7.84-7.90 (m, 1 H), 8.89 (d, J=7.8 Hz, 1 H); ESI-MS m/z [M+H]$^+$ 407.3.

EXAMPLE 64

(S)-2-(6-fluoro-4-oxobenzo[d][1,2,3]triazin-3(4H)-yl)-N-(1-(4-(trifluoromethyl)phenyl)ethyl)acetamide

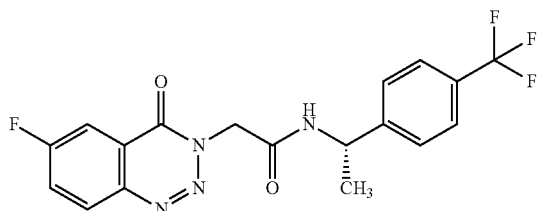

The title compound was prepared in a manner similar to Example 2 using 2-(6-fluoro-4-oxobenzo[d][1,2,3]triazin-3(4H)-yl)acetic acid and (S)-1-(4-(trifluoromethyl)phenyl)ethanamine to give the title compound as a white solid (10.6 mg, 40%). $^1$H NMR (500 MHz, DMSO-$d_6$) δ ppm 1.41 (d, J=7.3 Hz, 3 H), 4.97-5.05 (m, 1 H), 5.10 (s, 2 H), 7.56 (d, J=7.8 Hz, 2 H), 7.70 (d, J=8.3 Hz, 2 H), 7.97-8.02 (m, 2 H), 8.36 (ddq, J=8.2, 4.9, 1.5, 1.5, 1.5 Hz, 1 H), 8.92 (d, J=7.8 Hz, 1 H); ESI-MS m/z [M+H]$^+$ 395.3.

EXAMPLE 65

(S)-N-(1-(2-fluoro-4-(trifluoromethyl)phenyl)ethyl)-2-(4-oxobenzo[d][1,2,3]triazin-3(4H)-yl)acetamide

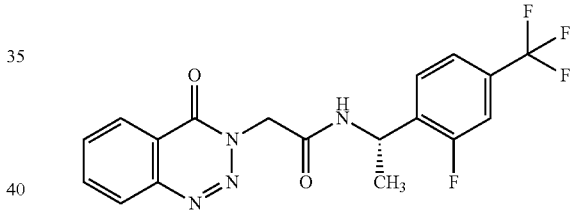

The title compound was prepared in a manner similar to Example 2 using 2-(4-oxobenzo[d][1,2,3]triazin-3(4H)-yl)acetic acid and (S)-1-(2-fluoro-4-(trifluoromethyl)phenyl)ethanamine to give the title compound as a white solid (11.3 mg, 60%). $^1$H NMR (500 MHz, DMSO-$d_6$) δ ppm 1.42 (d, J=6.8 Hz, 3 H), 5.10 (s, 2 H), 5.14-5.21 (m, 1 H), 7.59-7.70 (m, 3 H), 7.92-7.98 (m, 1 H), 8.11 (ddd, J=8.4, 7.2, 1.5 Hz, 1 H), 8.21-8.27 (m, 2 H), 9.02 (d, J=7.3 Hz, 1 H); ESI-MS m/z [M+H]$^+$ 395.6.

EXAMPLE 66

(S)-N-(1-(4-(difluoromethoxy)phenyl)ethyl)-2-(4-oxobenzo[d][1,2,3]triazin-3(4H)-yl)acetamide

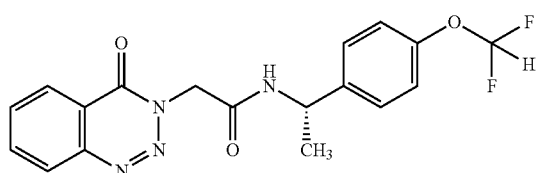

The title compound was prepared in a manner similar to Example 2 using 2-(4-oxobenzo[d][1,2,3]triazin-3(4H)-yl)acetic acid and (S)-1-(4-(difluoromethoxy)phenyl)ethanamine, HCl to give the title compound as a white solid (19.2 mg, 53%). $^1$H NMR (500 MHz, DMSO-$d_6$) δ ppm 1.35-1.40 (m, 3 H), 4.88-4.99 (m, 1 H), 5.03-5.09 (m, 2 H), 7.03-7.36 (m, 3 H), 7.14 (d, J=8.8 Hz, 2 H), 7.39 (d, J=8.8 Hz, 2 H), 7.95-7.98 (m, 1 H), 8.08-8.15 (m, 1 H), 8.21-8.28 (m, 2 H), 8.81 (d, J=7.8 Hz, 1 H); ESI-MS m/z [M+H]$^+$ 375.7.

EXAMPLE 67

(S)-N-(1-(2-fluoro-4-(trifluoromethyl)phenyl)ethyl)-2-(5-methoxy-4-oxobenzo[d][1,2,3]triazin-3(4H)-yl)acetamide

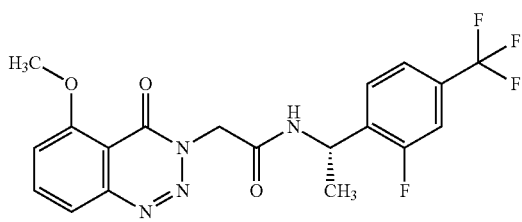 [SMILES: COc1cccc2nnn(CC(=O)N[C@@H](C)c3ccc(C(F)(F)F)cc3F)c(=O)c12]

The title compound was prepared in a manner similar to Example 2 using 2-(5-methoxy-4-oxobenzo[d][1,2,3]triazin-3(4H)-yl)acetic acid and (S)-1-(2-fluoro-4-(trifluoromethyl)phenyl)ethanamine to give the title compound as a white solid (15.0 mg, 73%). $^1$H NMR (500 MHz, DMSO-$d_6$) δ ppm 1.42 (d, J=6.8 Hz, 3 H), 3.92 (s, 3 H), 4.97-5.02 (m, 2 H), 5.16 (quin, J=7.1 Hz, 1 H), 7.44 (d, J=8.3 Hz, 1 H), 7.57-7.72 (m, 4 H), 7.99 (t, J=8.1 Hz, 1 H), 8.97 (d, J=7.3 Hz, 1 H); ESI-MS m/z [M+H]$^+$ 425.4.

EXAMPLE 68

(S)-N-(1-(4-(difluoromethoxy)phenyl)ethyl)-2-(6-fluoro-4-oxobenzo[d][1,2,3]triazin-3(4H)-yl)acetamide

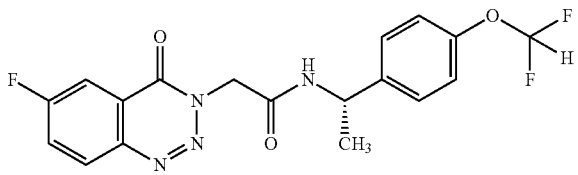 [SMILES: C[C@H](NC(=O)Cn1nnc2ccc(F)cc2c1=O)c1ccc(OC(F)F)cc1]

The title compound was prepared in a manner similar to Example 2 using 2-(6-fluoro-4-oxobenzo[d][1,2,3]triazin-3(4H)-yl)acetic acid and (S)-1-(4-(difluoromethoxy)phenyl)ethanamine, HCl to give the title compound as a white solid (12.1 mg, 55%). $^1$H NMR (500 MHz, DMSO-$d_6$) δ ppm 1.38 (d, J=6.8 Hz, 3 H), 4.89-4.99 (m, 1 H), 5.07 (s, 2 H), 7.03-7.41 (m, 5 H), 7.95-8.05 (m, 2 H), 8.33-8.40 (m, 1 H), 8.77-8.84 (m, 1 H); ESI-MS m/z [M+H]$^+$ 393.4.

EXAMPLE 69

(S)-N-(1-(4-(difluoromethoxy)phenyl)ethyl)-2-(5-methoxy-4-oxobenzo[d][1,2,3]triazin-3(4H)-yl)acetamide

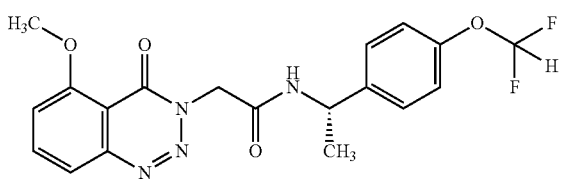 [SMILES: COc1cccc2nnn(CC(=O)N[C@@H](C)c3ccc(OC(F)F)cc3)c(=O)c12]

The title compound was prepared in a manner similar to Example 2 using 2-(5-methoxy-4-oxobenzo[d][1,2,3]triazin-3(4H)-yl)acetic acid and (S)-1-(4-(difluoromethoxy)phenyl)ethanamine, HCl to give the title compound as a white solid (17.5 mg, 78%). $^1$H NMR (500 MHz, DMSO-$d_6$) δ ppm 1.38 (d, J=6.8 Hz, 3 H), 3.93 (s, 3 H), 4.89-5.00 (m, 3 H), 7.01-7.41 (m, 2 H), 7.11-7.16 (m, 1 H), 7.42-7.47 (m, 1 H), 7.67-7.72 (m, 1 H), 7.99 (t, J=8.3 Hz, 1 H), 8.75 (d, J=7.8 Hz, 1 H); ESI-MS m/z [M+H]$^+$ 405.4.

EXAMPLE 70

(S)-N-(1-(2-fluoro-4-(trifluoromethoxy)phenyl)ethyl)-2-(4-oxobenzo[d][1,2,3]triazin-3(4H)-yl)acetamide

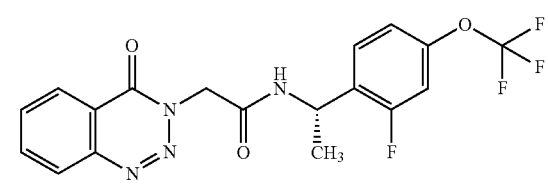 [SMILES: C[C@H](NC(=O)Cn1nnc2ccccc2c1=O)c1ccc(OC(F)(F)F)cc1F]

The title compound was prepared in a manner similar to Example 2 using 2-(4-oxobenzo[d][1,2,3]triazin-3(4H)-yl)acetic acid and (S)-1-(2-fluoro-4-(trifluoromethoxy)phenyl)ethanamine, HCl to give the title compound as a white solid (6.0 mg, 27%). $^1$H NMR (500 MHz, DMSO-$d_6$) δ ppm 1.40 (d, J=6.8 Hz, 3 H), 5.09 (s, 2 H), 5.13 (quin, J=7.1 Hz, 1 H), 7.27 (d, J=8.8 Hz, 1 H), 7.36 (dd, J=10.5, 1.7 Hz, 1 H), 7.56 (t, J=8.5 Hz, 1 H), 7.92-7.99 (m, 1 H), 8.11 (td, J=7.6, 1.5 Hz, 1 H), 8.21-8.28 (m, 2 H), 8.95 (d, J=7.8 Hz, 1 H); ESI-MS m/z [M+H]$^+$ 411.3.

EXAMPLE 71

(S)-N-(1-(2-fluoro-4-(trifluoromethoxy)phenyl)ethyl)-2-(6-fluoro-4-oxobenzo[d][1,2,3]triazin-3(4H)-yl)acetamide

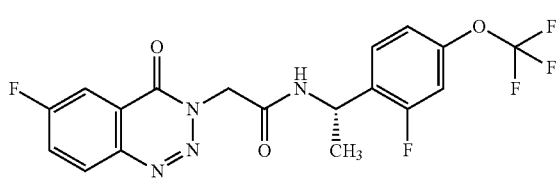

The title compound was prepared in a manner similar to Example 2 using 2-(6-fluoro-4-oxobenzo[d][1,2,3]triazin-3(4H)-yl)acetic acid and (S)-1-(2-fluoro-4-(trifluoromethoxy)phenyl)ethanamine, HCl to give the title compound as a white solid (7.8 mg, 33%). $^1$H NMR (500 MHz, DMSO-$d_6$) δ ppm 1.40 (d, J=6.8 Hz, 3 H), 5.09 (s, 2 H), 5.10-5.17 (m, 1 H), 7.27 (d, J=9.8 Hz, 1 H), 7.36 (d, J=10.7 Hz, 1 H), 7.55 (t, J=8.5 Hz, 1 H), 7.95-8.04 (m, 2 H), 8.36 (dd, J=8.5, 5.1 Hz, 1 H), 8.95 (d, J=7.3 Hz, 1 H); ESI-MS m/z [M+H]$^+$ 429.2.

EXAMPLE 72

(S)-N-(1-(2-fluoro-4-(trifluoromethoxy)phenyl)ethyl)-2-(5-methoxy-4-oxobenzo[d][1,2,3]triazin-3(4H)-yl)acetamide

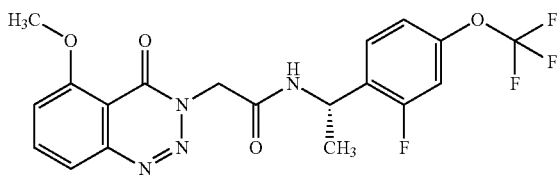 [SMILES: COc1cccc2nnn(CC(=O)N[C@@H](C)c3ccc(OC(F)(F)F)cc3F)c(=O)c12]

The title compound was prepared in a manner similar to Example 2 using 2-(5-methoxy-4-oxobenzo[d][1,2,3]triazin-3(4H)-yl)acetic acid and (S)-1-(2-fluoro-4-(trifluoromethoxy)phenyl)ethanamine, HCl to give the title compound as a white solid (11.8 mg, 49%). $^1$H NMR (500 MHz, DMSO-$d_6$) δ ppm 1.37-1.42 (m, 3 H), 3.92 (s, 3 H), 4.99 (s, 2 H), 5.13 (quin, J=7.2 Hz, 1 H), 7.26 (d, J=8.8 Hz, 1 H), 7.33-7.39 (m, 1 H), 7.44 (d, J=8.3 Hz, 1 H), 7.56 (t, J=8.5 Hz, 1 H), 7.69 (dd, J=7.8, 1.0 Hz, 1 H), 7.97-8.03 (m, 1 H), 8.90 (d, J=7.3 Hz, 1 H); ESI-MS m/z [M+H]$^+$ 441.2.

EXAMPLE 73

2-(4-oxobenzo[d][1,2,3]triazin-3(4H)-yl)-N-phenethylacetamide

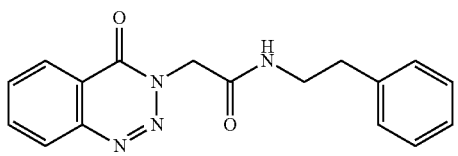 [SMILES: O=C(Cn1nnc2ccccc2c1=O)NCCc1ccccc1]

To a solution of 2-(4-oxobenzo[d][1,2,3]triazin-3(4H)-yl) acetic acid (25 mg, 0.122 mmol) in DCM (406 μL) was added 1 drop DMF and oxalyl chloride (21 μL, 0.244 mmol). The mixture was allowed to stir at RT for 45 min, and was then added to a solution of 2-phenylethanamine (15 μL, 0.122 mmol) and triethylamine (19 μL, 0.134 mmol) in 400 μL DCM. The reaction mixture was stirred at RT for 18 h. Purification by HPLC Method A provided the title compound as a white solid (11.1 mg, 30%). $^1$H NMR (500 MHz, DMSO-$d_6$) δ ppm 2.73 (t, J=7.6 Hz, 2 H), 3.29-3.34 (m, 2 H), 5.00 (s, 2 H), 7.20-7.33 (m, 5 H), 7.93-7.99 (m, 1 H), 8.12 (td, J=7.6, 1.5 Hz, 1 H), 8.23-8.29 (m, 2 H), 8.41 (t, J=5.6 Hz, 1 H); ESI-MS m/z [M+H]$^+$ 309.9.

EXAMPLE 74

N-(4-chlorophenethyl)-2-(4-oxobenzo[d][1,2,3]triazin-3(4H)-yl)acetamide

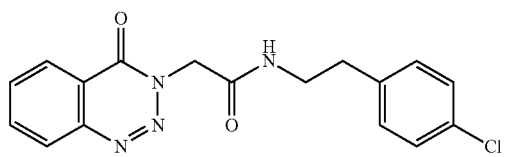 [SMILES: O=C(Cn1nnc2ccccc2c1=O)NCCc1ccc(Cl)cc1]

To a solution of 2-(4-oxobenzo[d][1,2,3]triazin-3(4H)-yl) acetic acid (25 mg, 0.122 mmol) in DCM (406 μL) was added 1 drop DMF and oxalyl chloride (21 μL, 0.244 mmol). The mixture was stirred at RT for 45 min, then added to a solution of 2-(4-chlorophenyl)ethanamine (17 μL, 0.122 mmol) and triethylamine (19 μL, 0.134 mmol) in 400 μL DCM. The reaction mixture was stirred at RT for 18 h. Purification by flash silica gel chromatography, eluting with 0-70% EtOAc in heptanes provided the title compound as a white solid (5.2 mg, 13%). $^1$H NMR (500 MHz, DMSO-$d_6$) δ ppm 2.73 (t, J=7.1 Hz, 2 H), 3.28-3.32 (m, 2 H), 4.99 (s, 2 H), 7.24-7.29 (m, 2 H), 7.33-7.37 (m, 2 H), 7.93-8.00 (m, 1 H), 8.12 (td, J=7.6, 1.5 Hz, 1 H), 8.23-8.29 (m, 2 H), 8.39 (t, J=5.6 Hz, 1 H); ESI-MS m/z [M, M+2]$^+$ 342.9, 344.9.

EXAMPLE 75

N-(3-chlorophenethyl)-2-(4-oxobenzo[d][1,2,3]triazin-3(4H)-yl)acetamide

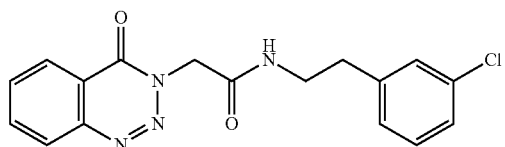

The title compound was prepared in a manner similar to Example 74 using 2-(4-oxobenzo[d][1,2,3]triazin-3(4H)-yl) acetic acid and 2-(3-chlorophenyl)ethanamine to give the title compound as a white solid (8.4 mg, 20%). $^1$H NMR (500 MHz, DMSO-$d_6$) δ ppm 2.75 (t, J=7.1 Hz, 2 H), 3.32-3.36 (m, 2 H), 4.99 (s, 2 H), 7.18-7.35 (m, 4 H), 7.96 (td, J=7.6, 1.5 Hz, 1 H), 8.12 (td, J=7.6, 1.5 Hz, 1 H), 8.23-8.29 (m, 2 H), 8.41 (t, J=5.6 Hz, 1 H); ESI-MS m/z [M, M+2]$^+$ 342.9, 344.9.

EXAMPLE 76

N-(4-methylphenethyl)-2-(4-oxobenzo[d][1,2,3]triazin-3(4H)-yl)acetamide

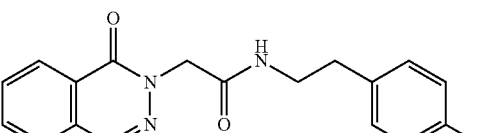

The title compound was prepared in a manner similar to Example 73 using 2-(4-oxobenzo[d][1,2,3]triazin-3(4H)-yl)acetic acid and 2-(p-tolyl)ethanamine to give the title compound as a white solid (5.5 mg, 14%). $^1$H NMR (500 MHz, DMSO-d$_6$) δ ppm 2.26 (s, 3H), 2.68 (t, J=7.6 Hz, 2H), 3.25-3.31 (m, 2H), 4.99 (s, 2H), 7.10 (s, 4H), 7.92-8.00 (m, 1H), 8.12 (ddd, J=8.4, 7.2, 1.5 Hz, 1H), 8.23-8.29 (m, 2H), 8.37-8.42 (m, 1H); ESI-MS m/z [M+H]$^+$ 323.0.

EXAMPLE 77

N-(4-hydroxyphenethyl)-2-(4-oxobenzo[d][1,2,3]triazin-3(4H)-yl)acetamide

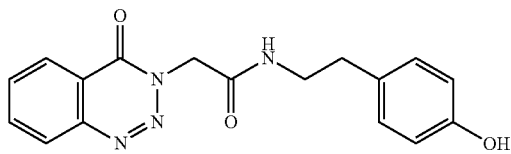 [SMILES: O=C(Cn1nnc2ccccc2c1=O)NCCc1ccc(O)cc1]

The title compound was prepared in a manner similar to Example 1 using 2-(4-oxobenzo[d][1,2,3]triazin-3(4H)-yl)acetic acid and 4-(2-aminoethyl)phenol to give the title compound as a white solid (26.7 mg, 68%). $^1$H NMR (500 MHz, DMSO-d$_6$) δ ppm 2.59-2.64 (m, 2 H), 3.22-3.25 (m, 2 H), 4.99 (s, 2 H), 6.65-6.71 (m, 2 H), 7.00 (d, J=8.8 Hz, 2 H), 7.93-7.99 (m, 1 H), 8.12 (td, J=7.8, 1.5 Hz, 1 H), 8.22-8.29 (m, 2 H), 8.37 (t, J=5.6 Hz, 1 H), 9.15-9.19 (m, 1 H); ESI-MS m/z [M+H]$^+$ 325.0.

EXAMPLE 78

N-(4-methoxyphenethyl)-N-methyl-2-(4-oxobenzo[d][1,2,3]triazin-3(4H)-yl)acetamide

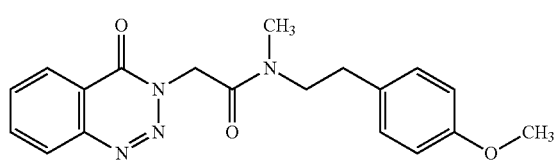 [SMILES: COc1ccc(CCN(C)C(=O)Cn2nnc3ccccc3c2=O)cc1]

The title compound was prepared in a manner similar to Example 4 using 2-(4-oxobenzo[d][1,2,3]triazin-3(4H)-yl)acetic acid and 2-(4-methoxyphenyl)-N-methylethanamine to give the title compound as a white solid (15.2 mg, 59%). Mixture of rotamers: $^1$H NMR (500 MHz, DMSO-d$_6$) δ ppm 2.66-2.73 (m, 1 H), 2.83-3.10 (m, 4 H), 2.90 (t, J=7.6 Hz, 1 H), 3.41-3.46 (m, 1 H), 3.63 (t, J=7.3 Hz, 1 H), 3.70-3.76 (m, 3 H), 5.11-5.34 (m, 2 H), 6.82-6.88 (m, 1 H), 6.89-6.94 (m, 1 H), 7.12-7.16 (m, 1 H), 7.24-7.28 (m, 1 H), 7.92-8.01 (m, 1 H), 8.09-8.17 (m, 1 H), 8.21-8.30 (m, 2 H); ESI-MS m/z [M+H]$^+$ 353.9.

EXAMPLE 79

(S)-2-(4-oxobenzo[d][1,2,3]triazin-3 (4H)-yl)-N-(2-phenylpropyl)acetamide

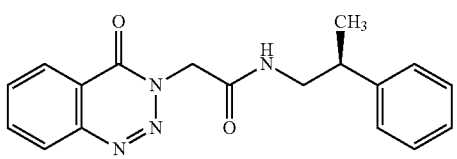 [SMILES: C[C@H](CNC(=O)Cn1nnc2ccccc2c1=O)c1ccccc1]

The title compound was prepared in a manner similar to Example 2 using 2-(4-oxobenzo[d][1,2,3]triazin-3(4H)-yl)acetic acid and (S)-2-phenylpropan-1-amine to give the title compound as a white solid (12.5 mg, 53%). $^1$H NMR (500 MHz, DMSO-d$_6$) δ ppm 1.20 (d, J=6.8 Hz, 3 H), 2.89 (sxt, J=7.1 Hz, 1 H), 3.24 (dd, J=7.1, 6.1 Hz, 2 H), 4.99 (s, 2 H), 7.17-7.34 (m, 5 H), 7.92-7.99 (m, 1 H), 8.12 (ddd, J=8.4, 7.2, 1.5 Hz, 1 H), 8.22-8.29 (m, 2 H), 8.36 (t, J=5.9 Hz, 1 H); ESI-MS m/z [M+H]$^+$ 323.0.

EXAMPLE 80

(R)-2-(4-oxobenzo[d][1,2,3]triazin-3(4H)-yl)-N-(2-phenylpropyl)acetamide

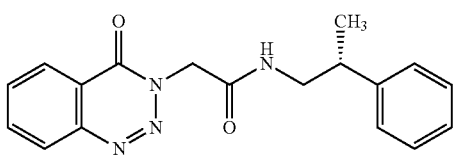 [SMILES: C[C@@H](CNC(=O)Cn1nnc2ccccc2c1=O)c1ccccc1]

The title compound was prepared in a manner similar to Example 2 using 2-(4-oxobenzo[d][1,2,3]triazin-3(4H)-yl)acetic acid and (R)-2-phenylpropan-1-amine to give the title compound as a white solid (13.1 mg, 56%). $^1$H NMR (500 MHz, DMSO-d$_6$) δ ppm 1.20 (d, J=6.8 Hz, 3 H), 2.86-2.93 (m, 1 H), 3.22-3.26 (m, 2 H), 4.99 (s, 2 H), 7.17-7.34 (m, 5 H), 7.96 (td, J=7.6, 1.5 Hz, 1 H), 8.12 (ddd, J=8.4, 7.2, 1.5 Hz, 1 H), 8.22-8.29 (m, 2 H), 8.36 (t, J=5.9 Hz, 1 H); ESI-MS m/z [M+H]$^+$ 323.0.

EXAMPLE 81

N-(2-chloro-4-methoxyphenethyl)-2-(4-oxobenzo[d][1,2,3]triazin-3(4H)-yl)acetamide

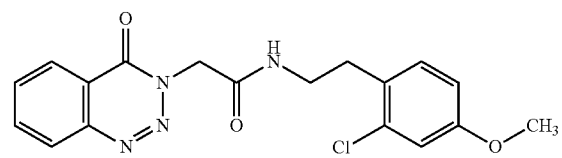 [SMILES: COc1ccc(CCNC(=O)Cn2nnc3ccccc3c2=O)c(Cl)c1]

The title compound was prepared in a manner similar to Example 2 using 2-(4-oxobenzo[d][1,2,3]triazin-3(4H)-yl)acetic acid and 2-(2-chloro-4-methoxyphenyl)ethanamine to give the title compound as a white solid (16.6 mg, 61%). $^1$H NMR (500 MHz, DMSO-d$_6$) δ ppm 2.78 (t, J=7.3 Hz, 2 H), 3.25-3.30 (m, 2 H), 3.31 (s, 2 H), 3.75 (s, 3 H), 4.99 (s, 2 H), 6.87 (dd, J=8.5, 2.7 Hz, 1 H), 7.01 (d, J=2.9 Hz, 1 H), 7.21-7.27 (m, 1 H), 7.93-8.00 (m, 1 H), 8.09-8.16 (m, 1 H), 8.22-8.30 (m, 2 H), 8.42 (t, J=5.6 Hz, 1 H); ESI-MS m/z [M, M+2]$^+$ 373.0, 374.9.

EXAMPLE 82

(R)—N-(1-(4-methoxyphenyl)propan-2-yl)-2-(4-oxobenzo[d][1,2,3]triazin-3(4H)-yl)acetamide

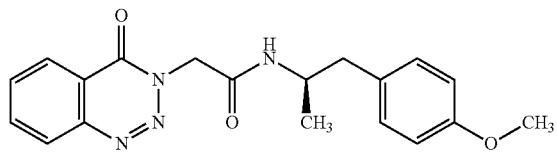 [SMILES: COc1ccc(C[C@@H](C)NC(=O)Cn2nnc3ccccc3c2=O)cc1]

The title compound was prepared in a manner similar to Example 2 using 2-(4-oxobenzo[d][1,2,3]triazin-3(4H)-yl) acetic acid and (R)-1-(4-methoxyphenyl)propan-2-amine to give the title compound as a white solid (17.9 mg, 70%). $^1$H NMR (500 MHz, DMSO-d$_6$) δ ppm 1.03 (d, J=6.8 Hz, 3 H), 2.53-2.72 (m, 2 H), 3.70-3.74 (m, 3 H), 3.91 (spt, J=6.8 Hz, 1 H), 4.92-5.02 (m, 2 H), 4.97 (d, J=4.9 Hz, 2 H), 6.79-6.88 (m, 2 H), 7.09-7.15 (m, 2 H), 7.92-8.00 (m, 1 H), 8.12 (ddd, J=8.4, 7.2, 1.5 Hz, 1 H), 8.22-8.30 (m, 3 H); ESI-MS m/z [M+H]$^+$ 354.0.

EXAMPLE 83

(S)-N-(1-(4-methoxyphenyl)propan-2-yl)-2-(4-oxobenzo[d][1,2,3]triazin-3 (4H)-yl)acetamide

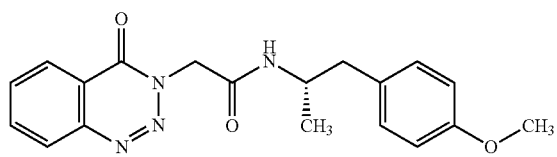 [SMILES: COc1ccc(C[C@H](C)NC(=O)Cn2nnc3ccccc3c2=O)cc1]

The title compound was prepared in a manner similar to Example 2 using 2-(4-oxobenzo[d][1,2,3]triazin-3(4H)-yl) acetic acid and (S)-1-(4-methoxyphenyl)propan-2-amine to give the title compound as a white solid (14.1 mg, 55%). $^1$H NMR (500 MHz, DMSO-d$_6$) δ ppm 1.03 (d, J=6.8 Hz, 3 H), 2.53-2.74 (m, 2 H), 3.70-3.74 (m, 3 H), 3.88-3.96 (m, 1 H), 4.92-5.02 (m, 2 H), 6.81-6.88 (m, 2 H), 7.08-7.16 (m, 2 H), 7.96 (ddd, J=8.1, 7.1, 1.5 Hz, 1 H), 8.12 (td, J=7.6, 1.5 Hz, 1 H), 8.22-8.30 (m, 3 H); ESI-MS m/z [M+H]$^+$ 353.9.

EXAMPLE 84

(S)-N-(1-(4-chloro-2-methoxyphenyl)propan-2-yl)-2-(4-oxobenzo[d][1,2,3]triazin-3 (4H)-yl)acetamide

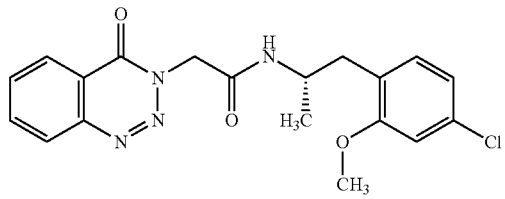 [SMILES: COc1cc(Cl)ccc1C[C@H](C)NC(=O)Cn1nnc2ccccc2c1=O]

The title compound was prepared in a manner similar to Example 2 using 2-(4-oxobenzo[d][1,2,3]triazin-3(4H)-yl) acetic acid and (S)-1-(4-chloro-2-methoxyphenyl)propan-2-amine to give the title compound as a white solid (19.7 mg, 70%). $^1$H NMR (500 MHz, DMSO-d$_6$) δ ppm 1.03 (d, J=6.8 Hz, 3 H), 2.67 (d, J=6.8 Hz, 2 H), 3.78-3.82 (m, 3 H), 3.97-4.07 (m, 1 H), 4.89-4.99 (m, 2 H), 6.92 (dd, J=7.8, 2.0 Hz, 1 H), 7.01 (d, J=2.0 Hz, 1 H), 7.14 (d, J=8.3 Hz, 1 H), 7.93-7.99 (m, 1 H), 8.12 (td, J=7.6, 1.5 Hz, 1 H), 8.20 (d, J=7.8 Hz, 1 H), 8.22-8.28 (m, 2 H); ESI-MS m/z [M, M+2]$^+$ 386.9, 389.0.

EXAMPLE 85

(S)-N-(1-(2-chloro-4-methoxyphenyl)propan-2-yl)-2-(4-oxobenzo[d][1,2,3]triazin-3(4H)-yl)acetamide

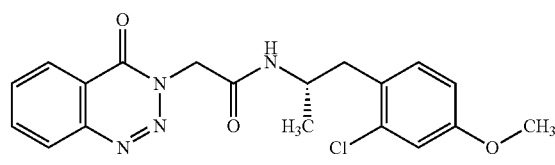 [SMILES: COc1ccc(C[C@H](C)NC(=O)Cn2nnc3ccccc3c2=O)c(Cl)c1]

The title compound was prepared in a manner similar to Example 2 using 2-(4-oxobenzo[d][1,2,3]triazin-3(4H)-yl) acetic acid and (S)-1-(2-chloro-4-methoxyphenyl)propan-2-amine, HCl to give the title compound as a tan solid (32.5 mg, 36%). $^1$H NMR (500 MHz, DMSO-d$_6$) δ ppm 1.07 (d, J=6.8 Hz, 3 H), 2.75-2.78 (m, 2 H), 3.75 (s, 3 H), 3.99-4.09 (m, 1 H), 4.89-5.02 (m, 2 H), 6.86 (dd, J=8.5, 2.7 Hz, 1 H), 6.99 (d, J=2.4 Hz, 1 H), 7.22-7.27 (m, 1 H), 7.96-7.99 (m, 1 H), 8.12 (ddd, J=8.4, 7.2, 1.5 Hz, 1 H), 8.21-8.31 (m, 3 H); ESI-MS m/z [M, M+2]$^+$ 386.9, 388.9.

EXAMPLE 86

(S)-2-(4-oxobenzo[d][1,2,3]triazin-3 (4H)-yl)-N-(1-(4-(trifluoromethoxy)phenyl)propyl)acetamide

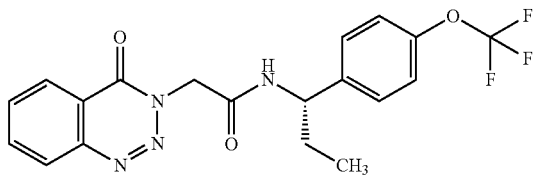 [SMILES: CC[C@H](NC(=O)Cn1nnc2ccccc2c1=O)c1ccc(OC(F)(F)F)cc1]

A mixture of 2-(4-oxobenzo[d][1,2,3]triazin-3(4H)-yl) acetic acid (23 mg, 0.11 mmol), (S)-1-(4-(trifluoromethoxy) phenyl)propan-1-amine hydrochloride (31.5 mg, 0.12 mmol), N-ethyl-N-isopropylpropan-2-amine (0.059 mL, 0.336 mmol), N1-((ethylimino)methylene)-N3,N3-dimethylpropane-1,3-diamine hydrochloride (26 mg, 0.135 mmol) and 1H-benzo[d][1,2,3] triazol-1-ol (18 mg, 0.135 mmol) in DMF (1 mL) was stirred at room temperature for 3 hours. The residue was diluted with MeOH then purified via HPLC Method A to provide the title compound as an off-white solid (16 mg, 35%). $^1$H NMR (500 MHz, chloroform-d) δ ppm 0.86-0.97 (m, 3 H) 1.79-1.91 (m, 2 H) 4.87-4.96 (m, 1 H) 5.13 (s, 2 H) 6.20-6.28 (m, 1 H) 7.14-7.20 (m, 2 H) 7.30-7.34 (m, 2 H) 7.80-7.89 (m, 1 H) 7.96-8.02 (m, 1 H) 8.17-8.26 (m, 1 H) 8.36-8.40 (m, 1 H); ESI-MS m/z [M+H]$^+$ 407.

EXAMPLE 87

(S)-2-(4-oxobenzo[d][1,2,3]triazin-3 (4H)-yl)-N-(1-(4-(trifluoromethyl)phenyl)propyl)acetamide

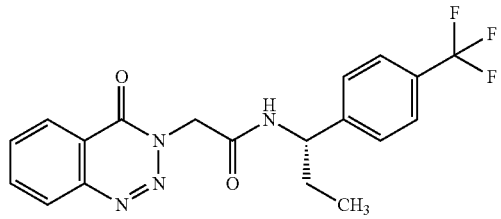 [SMILES: CC[C@H](NC(=O)Cn1nnc2ccccc2c1=O)c1ccc(C(F)(F)F)cc1]

The title compound was prepared in a manner similar to Example 87 using (S)-1-(4-(trifluoromethyl)phenyl)propan-1-amine hydrochloride to give the title compound as an off-white solid (19 mg, 56%). $^1$H NMR (500 MHz, chloroform-d) δ ppm 0.92 (t, J=7.1 Hz, 3 H) 1.86 (t, J=7.3 Hz, 2 H) 4.95 (d, J=7.3 Hz, 1 H) 5.13 (s, 2 H) 6.31 (d, J=7.8 Hz, 1 H) 7.40 (d, J=7.8 Hz, 2 H) 7.59 (d, J=7.8 Hz, 2 H) 7.86 (d, J=8.3 Hz, 1 H) 8.00 (s, 1 H) 8.21 (d, J=8.3 Hz, 1 H) 8.38 (d, J=7.8 Hz, 1 H); ESI-MS m/z [M+H]$^+$ 391.

The compounds of the invention can be administered alone or in the form of a pharmaceutical composition. In practice, the compounds of the invention are usually administered in the form of pharmaceutical compositions, that is, in admixture with at least one pharmaceutically acceptable excipient. The proportion and nature of any pharmaceutically acceptable excipient(s) are determined by the properties of the selected compound of the invention, the chosen route of administration, and standard pharmaceutical practice.

In another embodiment, the present invention provides pharmaceutical compositions comprising: a compound of invention and at least one pharmaceutically acceptable excipient.

In effecting treatment of a patient in need of such treatment, a compound of the invention can be administered in any form and route which makes the compound bioavailable. The compounds of the invention can be administered by a variety of routes, including orally, in particular by tablets and capsules. The compounds of the invention can be administered by parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present invention are prepared in a manner well known in the pharmaceutical art and include at least one of the compounds of the invention as the active ingredient. The amount of a compound of the invention may be varied depending upon its particular form and may conveniently be between 1% to about 50% of the weight of the unit dose form. The term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The present pharmaceutical compositions are preferably formulated in a unit dose form, each dose typically containing from about 0.5 mg to about 100 mg of a compounds of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage, typically on a daily schedule.

In one particular variation, the composition is a pharmaceutical composition adapted for oral administration, such as a tablet or a capsule or a liquid formulation, for example, a solution or suspension, adapted for oral administration. In still another particular variation, the pharmaceutical composition is a liquid formulation adapted for parenteral administration.

In another embodiment, the invention provides a method of treating a disease, disorder or condition associated with GPR139, comprising: administering to a patient in need thereof an effective amount of a compound of the invention. In another embodiment, a compound of the invention is provided for use as a medicament. The invention also provides the use of a compound of the invention, including the use for the manufacture of a medicament, to treat a disease, disorder or condition associated with GPR139 described herein. The compounds of the invention are GPR139 agonists for treating a variety of subjects (e.g., humans, non-human mammals and non-mammals).

As used herein terms "condition," "disorder," and "disease" relate to any unhealthy or abnormal state. The compounds of the invention are GPR139 agonists and may be useful for treating a variety of conditions. The term "disease, disorder or condition associated with GPR139" includes conditions, disorders, and diseases in which an agonist of GPR139 may provide a therapeutic benefit, such as CNS disorders, disorders of the pancreas, such as pancreatitis, phenylketonuria, and pituitary disorders.

The term "disease, disorder or condition associated with GPR139" includes specifically, but is not limited to, CNS disorders such as schizophrenia, autism spectrum disorder, sleep disorders, depression, bipolar disorder, cognitive impairment, including mild cognitive impairment, Alzheimer's Disease, disorders affecting short term memory, disorders affecting long term memory, attention deficit hyperactivity disorder, post-traumatic stress disorder, substance abuse, drug addiction, eating disorders, obsessive compulsive disorder, anxiety disorders, including generalized anxiety disorder and social anxiety disorder, pain, fibromyalgia and other disorders mentioned herein, among others.

Schizophrenia is a chronic, severe, and disabling disorder characterized, in part, by negative symptoms, such as blunted affect, deficits in social functioning, anhedonia, avolition and poverty of speech, and by cognitive impairment associated with schizophrenia (CIAS), such as impairment in attention, working memory, executive function and social cognition. Autism spectrum disorder is a group of developmental disabilities that can cause significant social, communication and behavioral challenges (repetitive and stereotyped behavior). Because of the pro-social effects expected from GPR139 agonists, the present compounds may treat schizophrenia and autism spectrum disorder.

In particular, the term "disease, disorder or condition associated with GPR139" includes schizophrenia.

In particular, the term "disease, disorder or condition associated with GPR139" includes autism spectrum disorder.

In particular, the term "disease, disorder or condition associated with GPR139" includes addiction. Examples include addiction to nicotine, alcohol, and/or cocaine.

In particular, the term "disease, disorder or condition associated with GPR139" includes attention deficit hyperactivity disorder.

In particular, the term "disease, disorder or condition associated with GPR139" includes bipolar disorder.

In particular, the term "disease, disorder or condition associated with GPR139" includes depression, such as major depressive disorder.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound of the invention which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. An effective amount of the present invention, the treatment dosage, is expected to range from 1 mg to 100 mg. Specific amounts can be determined by the skilled person. Although these dosages are based on an average human subject having a mass of about 60 kg to about 70 kg, the physician will be able to determine the appropriate dose for a patient having a mass that falls outside of this weight range.

The compounds of the invention may be combined with one or more other pharmacologically active compounds or therapies for the treatment of one or more disorders, diseases or conditions for which GPR139 is indicated may be administered simultaneously, sequentially or separately in combination with one or more compounds or therapies for treating a particular disease, disorder or condition associated with GPR139.

For example, in the treatment of schizophrenia the compounds of the invention may be administered in combination with sedatives, hypnotics, anxiolytics, antipsychotics, anti-anxiety agents, cyclopyrrolones, imidazopyridines, pyrazolopyrimidines, minor tranquilizers, melatonin agonists and antagonists, melatonergic agents, benzodiazepines, barbiturates, mGlu2/3 agonists, 5HT-2 antagonists, PDE10 antagonists, GlyT1 inhibitors, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and the like.

Also for example, in the treatment of depression the compounds of the invention may be administered in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical anti-depressants, benzodiazopines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazopam, chlorazepate, diazopam, halazepam, lorazepam, oxazopam and prazepam; buspirone, flesinoxan, gepirone and ipsapirone, and the like.

In yet another example, in the treatment of Alzheimer's disease or mild cognitive impairment the compounds of the invention may be administered in combination with anti-Alzheimer's agents, beta-secretase inhibitors, gamma-secretase inhibitors, HMG-CoA reductase inhibitors, NSAID's including ibuprofen, vitamin E, anti-amyloid antibodies, also sedatives, hypnotics, anxiolytics, antipsychotics, anti-anxiety agents, and tranquilizers, and such other medications as are used in the treatment of Alzheimer's disease or mild cognitive impairment.

The activity of compounds as GPR139 agonists may be determined by a variety of methods, including in vitro and in vivo methods.

EXAMPLE A

GPR139 Competition Binding

This membrane based assay measures the ability of compounds to competitively bind GPR139 in stably transfected CHO-TRex membranes. CHO-TRex (Life Technologies) cells were stably expressed with human GPR139 receptor, whose expression is controlled by a tetracycline inducible element. The cells were cultured in medium containing F12K, 10% Tetracycline free FBS, 1% Penn/Strep, 200 µg/mL Hygromycin. GPR139 receptor expression was induced for 18 hrs with 1 µg/mL doxycycline (Sigma D9891) in growth media. After addition of doxycycline, cells were harvested in PBS and pelleted by centrifugation for 5 minutes at 200×G. Liquid was aspirated off and cells were resuspended in ice cold Lysis buffer (20 mM HEPES/5 mM EDTA pH 7.4/1× Roche protease inhibitor). Samples were vortexed until homogenous and then placed on ice and homogenized using Dounce homogenizer on 50% power 3 separate times for 10 strokes each time. Lysate was centrifuged at 4° C. for 10 minutes in a tabletop Sorvall at 2000×G and supernatant was recovered and centrifuged in a Sorvall Ultracentrifuge at 35,000 rpm for 30 minutes at 4° C. The supernatant was discarded and the remaining pellet resuspended in Lysis buffer (20 mM HEPES/0.1 mM EGTA/Roche protease inhibitor). Membrane protein concentration was determined using ThermoFisher BCA quantification kit and aliquoted into microtubes. Tubes were snap frozen in LN2 and stored at −80° C.

Membranes were removed from −80° C., thawed and diluted in cold radioligand assay buffer (20 mM HEPES pH 7.4/5 mM MgCl$_2$/1 mM CaCl$_2$/Roche protease inhibitor). Compounds suspended in DMSO were diluted in 1 nM (S)-N-(1-(2-[$^3$H]-4-methoxyphenyl)propan-2-yl)-2-(2,3-dimethyl-7-oxothieno[2,3-d]pyridazin-6(7H)-yl)acetamide, readily prepared from (S)-N-(1-(2-chloro-4-hydroxyphenyl)propan-2-yl)-2-(2,3-dimethyl-7-oxothieno[2,3-d]pyridazin-6(7H)-yl)acetamide (20 mM HEPES pH 7.4/5 mM MgCl$_2$/1 mM CaCl$_2$/Roche protease inhibitor fresh/(S)-N-(1-(2-chloro-4-methoxyphenyl)propan-2-yl)-2-(2,3-dimethyl-7-oxothieno[2,3-d]pyridazin-6(7H)-yl)acetamide) in a 0.3 mL 96 well polypropylene assay plate (Fisher Scientific). Membranes (10 µg) were added to the assay plate, spun for 30 seconds at 300 rpm in a tabletop Eppendorf centrifuge, and then incubated at room temperature for 20 minutes. Filtermat A (Perkin Elmer No. 1450-421) is pre-soaked in 0.5% PEI (Sigma P3143) for 3 hours and dried at room temperature overnight. The contents of the assay plate were transferred to Filtermat A (Perkin Elmer No. 1450-421) using Tomtec harvester and washed 5 times with cold wash buffer (Tris-HCl pH 7.5). Filtermats were dried using a microwave oven and placed in sample bags (Perkin Elmer No. 1450-432) with scintillator sheets (Perkin Elmer No. 1450-411). Scintillator sheets were melted to filtermats using a heat block set to 65° C., placed in MicroBeta cartridges and read using the MicroBeta scintillation counter. Binding Ki curves were generated with a four-parameter logistic equation using GraphPad Prism 6. Table A provides results for the exemplified compounds in Example A.

TABLE A

GPR139 Inhibition (Ki (nM)) for Example (Ex) Compounds

| EX | Ki |
|---|---|
| 1 | 1621 |
| 2 | 119 |
| 3 | 48 |
| 4 | NT |
| 5 | 467 |
| 6 | NT |
| 7 | 1362 |
| 8 | 228 |
| 9 | 63 |
| 10 | 1148 |
| 11 | 953 |
| 12 | 2644 |
| 13 | 148 |
| 14 | 182 |
| 15 | 909 |
| 16 | 708 |
| 17 | 3601 |
| 18 | 58 |
| 19 | 189 |
| 20 | 551 |
| 21 | 173 |
| 22 | 110 |
| 23 | 842 |
| 24 | 72 |
| 25 | 526 |
| 26 | 26 |
| 27 | 190 |
| 28 | 179 |
| 29 | 915 |
| 30 | 791 |
| 31 | 4188 |
| 32 | 459 |
| 33 | 4850 |
| 34 | 347 |
| 35 | 1517 |
| 36 | 437 |
| 37 | 1466 |
| 38 | 619 |
| 39 | 92 |
| 40 | 533 |
| 41 | 10 |
| 42 | 179 |
| 43 | 435 |
| 44 | 2531 |
| 45 | 85 |
| 46 | 1562 |
| 47 | NT |
| 48 | NT |
| 49 | NT |
| 50 | NT |
| 51 | NT |
| 52 | 39 |
| 53 | 171 |
| 54 | 77 |
| 55 | 42 |
| 56 | 218 |
| 57 | 128 |
| 58 | 33 |
| 59 | 375 |
| 60 | 115 |
| 61 | 26 |
| 62 | 240 |
| 63 | 352 |
| 64 | 106 |
| 65 | 152 |
| 66 | 677 |
| 67 | 11 |
| 68 | 282 |

TABLE A-continued

GPR139 Inhibition (Ki (nM)) for Example (Ex) Compounds

| EX | Ki |
|---|---|
| 69 | 120 |
| 70 | 120 |
| 71 | 93 |
| 72 | 33 |
| 73 | NT |
| 74 | 1236 |
| 75 | 1688 |
| 76 | 5553 |
| 77 | NT |
| 78 | NT |
| 79 | NT |
| 80 | 4448 |
| 81 | 117 |
| 82 | NT |
| 83 | 802 |
| 84 | NT |
| 85 | NT |
| 86 | 183 |
| 87 | 214 |

EXAMPLE B

Activation of Calcium Signaling of GPR139 In Vitro Assay

This cell based assay measures the ability of compounds to activate GPR139 in stably transfected CHO-TRex cells. CHO-TRex (Life Technologies) cells were stably expressed with human GPR139 receptor, whose expression is controlled by a tetracycline inducible element. The cells were cultured in medium containing F12K, 10% Tetracycline free FBS, 1% Penn/Strep, 200 µg/mL Hygromycin. GPR139 receptor expression was induced for 18 hours with 1 µg/mL doxycycline (Sigma D9891) in growth media. After addition of doxycycline, cells were plated at a density of 30,000 cells per well in black 96 well clear bottom plates (Costar) and placed in an incubator (37°, 5% $CO_2$) for 18 hours prior to calcium assays.

Culture media was removed from cells and 200 µL of Calcium 5 dye (30 mL 1×HBSS/20 mM Hepes pH 7.4, 1 mM probenecid/vial Molecular Devices Calcium 5 dye) was added to cells and incubated for 40 min at 37° C. and 5% $CO_2$. Compounds suspended in DMSO were diluted in 1×HBSS 20 mM Hepes buffer pH7.4. After incubation, cells were incubated for 15 min at room temperature. Compounds were added to cells using the FLIPR Tetra (Molecular Devices) and fluorescence measured continuously for 1 minute. $EC_{50}$ curves were generated with a four-parameter logistic equation using GraphPad Prism 6. The specific compounds of this invention had an $EC_{50}$ value of less than about 100 micromolar. Table B provides results for the exemplified compounds in Example B.

EXAMPLE C

Balb/c Social Interaction Test

Young Balb/c mice show a natural deficit in sociable behaviors when put in a laboratory situation exposing them to an unfamiliar or "stimulus" mouse of a different strain. Social withdrawal or flattening of social behaviors is a feature of several disorders including schizophrenia and autism. Therefore this natural deficit seen in BalbC mice may be used (as a pre-clinical, non-pharmacologically induced model) to test potential pro-social effects of compounds intended to be used to treat the social aspects of disorders.

Methods: Balb/c male mice (4-5 weeks old) are acclimatized to the study room prior to start of the session (1 hour). Animals (n=15/group) are then dosed with vehicle (10 mL/mg) or test compound. After dosing, mice are returned to their home cage for the appropriate pre-treatment time. Following this, mice are placed individually into the center area of the Social Interaction (SI) box and allowed to explore freely for 5 minutes to habituate. They are then removed and the age-matched stimulus C57BL/6 mouse is placed in an enclosed stimulus Perspex cylinder in either the far left area or the far right area of the SI box. As soon as the stimulus C57BL/6 mouse is placed in the SI box the test mouse will be placed back into the center chamber and allowed to run freely around for a further 5 minutes. The activity of the test mouse is automatically monitored via Panlab's SMART tracking software throughout. The scoring (blinded to treatment) of sniffing interactions with either the stimulus cylinder or empty cylinder is manually recorded. Sniffing index (time sniffing stimulus cylinder-empty cylinder/time spent sniffing stimulus cylinder+empty cylinder) is used as the key measure of sociable behavior. Table C provides results for the exemplified compounds in Example C.

TABLE B

GPR139 Activation of Calcium Signaling ($EC_{50}$ (nM)) for Example (Ex) Compounds

| EX | $EC_{50}$ |
|---|---|
| 1 | 54 |
| 2 | 22 |
| 3 | 24 |
| 4 | 24 |
| 5 | 9 |
| 6 | 7 |
| 7 | NT |
| 8 | 33 |
| 9 | 15 |
| 10 | 27 |
| 11 | 24 |
| 12 | 67 |
| 13 | 91 |
| 14 | 11 |
| 15 | 16 |
| 16 | 9 |
| 17 | 27 |
| 18 | 10 |
| 19 | 13 |
| 20 | 16 |
| 21 | 17 |
| 22 | 7 |
| 23 | 13 |
| 24 | 9 |
| 25 | 8 |
| 26 | 16 |
| 27 | 7 |
| 28 | 10 |
| 29 | 19 |
| 30 | 30 |
| 31 | 39 |
| 32 | 16 |
| 33 | 41 |
| 34 | 7 |
| 35 | 42 |
| 36 | 19 |
| 37 | 70 |
| 38 | 26 |
| 39 | 6 |
| 40 | 9 |
| 41 | 7 |
| 42 | 37 |
| 43 | 45 |
| 44 | 15 |
| 45 | 36 |
| 46 | 11 |
| 47 | 14 |

TABLE B-continued

GPR139 Activation of Calcium Signaling (EC50 (nM)) for Example (Ex) Compounds

| EX | EC$_{50}$ |
|---|---|
| 48 | 1514 |
| 49 | 22 |
| 50 | 52 |
| 51 | 16 |
| 52 | 24 |
| 53 | 33 |
| 54 | |
| 55 | 38 |
| 56 | 37 |
| 57 | 43 |
| 58 | 22 |
| 59 | 51 |
| 60 | 18 |
| 61 | 15 |
| 62 | 25 |
| 63 | 50 |
| 64 | 13 |
| 65 | 21 |
| 66 | 18 |
| 67 | 20 |
| 68 | 10 |
| 69 | 17 |
| 70 | 29 |
| 71 | 49 |
| 72 | 49 |
| 73 | 1303 |
| 74 | 21 |
| 75 | 65 |
| 76 | 30 |
| 77 | NT |
| 78 | 80 |
| 79 | NT |
| 80 | 288 |
| 81 | 117 |
| 82 | NT |
| 83 | 802 |
| 84 | NT |
| 85 | NT |
| 86 | 50 |
| 87 | 31 |

TABLE C

Sniffing Index for Balb/c Social Interaction Test

| Test Compound | Dose | | Sniffing Index | SEM |
|---|---|---|---|---|
| Vehicle | 10 | mL/mg | 0.3449 | 0.08677 |
| Example 2 | 0.03 | mg/kg | 0.5363 | 0.07839 |
| | 0.3 | mg/kg | 0.6023 | 0.06546 |
| | 3.0 | mg/kg | 0.6116 | 0.05989 |
| Vehicle | 10 | mL/mg | 0.1299 | 0.06292 |
| Example 3 | 0.01 | mg/kg | 0.2790 | 0.08543 |
| | 0.03 | mg/kg | 0.5185 | 0.07124 |
| | 0.1 | mg/kg | 0.4957 | 0.05945 |
| Vehicle | 10 | mL/mg | 0.1817 | 0.1041 |
| Example 5 | 0.3 | mg/kg | 0.4715 | 0.05589 |
| | 3 | mg/kg | 0.5756 | 0.1085 |
| | 30 | mg/kg | 0.6701 | 0.04847 |
| Vehicle | 10 | mL/mg | 0.2595 | 0.1788 |
| Example 13 | 0.03 | mg/kg | 0.6017 | 0.05771 |
| | 0.3 | mg/kg | 0.7280 | 0.04914 |
| | 3 | mg/kg | 0.2621 | 0.1557 |
| Vehicle | 10 | mL/mg | 0.3016 | 0.1127 |
| Example 18 | 0.03 | mg/kg | 0.4742 | 0.06643 |
| | 0.1 | mg/kg | 0.5100 | 0.1090 |
| | 0.3 | mg/kg | 0.6531 | 0.05789 |
| | 30 | mg/kg | 0.6481 | 0.07488 |

EXAMPLE D

Poly(I:C) Social Interaction Test

Mice are social animals. Disturbance of social approach and avoidance are disabling symptoms of social phobia, social anxiety, autism, schizophrenia, and depression which may be modeled in mice. The Poly(I:C) Social Interaction Test is based on the free choice by a subject mouse to spend time interacting with an unfamiliar mouse or empty cylinder. Offspring from GD17 Poly(I:C) treated mothers show a deficit in social interaction in this test as compared to offspring from vehicle injected mothers. The reversal of this deficit may be used to test the potential pro-social effects of compounds intended to be used to treat the social aspects of disorders.

Methods: C57BL/6 mice (~14-16 weeks old) of Poly(I:C) or vehicle treated mothers are acclimatized to the study room prior to start of the session (1 hour). Animals are then dosed with vehicle (10 mL/kg) or test compound (n=12/group). After dosing, mice are returned to their home cage for the appropriate compound pre-treatment time (acute or pre-treated for 13 days before standard acute test was performed). Following this, mice are placed individually into the centre area of the SI box and allowed to explore freely for 2 minutes to habituate. The age-matched stimulus C57BL/6 mouse is then placed in an enclosed stimulus Perspex cylinder in either the far left area or the far right area of the SI box. The test mouse may then explore freely for a further 5 minutes. The activity of the test mouse is automatically monitored via Panlab's SMART tracking software throughout. The scoring (blinded to treatment) of sniffing interactions with either the stimulus cylinder or empty cylinder is manually recorded. Sniffing index (time sniffing stimulus cylinder-empty cylinder/time spent sniffing stimulus cylinder+empty cylinder) is used as the key measure of sociable behavior.

TABLE D

Sniffing Index for Poly(I:C) Social Interaction Test

| Test Compound | Offspring Tested | Dose | | Sniffing Index | SEM |
|---|---|---|---|---|---|
| Vehicle | Vehicle | 10 | mL/kg | 0.6940 | 0.03800 |
| Vehicle | Poly(I:C) | 10 | mL/kg | 0.3347 | 0.09289 |
| Example 2 | Poly(I:C) | 0.01 | mg/kg | 0.3906 | 0.07594 |
| Example 2 | Poly(I:C) | 0.1 | mg/kg | 0.6183 | 0.04157 |
| Example 2 | Poly(I:C) | 1.0 | mg/kg | 0.5794 | 0.04119 |
| Vehicle* | Vehicle | 10 | mL/kg | 0.7085 | 0.03369 |
| Vehicle* | Poly(I:C) | 10 | mL/kg | 0.3321 | 0.08627 |
| Vehicle*/Example 2 | Poly(I:C) | 0.01 | mg/kg | 0.6308 | 0.04213 |
| Example 2*/Example 2 | Poly(I:C) | 0.1 | mg/kg | 0.5910 | 0.06561 |
| Vehicle | Vehicle | 10 | mL/kg | 0.6002 | 0.05238 |
| Example 5 | Vehicle | 30 | mg/kg | 0.6104 | 0.04409 |
| Vehicle | Poly(I:C) | 10 | mL/kg | 0.4103 | 0.06206 |
| Example 5 | Poly(I:C) | 0.3 | mg/kg | 0.5410 | 0.02821 |
| Example 5 | Poly(I:C) | 3 | mg/kg | 0.5897 | 0.05552 |
| Example 5 | Poly(I:C) | 30 | mg/kg | 0.6232 | 0.06749 |
| Vehicle | Vehicle | 10 | mL/kg | 0.6873 | 0.04139 |
| Vehicle | Poly(I:C) | 10 | mL/kg | 0.3263 | 0.05871 |
| Example 18 | Poly(I:C) | 0.3 | mg/kg | 0.5200 | 0.03283 |
| Example 18 | Poly(I:C) | 3 | mg/kg | 0.5276 | 0.04350 |
| Example 18 | Poly(I:C) | 30 | mg/kg | 0.5586 | 0.04619 |

*dosed for 13 days before test was performed

EXAMPLE E cFos Staining

To demonstrate target engagement in vivo, c-Fos immunoreactivity was measured in the dorsal medial habenula following oral dosing. Since GPR139 is Gq-coupled, dosing with present compounds induced c-Fos expression, a common signaling mechanism in activated neurons (Cohen & Greenberg, Ann. Rev. Cell Dev. Biol. (2008)).

Methods: After dosing C57/B16 mice for various time courses their brains were prepared for immunohistochemistry. One hour after the final oral dose is administered C57/B16 mice are perfused with 100 mL 4% paraformaldehyde in PBS. Brains are extracted and placed in 4% paraformaldehyde for 3 hours, changed into 20% sucrose/PBS solution to avoid freezing artifacts, and frozen with dry ice. Frozen brain sections are obtained with sliding microtome at 20 um and washed in PBS (2 times for 10 minutes each). Endogenous peroxidase enzyme is blocked with 0.3% $H_2O_2$ solution in water for 10 minutes. Sections are rinsed in PBS (3 times for 10 minutes each) and incubated in primary antibody against cFos (Santa Cruz SC-42) at a dilution of 1:10,000 at 4° C. overnight in PBS+0.3% triton and 1% bovine serum albumin. Sections are subsequently rinsed in PBS (3 times for 10 minutes each) and incubated in secondary antibody: goat against rabbit-biotinylated antibody, at a dilution of 1:200 for 1 hour at room temperature in PBS+0.3% triton and 1% bovine serum albumin. Sections are rinsed in PBS (3 times for 10 minutes each) and incubated in ABC mix in PBS: ABC Elite Kit from Vector (PK-1000) for 1 hour at room temperature. Next, the sections are rinsed in PBS (3 times for 10 minutes each) and then in 0.1 M sodium acetate (3 times for 10 minutes each). Reaction is visualized with standard diaminobenzydine procedures: 50 mL of 0.1M sodium acetate containing 20 mg ammonium chloride, 20 mg, diaminobenzydine, 80 mg glucose and 10 mL of glucose oxidase. React for 10 minutes then the reaction is stopped with PBS rinses (3 times for 10 minutes each). cFos cells are then counted. The cFos cell count is provided in Tables E.1, E.2, E.2, and E.4.

TABLE E.1 cFos cell count in desensitization experiment with Example 2

|  | vehicle 1 d | vehicle 10 d | 0.1 mg/kg 1 d | 0.1 mg/kg 5 d | 0.1 mg/kg 10 d |
| --- | --- | --- | --- | --- | --- |
| Number of mice | 5 | 5 | 5 | 5 | 5 |
| Mean | 352 | 450 | 1486 | 1928 | 1684 |
| Std. Deviation | 218.6 | 192.2 | 789.7 | 833.6 | 457.4 |
| SEM | 97.74 | 85.97 | 353.2 | 372.8 | 204.5 |

TABLE E.2 cFos cell count in dose response curve experiment with Example 2

|  | vehicle | 0.01 mg/kg | 0.03 mg/kg | 0.1 mg/kg | 0.3 mg/kg | 1 mg/kg |
| --- | --- | --- | --- | --- | --- | --- |
| Number of mice | 5 | 5 | 4 | 4 | 4 | 5 |
| Mean | 267 | 1376 | 986.3 | 1381 | 1408 | 1368 |
| Std. Deviation | 169.8 | 566.3 | 224.3 | 297.7 | 229.1 | 507.8 |
| SEM | 75.94 | 253.3 | 112.2 | 148.8 | 114.6 | 227.1 |
| Sum | 1335 | 6880 | 3945 | 5525 | 5630 | 6840 |

TABLE E.3 cFos cell count in time course experiment with Example 2

|  | vehicle | 0.1 mg/kg 1 hr | 0.3 mg/kg 1 hr | 3 mg/kg 1 hr | 0.3 mg/kg 2 hr | 0.3 mg/kg 4 hr |
| --- | --- | --- | --- | --- | --- | --- |
| Number of mice | 3 | 3 | 3 | 3 | 3 | 3 |
| Mean | 413.7 | 787.7 | 1343 | 2365 | 1400 | 2170 |
| Std. Deviation | 82.1 | 71.14 | 509.7 | 450.1 | 151 | 333.9 |
| SEM | 47.4 | 41.07 | 294.3 | 259.9 | 87.18 | 192.8 |

TABLE E.4 cFos cell count in dose-response and time course experiment with Example 3

|  | vehicle | 0.03 mg/kg 1 hr | 0.1 mg/kg 1 hr | 0.3 mg/kg 1 hr | 3 mg/kg 1 hr | 0.3 mg/kg 2 hr | 0.3 mg/kg 4 hr |
| --- | --- | --- | --- | --- | --- | --- | --- |
| Number of mice | 3 | 3 | 3 | 3 | 3 | 3 | 2 |
| Mean | 470 | 1628 | 2243 | 2458 | 2023 | 2777 | 865 |
| Std. Deviation | 78.58 | 272.8 | 712.9 | 167.7 | 383.7 | 1249 | 134.4 |
| SEM | 45.37 | 157.5 | 411.6 | 96.8 | 221.5 | 720.9 | 95 |

What is claimed is:

1. A method for agonizing GPR139 in a subject, the method comprising administering to the subject a compound of formula 2:

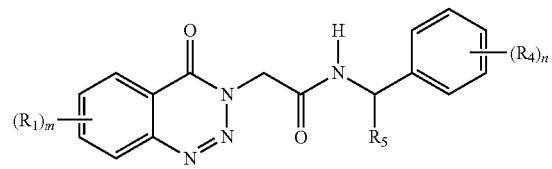

or a pharmaceutically acceptable salt thereof, wherein
m is selected from 0, 1, and 2;
n is selected from 0, 1, and 2;

each R₁ is independently selected from the group consisting of cyano, halo, hydroxy, amino, $C_{1-4}$ alkyl, $C_{1-4}$ alkoxy, trifluoromethyl, and trifluoromethoxy;

each R₄ is independently selected from the group consisting of cyano, halo, hydroxy, amino, $C_{1-4}$ alkyl, $C_{1-4}$ alkoxy, trifluoromethyl, fluoromethoxy, difluoromethoxy, and trifluoromethoxy; and R₅ is selected from the group consisting of hydrogen, trifluoromethyl, and $C_{1-4}$ alkyl, provided:
(a) if R₅ is hydrogen, methyl, n-propyl, i-propyl, or i-butyl, then m and n are not both 0;
(b) if R₅ is hydrogen, m is 0, and n is 1, then R₄ is not chloro, methoxy, 3-trifluoromethyl, 4-trifluoromethyl, 4-methyl, 4-fluoro, 2-difluoromethoxy, 3-difluoromethoxy, 2-trifluoromethoxy, 4-trifluoromethoxy, or 2-(i-butoxy);
(c) if R₅ is methyl, m is 0, and n is 1, then R₄ is not chloro, 2-fluoro, 4-fluoro, 2-bromo, 4-ethyl, 2-methyl, 4-(i-propyl), 4-(i-butyl), or 3-trifluoromethyl;
(d) if R₅ is ethyl, m is 0, and n is 1, then R₄ is not 3-chloro, 4-chloro, 4-bromo, 4-methyl, 4-methoxy, or 2-difluoromethoxy;
(e) if R₅ is n-propyl, m is 0, and n is 1, then R₄ is not 3-trifluoromethyl;
(f) if R₅ is i-propyl, m is 0, and n is 1, then R₄ is not 4-fluoro or 4-methoxy;
(g) if R₅ is i-butyl, m is 0, and n is 1, then R₄ is not 3-trifluoromethyl;
(h) if R₅ is hydrogen, m is 0, and n is 2, then R₄ is not 2,6-difluoro, 2,4-dichloro, 3,5-dimethoxy, 3,4-dimethoxy, 4-methoxy-3-difluoromethoxy, 4-fluoro-2-trifluoromethyl, or 5-bromo-2-difluormethoxy; and
(i) if R₅ is methyl, m is 0, and n is 2, then R₄ is not 3,4-dimethyl, 3,4-dichloro, 2,4-dichloro, 3-fluoro-4-methoxy, 3-bromo-4-methoxy, 3-methoxy-4-isopropyloxy, or 3-methoxy-4-isobutyloxy.

2. The method according to claim 1, wherein the compound is substantially enantiomerically pure and has a structure represented by formula 2A,

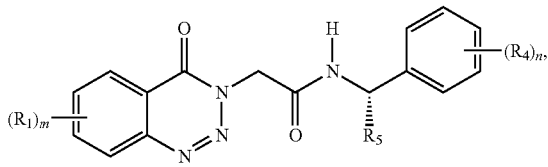

2A wherein R₅ is selected from the group consisting of trifluoromethyl and $C_{1-4}$ alkyl.

3. The method according to claim 1, wherein m is 0.

4. The method according to claim 1, wherein R₅ is $C_{1-4}$ alkyl.

5. The method according to claim 1, wherein R₅ is selected from the group consisting of methyl, ethyl, and isopropyl.

6. The method according to claim 1, wherein R₅ is methyl.

7. The method according to claim 1, wherein n is 1 and R₄ is trifluoromethoxy.

8. The method according to claim 1, wherein m is 1.

9. The method according to claim 1, wherein m is 2.

10. The method according to claim 1, wherein the compound is selected from the group of compounds consisting of:

2-(5-methoxy-4-oxobenzo[d][1,2,3]triazin-3(4H)-yl)-N-(1-p-tolylethyl)acetamide;
N-(1-(4-bromophenyl)ethyl)-2-(4-oxobenzo[d][1,2,3]triazin-3(4H)-yl)acetamide;
2-(4-oxobenzo[d][1,2,3]triazin-3(4H)-yl)-N-(1-p-tolylethyl)acetamide;
N-(1-(4-methoxyphenyl)ethyl)-2-(4-oxobenzo[d][1,2,3]triazin-3(4H)-yl)acetamide;
N-(1-(2,4-dimethylphenyl)ethyl)-2-(4-oxobenzo[d][1,2,3]triazin-3(4H)-yl)acetamide;
N-(1-(4-ethoxyphenyl)ethyl)-2-(4-oxobenzo[d][1,2,3]triazin-3(4H)-yl)acetamide;
N-(1-(2,4-dimethoxyphenyl)ethyl)-2-(4-oxobenzo[d][1,2,3]triazin-3(4H)-yl)acetamide;
2-(4-oxobenzo[d][1,2,3]triazin-3(4H)-yl)-N-(1-(4-(trifluoromethyl)phenyl)ethyl)acetamide;
2-(6-fluoro-4-oxobenzo[d][1,2,3]triazin-3(4H)-yl)-N-(1-p-tolylethyl)acetamide;
2-(6-fluoro-4-oxobenzo[d][1,2,3]triazin-3(4H)-yl)-N-(1-(4-methoxyphenyl)ethyl)acetamide;
2-(8-fluoro-4-oxobenzo[d][1,2,3]triazin-3(4H)-yl)-N-(1-p-tolylethyl)acetamide;
2-(8-fluoro-4-oxobenzo[d][1,2,3]triazin-3(4H)-yl)-N-(1-(4-methoxyphenyl)ethyl)acetamide;
2-(6-methoxy-4-oxobenzo[d][1,2,3]triazin-3(4H)-yl)-N-(1-p-tolylethyl)acetamide;
2-(6-chloro-4-oxobenzo[d][1,2,3]triazin-3(4H)-yl)-N-(1-p-tolylethyl)acetamide;
2-(6-chloro-4-oxobenzo[d][1,2,3]triazin-3(4H)-yl)-N-(1-(4-methoxyphenyl)ethyl)acetamide;
2-(7-chloro-4-oxobenzo[d][1,2,3]triazin-3(4H)-yl)-N-(1-p-tolylethyl)acetamide;
2-(8-chloro-4-oxobenzo[d][1,2,3]triazin-3(4H)-yl)-N-(1-p-tolylethyl)acetamide;
2-(8-chloro-4-oxobenzo[d][1,2,3]triazin-3(4H)-yl)-N-(1-(4-methoxyphenyl)ethyl)acetamide;
2-(8-methyl-4-oxobenzo[d][1,2,3]triazin-3(4H)-yl)-N-(1-p-tolylethyl)acetamide;
N-(1-(4-methoxyphenyl)ethyl)-2-(8-methyl-4-oxobenzo[d][1,2,3]triazin-3(4H)-yl)acetamide;
2-(6,8-dichloro-4-oxobenzo[d][1,2,3]triazin-3(4H)-yl)-N-(1-p-tolylethyl)acetamide;
2-(6,8-dichloro-4-oxobenzo[d][1,2,3]triazin-3(4H)-yl)-N-(1-(4-methoxyphenyl)ethyl)acetamide;
2-(6-methyl-4-oxobenzo[d][1,2,3]triazin-3(4H)-yl)-N-(1-p-tolylethyl)acetamide;
N-(1-(4-methoxyphenyl)ethyl)-2-(6-methyl-4-oxobenzo[d][1,2,3]triazin-3(4H)-yl)acetamide;
2-(8-methoxy-4-oxobenzo[d][1,2,3]triazin-3(4H)-yl)-N-(1-p-tolylethyl)acetamide;
2-(8-methoxy-4-oxobenzo[d][1,2,3]triazin-3(4H)-yl)-N-(1-(4-methoxyphenyl)ethyl)acetamide;
2-(5-fluoro-4-oxobenzo[d][1,2,3]triazin-3(4H)-yl)-N-(1-p-tolylethyl)acetamide;
2-(5-fluoro-4-oxobenzo[d][1,2,3]triazin-3(4H)-yl)-N-(1-(4-methoxyphenyl)ethyl)acetamide;
2-(7-methyl-4-oxobenzo[d][1,2,3]triazin-3(4H)-yl)-N-(1-p-tolylethyl)acetamide;
N-(1-(4-methoxyphenyl)ethyl)-2-(7-methyl-4-oxobenzo[d][1,2,3]triazin-3(4H)-yl)acetamide;
2-(7-methoxy-4-oxobenzo[d][1,2,3]triazin-3(4H)-yl)-N-(1-p-tolylethyl)acetamide;
2-(7-methoxy-4-oxobenzo[d][1,2,3]triazin-3(4H)-yl)-N-(1-(4-methoxyphenyl)ethyl)acetamide;
2-(5-methoxy-4-oxobenzo[d][1,2,3]triazin-3(4H)-yl)-N-(1-(4-methoxyphenyl)ethyl)acetamide;

N-(1-(4-methoxyphenyl)ethyl)-2-(5-methyl-4-oxobenzo[d][1,2,3]triazin-3(4H)-yl)acetamide;
2-(6,8-dimethyl-4-oxobenzo[d][1,2,3]triazin-3(4H)-yl)-N-(1-(4-methoxyphenyl)ethyl)acetamide;
2-(4-oxo-6-(trifluoromethyl)benzo[d][1,2,3]triazin-3(4H)-yl)-N-(1-p-tolylethyl)acetamide;
N-(1-(4-methoxyphenyl)ethyl)-2-(4-oxo-6-(trifluoromethyl)benzo[d][1,2,3]triazin-3(4H)-yl)acetamide;
2-(8-fluoro-6-methyl-4-oxobenzo[d][1,2,3]triazin-3(4H)-yl)-N-(1-(p-tolyl)ethyl)acetamide;
N-(1-(2-methoxy-4-methylphenyl)ethyl)-2-(4-oxobenzo[d][1,2,3]triazin-3(4H)-yl)acetamide;
N-(1-(2-bromo-4-fluorophenyl)ethyl)-2-(4-oxobenzo[d][1,2,3]triazin-3(4H)-yl)acetamide;
N-(1-(2-methoxy-4-methylphenyl)ethyl)-2-(4-oxobenzo[d][1,2,3]triazin-3(4H)-yl)propanamide;
N-(1-(2,4-dimethylphenyl)ethyl)-2-(6-fluoro-4-oxobenzo[d][1,2,3]triazin-3(4H)-yl)acetamide;
N-(1-(2-fluoro-4-methylphenyl)ethyl)-2-(4-oxobenzo[d][1,2,3]triazin-3(4H)-yl)acetamide;
N-(1-(2-fluoro-4-methylphenyl)ethyl)-2-(6-fluoro-4-oxobenzo[d][1,2,3]triazin-3(4H)-yl)acetamide;
2-(6-fluoro-4-oxobenzo[d][1,2,3]triazin-3(4H)-yl)-N-(1-(4-(trifluoromethoxy)phenyl)ethyl)acetamide;
2-(7-methoxy-4-oxobenzo[d][1,2,3]triazin-3(4H)-yl)-N-(1-(4-(trifluoromethoxy)phenyl)ethyl)acetamide;
2-(6-methoxy-4-oxobenzo[d][1,2,3]triazin-3(4H)-yl)-N-(1-(4-(trifluoromethoxy)phenyl)ethyl)acetamide;
2-(5-methoxy-4-oxobenzo[d][1,2,3]triazin-3(4H)-yl)-N-(1-(4-(trifluoromethoxy)phenyl)ethyl)acetamide;
2-(7-methoxy-4-oxobenzo[d][1,2,3]triazin-3(4H)-yl)-N-(1-(4-(trifluoromethyl)phenyl)ethyl)acetamide;
2-(6-methoxy-4-oxobenzo[d][1,2,3]triazin-3(4H)-yl)-N-(1-(4-(trifluoromethyl)phenyl)ethyl)acetamide;
2-(5-methoxy-4-oxobenzo[d][1,2,3]triazin-3(4H)-yl)-N-(1-(4-(trifluoromethyl)phenyl)ethyl)acetamide;
2-(8-methoxy-4-oxobenzo[d][1,2,3]triazin-3(4H)-yl)-N-(1-(4-(trifluoromethoxy)phenyl)ethyl)acetamide;
2-(8-methoxy-4-oxobenzo[d][1,2,3]triazin-3(4H)-yl)-N-(1-(4-(trifluoromethyl)phenyl)ethyl)acetamide;
2-(6-fluoro-4-oxobenzo[d][1,2,3]triazin-3(4H)-yl)-N-(1-(4-(trifluoromethyl)phenyl)ethyl)acetamide;
N-(1-(2-fluoro-4-(trifluoromethyl)phenyl)ethyl)-2-(4-oxobenzo[d][1,2,3]triazin-3(4H)-yl)acetamide;
N-(1-(4-(difluoromethoxy)phenyl)ethyl)-2-(4-oxobenzo[d][1,2,3]triazin-3(4H)-yl)acetamide;
N-(1-(2-fluoro-4-(trifluoromethyl)phenyl)ethyl)-2-(5-methoxy-4-oxobenzo[d][1,2,3]triazin-3(4H)-yl)acetamide;
N-(1-(4-(difluoromethoxy)phenyl)ethyl)-2-(6-fluoro-4-oxobenzo[d][1,2,3]triazin-3(4H)-yl)acetamide;
N-(1-(4-(difluoromethoxy)phenyl)ethyl)-2-(5-methoxy-4-oxobenzo[d][1,2,3]triazin-3(4H)-yl)acetamide;
N-(1-(2-fluoro-4-(trifluoromethoxy)phenyl)ethyl)-2-(4-oxobenzo[d][1,2,3]triazin-3(4H)-yl)acetamide;
N-(1-(2-fluoro-4-(trifluoromethoxy)phenyl)ethyl)-2-(6-fluoro-4-oxobenzo[d][1,2,3]triazin-3(4H)-yl)acetamide;
N-(1-(2-fluoro-4-(trifluoromethoxy)phenyl)ethyl)-2-(5-methoxy-4-oxobenzo[d][1,2,3]triazin-3(4H)-yl)acetamide; and
a pharmaceutically acceptable salt of any one of the above-mentioned compounds.

11. The method according to claim 1, wherein the compound is selected from the group of compounds consisting of:

(S)-2-(5-methoxy-4-oxobenzo[d][1,2,3]triazin-3(4H)-yl)-N-(1-p-tolylethyl)acetamide;
(S)-N-(1-(4-bromophenyl)ethyl)-2-(4-oxobenzo[d][1,2,3]triazin-3(4H)-yl)acetamide;
(S)-2-(4-oxobenzo[d][1,2,3]triazin-3(4H)-yl)-N-(1-p-tolylethyl)acetamide;
(R)-2-(4-oxobenzo[d][1,2,3]triazin-3(4H)-yl)-N-(1-p-tolylethyl)acetamide;
(S)-N-(1-(4-methoxyphenyl)ethyl)-2-(4-oxobenzo[d][1,2,3]triazin-3(4H)-yl)acetamide;
(S)-N-(1-(2,4-dimethylphenyl)ethyl)-2-(4-oxobenzo[d][1,2,3]triazin-3(4H)-l)acetamide;
(S)-N-(1-(4-ethoxyphenyl)ethyl)-2-(4-oxobenzo[d][1,2,3]triazin-3(4H)-yl)acetamide;
(S)-N-(1-(2,4-dimethoxyphenyl)ethyl)-2-(4-oxobenzo[d][1,2,3]triazin-3(4H)-yl)acetamide;
(S)-2-(6-fluoro-4-oxobenzo[d][1,2,3]triazin-3(4H)-yl)-N-(1-p-tolylethyl)acetamide;
(S)-2-(6-fluoro-4-oxobenzo[d][1,2,3]triazin-3(4H)-yl)-N-(1-(4-methoxyphenyl)ethyl)acetamide;
(S)-2-(8-fluoro-4-oxobenzo[d][1,2,3]triazin-3(4H)-yl)-N-(1-p-tolylethyl)acetamide;
(S)-2-(8-fluoro-4-oxobenzo[d][1,2,3]triazin-3(4H)-yl)-N-(1-(4-methoxyphenyl)ethyl)acetamide;
(S)-2-(6-methoxy-4-oxobenzo[d][1,2,3]triazin-3(4H)-yl)-N-(1-p-tolylethyl)acetamide;
(S)-2-(6-chloro-4-oxobenzo[d][1,2,3]triazin-3(4H)-yl)-N-(1-p-tolylethyl)acetamide;
(S)-2-(6-chloro-4-oxobenzo[d][1,2,3]triazin-3(4H)-yl)-N-(1-(4-methoxyphenyl)ethyl)acetamide;
(S)-2-(7-chloro-4-oxobenzo[d][1,2,3]triazin-3(4H)-yl)-N-(1-p-tolylethyl)acetamide;
(S)-2-(8-chloro-4-oxobenzo[d][1,2,3]triazin-3(4H)-yl)-N-(1-p-tolylethyl)acetamide;
(S)-2-(8-chloro-4-oxobenzo[d][1,2,3]triazin-3(4H)-yl)-N-(1-(4-methoxyphenyl)ethyl)acetamide;
(S)-2-(8-methyl-4-oxobenzo[d][1,2,3]triazin-3(4H)-yl)-N-(1-p-tolylethyl)acetamide;
(S)-N-(1-(4-methoxyphenyl)ethyl)-2-(8-methyl-4-oxobenzo[d][1,2,3]triazin-3(4H)-yl)acetamide;
(S)-2-(6,8-dichloro-4-oxobenzo[d][1,2,3]triazin-3(4H)-yl)-N-(1-p-tolylethyl)acetamide;
(S)-2-(6,8-dichloro-4-oxobenzo[d][1,2,3]triazin-3(4H)-yl)-N-(1-(4-methoxyphenyl)ethyl)acetamide;
(S)-2-(6-methyl-4-oxobenzo[d][1,2,3]triazin-3(4H)-yl)-N-(1-p-tolylethyl)acetamide;
(S)-N-(1-(4-methoxyphenyl)ethyl)-2-(6-methyl-4-oxobenzo[d][1,2,3]triazin-3(4H)-yl)acetamide;
(S)-2-(8-methoxy-4-oxobenzo[d][1,2,3]triazin-3(4H)-yl)-N-(1-p-tolylethyl)acetamide;
(S)-2-(8-methoxy-4-oxobenzo[d][1,2,3]triazin-3(4H)-yl)-N-(1-(4-methoxyphenyl)ethyl)acetamide;
(S)-2-(5-fluoro-4-oxobenzo[d][1,2,3]triazin-3(4H)-yl)-N-(1-(4-methoxyphenyl)ethyl)acetamide;
(S)-2-(7-methyl-4-oxobenzo[d][1,2,3]triazin-3(4H)-yl)-N-(1-p-tolylethyl)acetamide;
(S)-N-(1-(4-methoxyphenyl)ethyl)-2-(7-methyl-4-oxobenzo[d][1,2,3]triazin-3(4H)-yl)acetamide;
(S)-2-(7-methoxy-4-oxobenzo[d][1,2,3]triazin-3(4H)-yl)-N-(1-p-tolylethyl)acetamide;
(S)-2-(7-methoxy-4-oxobenzo[d][1,2,3]triazin-3(4H)-yl)-N-(1-(4-methoxyphenyl)ethyl)acetamide;
(S)-2-(5-methoxy-4-oxobenzo[d][1,2,3]triazin-3(4H)-yl)-N-(1-(4-methoxyphenyl)ethyl)acetamide;
(S)-N-(1-(4-methoxyphenyl)ethyl)-2-(5-methyl-4-oxobenzo[d][1,2,3]triazin-3(4H)-yl)acetamide;

(S)-2-(6, 8-dimethyl-4-oxobenzo[d][1,2,3]triazin-3 (4H)-yl)-N-(1 -(4-methoxyphenyl)ethyl)acetamide;
(S)-2-(4-oxo-6-(trifluoromethyl)benzo[d][1,2,3]triazin-3 (4H)-yl)-N-(1-p-tolylethyl)acetamide;
(S)-N-(1-(4-methoxyphenyl)ethyl)-2-(4-oxo-6-(trifluoromethyl)benzo[d][1,2,3]triazin-3 (4H)-yl)acetamide;
(S)-2-(8-fluoro-6-methyl-4-oxobenzo[d][1,2,3]triazin-3 (4H)-yl)-N-(1 -(p-tolyl)ethyl)acetamide;
(S)-N-(1 -(2-methoxy-4-methylphenyl)ethyl)-2-(4-oxobenzo[d][1,2,3]triazin-3 (4H)-yl)acetamide;
(S)-N-(1-(2-chloro-4-fluorophenyl)ethyl)-2-(4-oxobenzo[d][1,2,3]triazin-3 (4H)-yl)acetamide;
(S)-N-(1-(2-bromo-4-fluorophenyl)ethyl)-2-(4-oxobenzo[d][1,2,3]triazin-3 (4H)-yl)acetamide;
(S)-N-((S)-1 -(2-methoxy-4-methylphenyl)ethyl)-2-(4-oxobenzo[d][1,2,3]triazin-3 (4H)-yl)propanamide;
(R)-N-((S)- 1 -(2-methoxy-4-methylphenyl)ethyl)-2-(4-oxobenzo[d][1,2,3]triazin-3 (4H)-yl)propanamide;
(S)-N-(1 -(2,4-dimethylphenyl)ethyl)-2-(6-fluoro-4-oxobenzo[d][1,2,3]triazin-3 (4H)-yl)acetamide;
(S)-N-(1-(2-fluoro-4-methylphenyl)ethyl)-2-(4-oxobenzo[d][1,2,3]triazin-3 (4H)-yl)acetamide;
(S)-N-(1-(2-fluoro-4-methylphenyl)ethyl)-2-(6-fluoro-4-oxobenzo[d][1,2,3]triazin-3 (4H)-yl)acetamide;
(S)-2-(6-fluoro-4-oxobenzo[d][1,2,3]triazin-3 (4H)-yl)-N-(1 -(4-(trifluoromethoxy)phenyl)ethyl)acetamide;
(S)-2-(7-methoxy-4-oxobenzo[d][1,2,3]triazin-3 (4H)-yl)-N-(1 -(4-(trifluoromethoxy)phenyl)ethyl)acetamide;
(S)-2-(6-methoxy-4-oxobenzo[d][1,2,3]triazin-3 (4H)-yl)-N-(1 -(4-(trifluoromethoxy)phenyl)ethyl)acetamide;
(S)-2-(5-methoxy-4-oxobenzo[d][1,2,3]triazin-3(4H)-yl)-N-(1-(4-(trifluoromethoxy)phenyl)ethyl)acetamide;
(S)-2-(7-methoxy-4-oxobenzo[d][1,2,3]triazin-3(4H)-yl)-N-(1-(4-(trifluoromethyl)phenyl)ethyl)acetamide;
(S)-2-(6-methoxy-4-oxobenzo[d][1,2,3]triazin-3(4H)-yl)-N-(1-(4-(trifluoromethyl)phenyl)ethyl)acetamide;
(S)-2-(8-methoxy-4-oxobenzo[d][1,2,3]triazin-3(4H)-yl)-N-(1-(4-(trifluoromethoxy)phenyl)ethyl)acetamide;
(S)-2-(8-methoxy-4-oxobenzo[d][1,2,3]triazin-3(4H)-yl)-N-(1-(4-(trifluoromethyl)phenyl)ethyl)acetamide;
(S)-2-(6-fluoro-4-oxobenzo[d][1,2,3]triazin-3(4H)-yl)-N-(1-(4-(trifluoromethyl)phenyl)ethyl)acetamide;
(S)-N-(1-(2-fluoro-4-(trifluoromethyl)phenyl)ethyl)-2-(4-oxobenzo[d][1,2,3]triazin-3(4H)-yl)acetamide;
(S)-N-(1-(4-(difluoromethoxy)phenyl)ethyl)-2-(4-oxobenzo[d][1,2,3]triazin-3(4H)-yl)acetamide;
(S)-N-(1-(2-fluoro-4-(trifluoromethyl)phenyl)ethyl)-2-(5-methoxy-4-oxobenzo[d][1,2,3]triazin-3(4H)-yl)acetamide;
(S)-N-(1-(4-(difluoromethoxy)phenyl)ethyl)-2-(6-fluoro-4-oxobenzo[d][1,2,3]triazin-3(4H)-yl)acetamide;
(S)-N-(1-(4-(difluoromethoxy)phenyl)ethyl)-2-(5-methoxy-4-oxobenzo[d][1,2,3]triazin-3(4H)-yl)acetamide;
(S)-N-(1-(2-fluoro-4-(trifluoromethoxy)phenyl)ethyl)-2-(4-oxobenzo[d][1,2,3]triazin-3(4H)-yl)acetamide;
(S)-N-(1-(2-fluoro-4-(trifluoromethoxy)phenyl)ethyl)-2-(6-fluoro-4-oxobenzo[d][1,2,3]triazin-3(4H)-yl)acetamide;
(S)-N-(1-(2-fluoro-4-(trifluoromethoxy)phenyl)ethyl)-2-(5-methoxy-4-oxobenzo[d][1,2,3]triazin-3(4H)-yl)acetamide; and
a pharmaceutically acceptable salt of any one of the above-mentioned compounds.

12. The method according to claim 1, wherein the compound is selected from the group of compounds consisting of:
(S)-2-(4-oxob enzo [d][1,2,3]tri azin-3 (4H)-yl)-N-(1-(4-(trifluoromethoxy)phenyl)propyl)acetamide;
(S)-2-(4-oxobenzo [d][1,2,3]tri azin-3 (4H)-yl)-N-(1-(4-(trifluoromethyl)phenyl)propyl)acetamide; and
a pharmaceutically acceptable salt of any one of the above-mentioned compounds.

13. The method according to claim 1, wherein the compound is (S)-2-(4-oxobenzo[d][1,2,3]triazin-3 (4H)-yl)-N-(1 -(4-(trifluoromethoxy)phenyl)ethyl)acetamide or a pharmaceutically acceptable salt thereof.

14. The method according to claim 1, wherein the compound is (S)-2-(4-oxobenzo[d][1,2,3]triazin-3(4H)-yl)-N-(1-(4-(trifluoromethyl)phenyl)ethyl)acetamide or a pharmaceutically acceptable salt thereof.

15. The method according to claim 1, wherein the compound is (S)-2-(5-fluoro-4-oxobenzo[d][1,2,3]triazin-3 (4H)-yl)-N-(1-p-tolylethyl)acetamide or a pharmaceutically acceptable salt thereof.

16. The method according to claim 1, wherein the compound is (S)-2-(5-methoxy-4-oxobenzo[d][1,2,3]triazin-3 (4H)-yl)-N-(1-(4-(trifluoromethyl)phenyl)ethyl)acetamide or a pharmaceutically acceptable salt thereof.

17. A method for agonizing GPR139 in a subject, the method comprising administering to the subject a compound of formula 1, or a pharmaceutically acceptable salt thereof, wherein:
m is selected from 0, 1, and 2;
n is selected from 0, 1, and 2;
each $R_1$ is independently selected from the group consisting of cyano, halo, hydroxy, amino, $C_{1-4}$ alkyl, $C_{1-4}$ alkoxy, trifluoromethyl, and trifluoromethoxy;
$R_2$ is selected from the group consisting of hydrogen and $C_{1-4}$ alkyl;
$R_3$ is selected from the group consisting of hydrogen and methyl;
each $R_4$ is independently selected from the group consisting of cyano, halo, hydroxy, amino, $C_{1-4}$ alkyl, $C_{1-4}$ alkoxy, trifluoromethyl, fluoromethoxy, difluoromethoxy, and trifluoromethoxy;
G is selected from the group consisting of —$CHR_5$—, —$CHR_5$—$CH_2$—, and —$CH_2$—$CHR_5$—; and
$R_5$ is selected from the group consisting of hydrogen, trifluoromethyl, and $C_{1-4}$ alkyl.

18. The method according to claim 17, wherein G is —$CHR_5$—.

19. The method according to claim 17, wherein $R_5$ is selected from the group consisting of methyl, ethyl, and isopropyl.

20. The method according to claim 17, wherein $R_5$ is methyl.

21. The method according to claim 17, wherein the compound is substantially enantiomerically pure and has a structure represented by formula 1A,

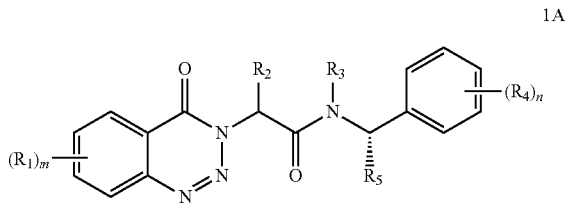

wherein $R_5$ is selected from the group consisting of trifluoromethyl and $C_{1-4}$ alkyl.

22. The method according to claim 17, wherein $R_2$ is hydrogen.

23. The method according to claim 17, wherein $R_3$ is hydrogen.

24. The method according to claim 17, wherein m is 0.

25. The method according to claim 17, wherein m is 1.

26. The method according to claim 25, wherein $R_1$ is selected from the group consisting of halo, $C_{1-4}$ alkyl, $C_{1-4}$ alkoxy, trifluoromethyl, and trifluoromethoxy.

27. The method according to claim 25, wherein $R_1$ is $C_{1-4}$ alkoxy.

28. The method according to claim 17, wherein m is 2.

29. The method according to claim 17, wherein n is 1 and $R_4$ is selected from the group consisting of halo, $C_{1-4}$ alkyl, $C_{1-4}$ alkoxy, trifluoromethyl, fluoromethoxy, difluoromethoxy, and trifluoromethoxy.

30. The method according to claim 17, wherein n is 1 and $R_4$ is selected from the group consisting of $C_{1-4}$ alkyl and trifluoromethoxy.

31. The method according to claim 17, wherein the compound is selected from the group of compounds consisting of:

2-(4-oxobenzo[d][1,2,3]triazin-3(4H)-yl)-N-(1-phenylethyl)acetamide;
2-(5-methoxy-4-oxobenzo[d][1,2,3]triazin-3(4H)-yl)-N-(1-p-tolylethyl)acetamide;
N-(1-(4-bromophenyl)ethyl)-2-(4-oxobenzo[d][1,2,3]triazin-3(4H)-yl)acetamide;
2-(4-oxobenzo[d][1,2,3]triazin-3(4H)-yl)-N-(1-p-tolylethyl)acetamide;
N-(1-(4-methoxyphenyl)ethyl)-2-(4-oxobenzo[d][1,2,3]triazin-3(4H)-yl)acetamide;
N-(1-(4-chlorophenyl)ethyl)-2-(4-oxobenzo[d][1,2,3]triazin-3(4H)-yl)acetamide;
N-(1-(2,4-dimethylphenyl)ethyl)-2-(4-oxobenzo[d][1,2,3]triazin-3(4H)-yl)acetamide;
2-(4-oxobenzo[d][1,2,3]triazin-3(4H)-yl)-N-(1-o-tolylethyl)acetamide;
N-(1-(4-ethoxyphenyl)ethyl)-2-(4-oxobenzo[d][1,2,3]triazin-3(4H)-yl)acetamide;
N-(1-(2,4-dimethoxyphenyl)ethyl)-2-(4-oxobenzo[d][1,2,3]triazin-3(4H)-yl)acetamide;
2-(4-oxobenzo[d][1,2,3]triazin-3(4H)-yl)-N-(1-(4-(trifluoromethyl)phenyl)ethyl)acetamide;
2-(6-fluoro-4-oxobenzo[d][1,2,3]triazin-3(4H)-yl)-N-(1-p-tolylethyl)acetamide;
2-(6-fluoro-4-oxobenzo[d][1,2,3]triazin-3(4H)-yl)-N-(1-(4-methoxyphenyl)ethyl)acetamide;
2-(8-fluoro-4-oxobenzo[d][1,2,3]triazin-3(4H)-yl)-N-(1-p-tolylethyl)acetamide;
2-(8-fluoro-4-oxobenzo[d][1,2,3]triazin-3(4H)-yl)-N-(1-(4-methoxyphenyl)ethyl)acetamide;
2-(6-methoxy-4-oxobenzo[d][1,2,3]triazin-3(4H)-yl)-N-(1-p-tolylethyl)acetamide;
2-(6-chloro-4-oxobenzo[d][1,2,3]triazin-3(4H)-yl)-N-(1-p-tolylethyl)acetamide;
2-(6-chloro-4-oxobenzo[d][1,2,3]triazin-3(4H)-yl)-N-(1-(4-methoxyphenyl)ethyl)acetamide;
2-(7-chloro-4-oxobenzo[d][1,2,3]triazin-3(4H)-yl)-N-(1-p-tolylethyl)acetamide;
2-(8-chloro-4-oxobenzo[d][1,2,3]triazin-3(4H)-yl)-N-(1-p-tolylethyl)acetamide;
2-(8-chloro-4-oxobenzo[d][1,2,3]triazin-3(4H)-yl)-N-(1-(4-methoxyphenyl)ethyl)acetamide;
2-(8-methyl-4-oxobenzo[d][1,2,3]triazin-3(4H)-yl)-N-(1-p-tolylethyl)acetamide;
N-(1-(4-methoxyphenyl)ethyl)-2-(8-methyl-4-oxobenzo[d][1,2,3]triazin-3(4H)-yl)acetamide;
2-(6,8-dichloro-4-oxobenzo[d][1,2,3]triazin-3(4H)-yl)-N-(1-p-tolylethyl)acetamide;
2-(6,8-dichloro-4-oxobenzo[d][1,2,3]triazin-3(4H)-yl)-N-(1-(4-methoxyphenyl)ethyl)acetamide;
2-(6-methyl-4-oxobenzo[d][1,2,3]triazin-3(4H)-yl)-N-(1-p-tolylethyl)acetamide;
N-(1-(4-methoxyphenyl)ethyl)-2-(6-methyl-4-oxobenzo[d][1,2,3]triazin-3(4H)-yl)acetamide;
2-(8-methoxy-4-oxobenzo[d][1,2,3]triazin-3(4H)-yl)-N-(1-p-tolylethyl)acetamide;
2-(8-methoxy-4-oxobenzo[d][1,2,3]triazin-3(4H)-yl)-N-(1-(4-methoxyphenyl)ethyl)acetamide;
2-(5-fluoro-4-oxobenzo[d][1,2,3]triazin-3(4H)-yl)-N-(1-p-tolylethyl)acetamide;
2-(5-fluoro-4-oxobenzo[d][1,2,3]triazin-3(4H)-yl)-N-(1-(4-methoxyphenyl)ethyl)acetamide;
2-(7-methyl-4-oxobenzo[d][1,2,3]triazin-3(4H)-yl)-N-(1-p-tolylethyl)acetamide;
N-(1-(4-methoxyphenyl)ethyl)-2-(7-methyl-4-oxobenzo[d][1,2,3]triazin-3(4H)-yl)acetamide;
2-(7-methoxy-4-oxobenzo[d][1,2,3]triazin-3(4H)-yl)-N-(1-p-tolylethyl)acetamide;
2-(7-methoxy-4-oxobenzo[d][1,2,3]triazin-3(4H)-yl)-N-(1-(4-methoxyphenyl)ethyl)acetamide;
2-(5-methoxy-4-oxobenzo[d][1,2,3]triazin-3(4H)-yl)-N-(1-(4-methoxyphenyl)ethyl)acetamide;
N-(1-(4-methoxyphenyl)ethyl)-2-(5-methyl-4-oxobenzo[d][1,2,3]triazin-3(4H)-yl)acetamide;
2-(6,8-dimethyl-4-oxobenzo[d][1,2,3]triazin-3(4H)-yl)-N-(1-(4-methoxyphenyl)ethyl)acetamide;
2-(4-oxo-6-(trifluoromethyl)benzo[d][1,2,3]triazin-3(4H)-yl)-N-(1-p-tolylethyl)acetamide;
N-(1-(4-methoxyphenyl)ethyl)-2-(4-oxo-6-(trifluoromethyl)benzo[d][1,2,3]triazin-3(4H)-yl)acetamide;
2-(8-fluoro-6-methyl-4-oxobenzo[d][1,2,3]triazin-3(4H)-yl)-N-(1-(p-tolyl)ethyl)acetamide;
N-(1-(2-methoxy-4-methylphenyl)ethyl)-2-(4-oxobenzo[d][1,2,3]triazin-3(4H)-yl)acetamide;
N-(1-(2-chloro-4-fluorophenyl)ethyl)-2-(4-oxobenzo[d][1,2,3]triazin-3(4H)-yl)acetamide;
N-(1-(2-bromo-4-fluorophenyl)ethyl)-2-(4-oxobenzo[d][1,2,3]triazin-3(4H)-yl)acetamide;
N-(1-(4-fluorophenyl)ethyl)-2-(4-oxobenzo[d][1,2,3]triazin-3(4H)-yl)acetamide;
N-(1-(2-methoxy-4-methylphenyl)ethyl)-2-(4-oxobenzo[d][1,2,3]triazin-3(4H)-yl)propanamide;
N-(1-(2,4-dimethylphenyl)ethyl)-2-(6-fluoro-4-oxobenzo[d][1,2,3]triazin-3(4H)-yl)acetamide;
N-(1-(2-fluoro-4-methylphenyl)ethyl)-2-(4-oxobenzo[d][1,2,3]triazin-3(4H)-yl)acetamide;
N-(1-(2-fluoro-4-methylphenyl)ethyl)-2-(6-fluoro-4-oxobenzo[d][1,2,3]triazin-3(4H)-yl)acetamide;

2-(6-fluoro-4-oxobenzo[d][1,2,3]triazin-3(4H)-yl)-N-(1-(4-(trifluoromethoxy)phenyl)ethyl)acetamide;
2-(7-methoxy-4-oxobenzo[d][1,2,3]triazin-3(4H)-yl)-N-(1-(4-(trifluoromethoxy)phenyl)ethyl)acetamide;
2-(6-methoxy-4-oxobenzo[d][1,2,3]triazin-3(4H)-yl)-N-(1-(4-(trifluoromethoxy)phenyl)ethyl)acetamide;
2-(5-methoxy-4-oxobenzo[d][1,2,3]triazin-3(4H)-yl)-N-(1-(4-(trifluoromethoxy)phenyl)ethyl)acetamide;
2-(7-methoxy-4-oxobenzo[d][1,2,3]triazin-3(4H)-yl)-N-(1-(4-(trifluoromethyl)phenyl)ethyl)acetamide;
2-(6-methoxy-4-oxobenzo[d][1,2,3]triazin-3(4H)-yl)-N-(1-(4-(trifluoromethyl)phenyl)ethyl)acetamide;
2-(5-methoxy-4-oxobenzo[d][1,2,3]triazin-3(4H)-yl)-N-(1-(4-(trifluoromethyl)phenyl)ethyl)acetamide;
2-(8-methoxy-4-oxobenzo[d][1,2,3]triazin-3(4H)-yl)-N-(1-(4-(trifluoromethoxy)phenyl)ethyl)acetamide;
2-(8-methoxy-4-oxobenzo[d][1,2,3]triazin-3(4H)-yl)-N-(1-(4-(trifluoromethyl)phenyl)ethyl)acetamide;
2-(6-fluoro-4-oxobenzo[d][1,2,3]triazin-3(4H)-yl)-N-(1-(4-(trifluoromethyl)phenyl)ethyl)acetamide;
N-(1-(2-fluoro-4-(trifluoromethyl)phenyl)ethyl)-2-(4-oxobenzo[d][1,2,3]triazin-3(4H)-yl)acetamide;
N-(1-(4-(difluoromethoxy)phenyl)ethyl)-2-(4-oxobenzo[d][1,2,3]triazin-3(4H)-yl)acetamide;
N-(1-(2-fluoro-4-(trifluoromethyl)phenyl)ethyl)-2-(5-methoxy-4-oxobenzo[d][1,2,3]triazin-3(4H)-yl)acetamide;
N-(1-(4-(difluoromethoxy)phenyl)ethyl)-2-(6-fluoro-4-oxobenzo[d][1,2,3]triazin-3(4H)-yl)acetamide;
N-(1-(4-(difluoromethoxy)phenyl)ethyl)-2-(5-methoxy-4-oxobenzo[d][1,2,3]triazin-3(4H)-yl)acetamide;
N-(1-(2-fluoro-4-(trifluoromethoxy)phenyl)ethyl)-2-(4-oxobenzo[d][1,2,3]triazin-3(4H)-yl)acetamide;
N-(1-(2-fluoro-4-(trifluoromethoxy)phenyl)ethyl)-2-(6-fluoro-4-oxobenzo[d][1,2,3]triazin-3(4H)-yl)acetamide;
N-(1-(2-fluoro-4-(trifluoromethoxy)phenyl)ethyl)-2-(5-methoxy-4-oxobenzo[d][1,2,3]triazin-3(4H)-yl)acetamide; and
a pharmaceutically acceptable salt of any one of the above-mentioned compounds.

32. The method according to claim 17, wherein the compound is selected from the group of compounds consisting of:

(S)-2-(4-oxobenzo[d][1,2,3]triazin-3(4H)-yl)-N-(1-phenylethyl)acetamide;
(S)-2-(5-methoxy-4-oxobenzo[d][1,2,3]triazin-3(4H)-yl)-N-(1-p-tolylethyl)acetamide;
(S)-N-(1-(4-bromophenyl)ethyl)-2-(4-oxobenzo[d][1,2,3]triazin-3(4H)-yl)acetamide;
(S)-2-(4-oxobenzo[d][1,2,3]triazin-3(4H)-yl)-N-(1-p-tolylethyl)acetamide;
(R)-2-(4-oxobenzo[d][1,2,3]triazin-3(4H)-yl)-N-(1-p-tolylethyl)acetamide;
(S)-N-(1-(4-methoxyphenyl)ethyl)-2-(4-oxobenzo[d][1,2,3]triazin-3(4H)-yl)acetamide;
(S)-N-(1-(4-chlorophenyl)ethyl)-2-(4-oxobenzo[d][1,2,3]triazin-3(4H)-yl)acetamide;
(S)-N-(1-(2,4-dimethylphenyl)ethyl)-2-(4-oxobenzo[d][1,2,3]triazin-3(4H)-yl)acetamide;
(S)-2-(4-oxobenzo[d][1,2,3]triazin-3(4H)-yl)-N-(1-o-tolylethyl)acetamide;
(S)-N-(1-(4-ethoxyphenyl)ethyl)-2-(4-oxobenzo[d][1,2,3]triazin-3(4H)-yl)acetamide;
(S)-N-(1-(2,4-dimethoxyphenyl)ethyl)-2-(4-oxobenzo[d][1,2,3]triazin-3(4H)-yl)acetamide;
(S)-2-(6-fluoro-4-oxobenzo[d][1,2,3]triazin-3(4H)-yl)-N-(1-p-tolylethyl)acetamide;
(S)-2-(6-fluoro-4-oxobenzo[d][1,2,3]triazin-3(4H)-yl)-N-(1-(4-methoxyphenyl)ethyl)acetamide;
(S)-2-(8-fluoro-4-oxobenzo[d][1,2,3]triazin-3(4H)-yl)-N-(1-p-tolylethyl)acetamide;
(S)-2-(8-fluoro-4-oxobenzo[d][1,2,3]triazin-3(4H)-yl)-N-(1-(4-methoxyphenyl)ethyl)acetamide;
(S)-2-(6-methoxy-4-oxobenzo[d][1,2,3]triazin-3(4H)-yl)-N-(1-p-tolylethyl)acetamide;
(S)-2-(6-chloro-4-oxobenzo[d][1,2,3]triazin-3(4H)-yl)-N-(1-p-tolylethyl)acetamide;
(S)-2-(6-chloro-4-oxobenzo[d][1,2,3]triazin-3(4H)-yl)-N-(1-(4-methoxyphenyl)ethyl)acetamide;
(S)-2-(7-chloro-4-oxobenzo[d][1,2,3]triazin-3(4H)-yl)-N-(1-p-tolylethyl)acetamide;
(S)-2-(8-chloro-4-oxobenzo[d][1,2,3]triazin-3(4H)-yl)-N-(1-p-tolylethyl)acetamide;
(S)-2-(8-chloro-4-oxobenzo[d][1,2,3]triazin-3(4H)-yl)-N-(1-(4-methoxyphenyl)ethyl)acetamide;
(S)-2-(8-methyl-4-oxobenzo[d][1,2,3]triazin-3(4H)-yl)-N-(1-p-tolylethyl)acetamide;
(S)-N-(1-(4-methoxyphenyl)ethyl)-2-(8-methyl-4-oxobenzo[d][1,2,3]triazin-3(4H)-yl)acetamide;
(S)-2-(6,8-dichloro-4-oxobenzo[d][1,2,3]triazin-3(4H)-yl)-N-(1-p-tolylethyl)acetamide;
(S)-2-(6,8-dichloro-4-oxobenzo[d][1,2,3]triazin-3(4H)-yl)-N-(1-(4-methoxyphenyl)ethyl)acetamide;
(S)-2-(6-methyl-4-oxobenzo[d][1,2,3]triazin-3(4H)-yl)-N-(1-p-tolylethyl)acetamide;
(S)-N-(1-(4-methoxyphenyl)ethyl)-2-(6-methyl-4-oxobenzo[d][1,2,3]triazin-3(4H)-yl)acetamide;
(S)-2-(8-methoxy-4-oxobenzo[d][1,2,3]triazin-3(4H)-yl)-N-(1-p-tolylethyl)acetamide;
(S)-2-(8-methoxy-4-oxobenzo[d][1,2,3]triazin-3(4H)-yl)-N-(1-(4-methoxyphenyl)ethyl)acetamide;
(S)-2-(5-fluoro-4-oxobenzo[d][1,2,3]triazin-3(4H)-yl)-N-(1-(4-methoxyphenyl)ethyl)acetamide;
(S)-2-(7-methyl-4-oxobenzo[d][1,2,3]triazin-3(4H)-yl)-N-(1-p-tolylethyl)acetamide;
(S)-N-(1-(4-methoxyphenyl)ethyl)-2-(7-methyl-4-oxobenzo[d][1,2,3]triazin-3(4H)-yl)acetamide;
(S)-2-(7-methoxy-4-oxobenzo[d][1,2,3]triazin-3(4H)-yl)-N-(1-p-tolylethyl)acetamide;
(S)-2-(7-methoxy-4-oxobenzo[d][1,2,3]triazin-3(4H)-yl)-N-(1-(4-methoxyphenyl)ethyl)acetamide;
(S)-2-(5-methoxy-4-oxobenzo[d][1,2,3]triazin-3(4H)-yl)-N-(1-(4-methoxyphenyl)ethyl)acetamide;
(S)-N-(1-(4-methoxyphenyl)ethyl)-2-(5-methyl-4-oxobenzo[d][1,2,3]triazin-3(4H)-yl)acetamide;
(S)-2-(6,8-dimethyl-4-oxobenzo[d][1,2,3]triazin-3(4H)-yl)-N-(1-(4-methoxyphenyl)ethyl)acetamide;
(S)-2-(4-oxo-6-(trifluoromethyl)benzo[d][1,2,3]triazin-3(4H)-yl)-N-(1-p-tolylethyl)acetamide;
(S)-N-(1-(4-methoxyphenyl)ethyl)-2-(4-oxo-6-(trifluoromethyl)benzo[d][1,2,3]triazin-3(4H)-yl)acetamide;
(S)-2-(8-fluoro-6-methyl-4-oxobenzo[d][1,2,3]triazin-3(4H)-yl)-N-(1-(p-tolyl)ethyl)acetamide;
(S)-N-(1-(2-methoxy-4-methylphenyl)ethyl)-2-(4-oxobenzo[d][1,2,3]triazin-3(4H)-yl)acetamide;
(S)-N-(1-(2-chloro-4-fluorophenyl)ethyl)-2-(4-oxobenzo[d][1,2,3]triazin-3(4H)-yl)acetamide;
(S)-N-(1-(2-bromo-4-fluorophenyl)ethyl)-2-(4-oxobenzo[d][1,2,3]triazin-3(4H)-yl)acetamide;
(S)-N-(1-(4-fluorophenyl)ethyl)-2-(4-oxobenzo[d][1,2,3]triazin-3(4H)-yl)acetamide;

(S)-N4S)-1-(2-methoxy-4-methylphenyl)ethyl)-2-(4-oxobenzo[d][1,2,3]triazin-3(4H)-yl)propanamide;
(R)-N4S)-1-(2-methoxy-4-methylphenyl)ethyl)-2-(4-oxobenzo[d][1,2,3]triazin-3(4H)-yl)propanamide;
(S)-N-(1-(2,4-dimethylphenyl)ethyl)-2-(6-fluoro-4-oxobenzo[d][1,2,3]triazin-3(4H)-yl)acetamide;
(S)-N-(1-(2-fluoro-4-methylphenyl)ethyl)-2-(4-oxobenzo[d][1,2,3]triazin-3(4H)-yl)acetamide;
(S)-N-(1-(2-fluoro-4-methylphenyl)ethyl)-2-(6-fluoro-4-oxobenzo[d][1,2,3]triazin-3(4H)-yl)acetamide;
(S)-2-(6-fluoro-4-oxobenzo[d][1,2,3]triazin-3(4H)-yl)-N-(1-(4-(trifluoromethoxy)phenyl)ethyl)acetamide;
(S)-2-(7-methoxy-4-oxobenzo[d][1,2,3]triazin-3(4H)-yl)-N-(1-(4-(trifluoromethoxy)phenyl)ethyl)acetamide;
(S)-2-(6-methoxy-4-oxobenzo[d][1,2,3]triazin-3(4H)-yl)-N-(1-(4-(trifluoromethoxy)phenyl)ethyl)acetamide;
(S)-2-(5-methoxy-4-oxobenzo[d][1,2,3]triazin-3(4H)-yl)-N-(1-(4-(trifluoromethoxy)phenyl)ethyl)acetamide;
(S)-2-(7-methoxy-4-oxobenzo[d][1,2,3]triazin-3(4H)-yl)-N-(1-(4-(trifluoromethyl)phenyl)ethyl)acetamide;
(S)-2-(6-methoxy-4-oxobenzo[d][1,2,3]triazin-3(4H)-yl)-N-(1-(4-(trifluoromethyl)phenyl)ethyl)acetamide;
(S)-2-(8-methoxy-4-oxobenzo[d][1,2,3]triazin-3(4H)-yl)-N-(1-(4-(trifluoromethoxy)phenyl)ethyl)acetamide;
(S)-2-(8-methoxy-4-oxobenzo[d][1,2,3]triazin-3(4H)-yl)-N-(1-(4-(trifluoromethyl)phenyl)ethyl)acetamide;
(S)-2-(6-fluoro-4-oxobenzo[d][1,2,3]triazin-3(4H)-yl)-N-(1-(4-(trifluoromethyl)phenyl)ethyl)acetamide;
(S)-N-(1-(2-fluoro-4-(trifluoromethyl)phenyl)ethyl)-2-(4-oxobenzo[d][1,2,3]triazin-3(4H)-yl)acetamide;
(S)-N-(1-(4-(difluoromethoxy)phenyl)ethyl)-2-(4-oxobenzo[d][1,2,3]triazin-3(4H)-yl)acetamide;
(S)-N-(1-(2-fluoro-4-(trifluoromethyl)phenyl)ethyl)-2-(5-methoxy-4-oxobenzo[d][1,2,3]triazin-3(4H)-yl)acetamide;
(S)-N-(1-(4-(difluoromethoxy)phenyl)ethyl)-2-(6-fluoro-4-oxobenzo[d][1,2,3]triazin-3(4H)-yl)acetamide;
(S)-N-(1-(4-(difluoromethoxy)phenyl)ethyl)-2-(5-methoxy-4-oxobenzo[d][1,2,3]triazin-3(4H)-yl)acetamide;
(S)-N-(1-(2-fluoro-4-(trifluoromethoxy)phenyl)ethyl)-2-(4-oxobenzo[d][1,2,3]triazin-3(4H)-yl)acetamide;
(S)-N-(1-(2-fluoro-4-(trifluoromethoxy)phenyl)ethyl)-2-(6-fluoro-4-oxobenzo[d][1,2,3]triazin-3(4H)-yl)acetamide;
(S)-N-(1-(2-fluoro-4-(trifluoromethoxy)phenyl)ethyl)-2-(5-methoxy-4-oxobenzo[d][1,2,3]triazin-3(4H)-yl)acetamide;
(S)-2-(4-oxobenzo[d][1,2,3]triazin-3(4H)-yl)-N-(2-phenylpropyl)acetamide;
(R)-2-(4-oxobenzo[d][1,2,3]triazin-3(4H)-yl)-N-(2-phenylpropyl)acetamide;
(R)-N-(1-(4-methoxyphenyl)propan-2-yl)-2-(4-oxobenzo[d][1,2,3]triazin-3(4H)-yl)acetamide;
(S)-N-(1-(4-methoxyphenyl)propan-2-yl)-2-(4-oxobenzo[d][1,2,3]triazin-3(4H)-yl)acetamide;
(S)-N-(1-(4-chloro-2-methoxyphenyl)propan-2-yl)-2-(4-oxobenzo[d][1,2,3]triazin-3(4H)-yl)acetamide;
(S)-N-(1-(2-chloro-4-methoxyphenyl)propan-2-yl)-2-(4-oxobenzo[d][1,2,3]triazin-3(4H)-yl)acetamide;
2-(4-oxobenzo[d][1,2,3]triazin-3(4H)-yl)-N-phenethylacetamide;
N-(4-chlorophenethyl)-2-(4-oxobenzo[d][1,2,3]triazin-3(4H)-yl)acetamide;
N-(3-chlorophenethyl)-2-(4-oxobenzo[d][1,2,3]triazin-3(4H)-yl)acetamide;
N-(4-methylphenethyl)-2-(4-oxobenzo[d][1,2,3]triazin-3(4H)-yl)acetamide;
N-(4-hydroxyphenethyl)-2-(4-oxobenzo[d][1,2,3]triazin-3(4H)-yl)acetamide;
N-(4-methoxyphenethyl)-N-methyl-2-(4-oxobenzo[d][1,2,3]triazin-3(4H)-yl)acetamide;
(S)-2-(4-oxobenzo[d][1,2,3]triazin-3(4H)-yl)-N-(2-phenylpropyl)acetamide;
(R)-2-(4-oxobenzo[d][1,2,3]triazin-3(4H)-yl)-N-(2-phenylpropyl)acetamide;
N-(2-chloro-4-methoxyphenethyl)-2-(4-oxobenzo[d][1,2,3]triazin-3(4H)-yl)acetamide;
(R)-N-(1-(4-methoxyphenyl)propan-2-yl)-2-(4-oxobenzo[d][1,2,3]triazin-3(4H)-yl)acetamide;
(S)-N-(1-(4-methoxyphenyl)propan-2-yl)-2-(4-oxobenzo[d][1,2,3]triazin-3(4H)-yl)acetamide;
(S)-N-(1-(4-chloro-2-methoxyphenyl)propan-2-yl)-2-(4-oxobenzo[d][1,2,3]triazin-3(4H)-yl)acetamide;
(S)-N-(1-(2-chloro-4-methoxyphenyl)propan-2-yl)-2-(4-oxobenzo[d][1,2,3]triazin-3(4H)-yl)acetamide; and
a pharmaceutically acceptable salt of any one of the above-mentioned compounds.

* * * * *